US008557982B2

(12) United States Patent
Chaplin et al.

(10) Patent No.: US 8,557,982 B2
(45) Date of Patent: Oct. 15, 2013

(54) TUBULIN POLYMERISATION INHIBITORS

(75) Inventors: Jason Hugh Chaplin, Thornbury (AU);
Gurmit Singh Gill, Craigieburn (AU);
Damian Wojciech Grobelny, Watsonia North (AU); Bernard Luke Flynn, Vermont (AU)

(73) Assignee: Bionomics Limited (AU)

( * ) Notice: Subject to any disclaimer, the term of this patent is extended or adjusted under 35 U.S.C. 154(b) by 0 days.

(21) Appl. No.: 13/584,046

(22) Filed: Aug. 13, 2012

(65) Prior Publication Data
US 2012/0309768 A1 Dec. 6, 2012

Related U.S. Application Data

(62) Division of application No. 11/816,209, filed as application No. PCT/AU2006/000192 on Feb. 14, 2006, now Pat. No. 8,278,290.

(60) Provisional application No. 60/652,668, filed on Feb. 14, 2005.

(51) Int. Cl.
*C07D 265/26* (2006.01)
*C07D 498/00* (2006.01)
*C07D 405/00* (2006.01)
*A61K 31/38* (2006.01)

(52) U.S. Cl.
USPC ........... 544/94; 544/95; 546/284.11; 548/119

(58) Field of Classification Search
USPC ........ 544/376; 546/284; 548/284.1, 119, 204, 548/266.4; 514/94, 95
See application file for complete search history.

(56) References Cited

U.S. PATENT DOCUMENTS

2010/0292190 A1 11/2010 Chaplin et al.

FOREIGN PATENT DOCUMENTS

| EP | 0759434 | 2/1997 |
| GB | 2282808 | 4/1995 |
| WO | WO 97/25033 | 7/1997 |
| WO | WO 02/060872 | 8/2002 |
| WO | WO 2006/084338 | 8/2006 |

OTHER PUBLICATIONS

Bishop, B.C. et al, "Synthesis of 3-Hydroxyalkylbenzobfuran Via the Palladium-Catalysed Heteroannulation of Silyl-Protected Alkynols With 2-Iodophenol ," Synthesis, 1997, 1315-1320.
Buchwald, et al, "A General, Efficient, and Inexpensive Catalyst System for the Coupling of Aryl Iodides and Thiols" Organic Letters, Oct. 2002, 4(20) 3517-3520.
Cacchi, S., et al. "Preparation of indoles from o-alkylnultrifluoroacetanilides through the aminopalladation-reductive elimination process", Synthesis, 2004, 11, 1889-1894.

Chaplin et al., "A multi-component coupling approach to benzo[b]furans and indoles," Chem. Comm., 2001, Issue 17, 1594-1595.
Collini, M.D. et al., "The Solid Phase Synthesis of Tri-Substituted Indoles," Tetrahedron Letters, Nov. 1997, 38, 7963-7966.
De Martino, G. et al., "Arylthioindoles, Potent Inhibitors of Tubulin Polymerization," J. Med. Chem., Dec. 2004, 47, 6120-6123.
Etemad-Moghadam et al., "Synthesis of $N^\alpha$-($\beta$-naphthylsulfonylaminoglycyl)-argininamides as potential selective synthetic thrombin inhibitors," European J. Med. Chem., Nov./Dec. 1988, 23(6), 577-585.
Flynn, B.L. et al., "A Novel Palladium-Mediated Coupling Approach to 2,3-Disubstituted Benzo[b]thiophenes and Its Application to the Synthesis of Tubulin Binding Agents," Org. Lett., Mar. 2001, 3(5), 651-654.
Flynn, B.L. et al., "One-Pot Synthesis of Benzo[b]furan and Indole Inhibitors of Tubulin Polymerization," J. Med. Chem, Jun. 2002, 45, 2670-2673.
Flynn, B.L. et al., "The Synthesis and Tubulin Binding Activity of Thiophene-Based Analogues of Combretastatin A-4," Bioorg Med. Chem. Lett., Sep. 2001, 11, 2341-2343.
Griggs, J. et al., "Targeting tumour vasculature: the development of combretastatin A4," The Lancet Oncology, Feb. 2001, 2, 82-87.
Han Y. et al, "Solid Phase Parallel Synthesis of Highly Substituted Thiophene Derivatives and Identification of Novel Phosphodiesterase-4 (PDE-4) Inhibitors," Tetrahedron, Sep. 1999, 55, 11669-11685.
Hessian, K.O. et al., "Iodine-Induced Reaction Cascades for the Rapid Construction of Variously Substituted Benzothiophenes," Org. Lett., Nov. 2003, 5, 4377-4380.
Iddon et al., "Metal-Halogen Exchange Reactions of Mono-and Poly-halogenoimidazoles," J. Chem. Soc., Perkin Trans. 1, 1983, 735-739.
Johnson, M.G., et al., "Solid Phase Chemistry Approach to the SAR Development of a Novel Class of Active Site-Directed Thrombin Inhibitors," Tetrahedron, Sep. 1999, 55, 11641-11642.
Jordan, M. et al., "Microtubules as a target for anticancer drugs," Nature Review/Cancer, Apr. 2004, 4, 253-265.
Li, Q. et al., "Discovery and development of antimitotic agents that inhibit tubulin polymerization for the treatment of cancer," Expert Opin. Ther. Patents, Nov. 2002, 12(11), 1663-1702.
Liou, J-P. et al., "Concise Synthesis and Structure-Activity Relationships of Combretastatin A-4 Analogues, 1-Aroylindoles and 3-Aroylindoles, as Novel Classes of Potent Antitubulin Agents," J. Med Chem., Aug. 2004, 47, 4247-4257.
Lutjens, H. et al., "Synthesis of 2-Substituted 3-Acylbenzo[b]furans via the Palladium Catalysed Carbonylative Cyclisation of ortho-Hydroxytolans," Synlett, Oct. 1999, 1079-1081.

(Continued)

Primary Examiner — Shirley V Gembeh
(74) Attorney, Agent, or Firm — Woodcock Washburn LLP

(57) ABSTRACT

The present invention relates to compounds of general formula (I) as tublin polymerization inhibitors and methods for preparing such compounds.

(I)

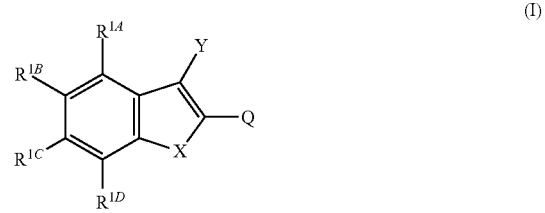

19 Claims, 1 Drawing Sheet

(56) References Cited

OTHER PUBLICATIONS

Marx, M.A., "Small-molecule, tubulin-binding compounds as vascular targeting agents," Expert Opin. Ther. Patents, Jun. 2002, 12, 769-776.

Medarde, M. et al., "Synthesis and pharmacological activity of Diarylindole derivatives. Cytoxic agents based on combretastatins," Bioorganic & Medicinal Chemistry Letters, Aug. 1999, 9(16), 2303-2308.

Morgan, L.R. et al., "Design, Synthesis, and Anticancer Properties of 4,4-Dihydrobenzophenone-2,4-dinitrophenylhydrazone and Analogues," J. Med. Chem., Oct. 2003, 46, 4552-4563.

Pettit, G. R., et al, "Antineoplastic agents 322. Synthesis of combretastatin A-4 prodrugs," Anticancer Drug Des., Jun. 1995, 10, 299-309.

Pinney, K.G. et al., "A New Anti-Tubulin Agent Containing the Benzo[b]thiophene ring system," Bioorg. Med. Chem. Lett., Apr. 1999, 9, 1081-1086.

Rodriguez-Franco, M.I. et al., "A mild and efficient method for the regioselective iodination of pyrazoles," Tetrahedron Letters, May 2001, 42, 863-865.

Sall, D.J. et al., "Diamino Benzo[b]thiophene Derivatives as a Novel Class of Active Site Directed Thrombin Inhibitors. 5. Potency, Efficacy, and Pharmacokinetic Properties of Modified C-3 Side Chain Derivatives," J. Med. Chem., Feb. 2000, 43(4), 649-663.

Sall, D.J. et al., "Dibasic Benzo[b]thiophene Derivatives as a Novel Class of Active Site-Directed Thrombin Inhibitors. 1. Determination of the Serine Protease Selectivity. Structure-Activity Relationships, and Binding Orientation," J. Med. Chem., Oct. 24, 1997, 40(22), 3489-3493.

Verdier-Pinard, P. et al., "Structure-Activity Analsys of the Interaction of Curacin A, the Potent Colchicine Site Antimitotic Agent, with Tubulin and Effects of Analogs on the Growth of MCF-7 Breast Canacer Cells," Mol. Pharmacol., Jan. 1998, 53, 62-76.

Wang, L. et al., "Potent, Orally Active Heterocycle-Based Combretastatin A-4 Analogues: Synthesis, Structure-Activity Relationship, Pharmacokinetics, and in Vivo Antitumor Activity Evaluation," J. Med. Chem., Apr. 2002, 45, 1697-1711.

TUBULIN POLYMERISATION INHIBITORS

RELATED APPLICATIONS

This application is a divisional application from U.S. patent application Ser. No. 11/816,209, filed Jun. 5, 2008, which is a National Stage Entry of PCT/AU06/00192, filed Feb. 14, 2006, which claims the benefit of priority to U.S. Patent Application Ser. No. 60/652,668, filed Feb. 14, 2005, each of which is incorporated by reference herein in its entirety.

FIELD OF THE INVENTION

The present invention relates generally to chemical compounds and methods for their use and preparation. In particular, the invention relates to chemical compounds which may possess useful therapeutic activity, use of these compounds in methods of therapy and the manufacture of medicaments as well as compositions containing these compounds.

BACKGROUND OF THE INVENTION

Tubulin is an important target in controlling disease states associated with cell proliferation such as cancer and inflammation (e.g., psoriasis). Tubulin is composed of a heterodimer of two related proteins called α and β tubulin. Tubulin polymerises to form structures called microtubules. Compounds that inhibit tubulin's ability to polymerise to form microtubules interrupt cell division which is dependent on the formation of microtubules to form mitotic spindles. Examples of such compounds include the Vinca alkaloids such as vincristine and vinblastine.

Furthermore, compounds that inhibit the depolymerisation of microtubules can also prevent cell division since they often disrupt the proper formation of mitotic spindles which must also disassemble in order for cell division to be completed. Interruption of the mitotic process in this manner often induces cell death by an apoptotic mechanism. Examples of compounds which act in this manner include the taxoids such as paclitaxel.

For these antimitotic agents, selectivity for diseased versus non-diseased tissue is based on relative rates of proliferation, where the diseased tissue more rapidly proliferates. Accordingly, diseased tissue is generally more sensitive to the effect of these agents because it is more likely to be in a state of mitosis which is the stage of a cell's life cycle affected by agents that target tubulin. Unfortunately however, a number of normal, healthy tissues also have quite high rates of proliferation (for example hair follicles and the lining of the gastro-intestinal tract) and accordingly, these tissues can be damaged during chemotherapy with these agents.

Tubulin is also a target for treating disease states that are dependent or result from the abnormal formation of blood vessels (neovascularisation) such as in cancerous tumours and in ocular myopathy. In these cases the cytoskeleton of the vascular endothelial cells are disrupted through depolymerisation of microtubules, which results from inhibiting the polymerisation of tubulin to form microtubules. Microtubule length is dependent on the rate of depolymerisation versus polymerisation. Depolymerising microtubules through inhibition of polymerisation leads to a change in endothelial cell morphology, which then causes a blockage or shutdown in blood flow. In the case of cancerous tumours, blood flow to the diseased tissue is stopped, depriving the tumour of oxygen and nutrients leading to necrotic cell death. Neovascular systems are more sensitive to these agents because they are more dependent on microtubule cytoskeletons than normal, healthy, vascular endothelial cells which are also supported by actin based cytoskeletal structures. For a number of tubulin polymerisation inhibitors (TPIs) that target the colchicine binding site of tubulin, the vascular targeting modality can be achieved at a lower in vivo concentration than the antiproliferative modality. In theory though, agents that target the colchicine binding domain of tubulin are potentially dual mode agents (i.e. antimitotic and antivascular).

One of the most potent inhibitors of tubulin polymerisation that binds to the colchicine binding domain of tubulin is the cis-stilbene, combretastatin A4 (CA4) (1). Due to its insolubility CA4 is administered as its prodrug equivalent combretastatin A4 disodium phosphate (CA4P) (2), where the phosphate is rapidly cleaved in vivo. CA4P is currently undergoing phase I and II clinical trials and is the most advanced vascular targeting agent being trialed. In view of some of the draw-backs associated with CA4P, such as, instability (can isomerise to the inactive trans-stilbene), toxicity and rapid clearance, a number of synthetic groups have sought to prepare more stable analogues that could be designed to exhibit an improved therapeutic index and exhibit improved pharmacokinetics. Recently, a number of TPIs have been identified that contain the benzofuran, indole or benzothiophene ring systems (3). Such ring systems are quite stable and should over come the stability issues associated with CA4P. Unfortunately, such compounds only exhibit moderate tubulin binding and anti-mitotic activity. Accordingly, there exists a need to identify other compounds which are more stable than CA4 and exhibit satisfactory pharmacological properties and/or activity.

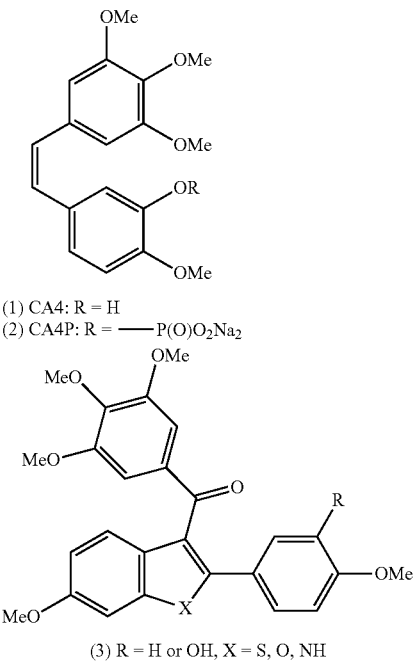

(1) CA4: R = H
(2) CA4P: R = —P(O)O$_2$Na$_2$ (3) R = H or OH, X = S, O, NH

SUMMARY OF THE INVENTION

The present invention provides compounds of formula (I) and salts thereof;

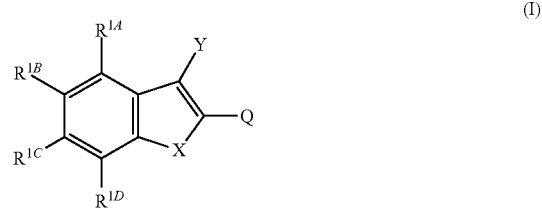

(I)

wherein;
X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$-$R^{1D}$ each independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, trihalomethoxy, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{1A}$ and $R^{1B}$, $R^{1B}$ and $R^{1C}$, and $R^{1C}$ and $R^{1D}$ together form an optionally substituted aryl, optionally substituted heterocyclyl, optionally substituted heteroaryl, optionally substituted cycloalkyl, or optionally substituted cycloalkenyl;

Y represents a group of formula (i) or (ii);

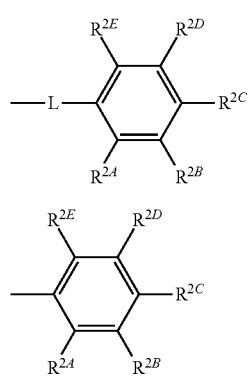

(i)

(ii)

wherein each $R^{2A}$-$R^{2D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethyl, ethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$ and $R^{2D}$ and $R^{2E}$, together form an optionally substituted aryl, optionally substituted heterocyclyl, optionally substituted heteroaryl, optionally substituted cycloalkyl, or optionally substituted cycloalkenyl;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

Q represents an optionally substituted heteroaryl group, optionally substituted heterocyclyl group, or a group of formula (iii);

-L-$R^3$ (iii);

wherein $R^3$ represents an optionally substituted heteroaryl group or an optionally substituted heterocyclyl group and L is as defined above; and when Y represents a group of formula (I), Q is an optionally substituted heteroaryl group or optionally substituted heterocyclyl group and when Y represents a group of formula (II), Q is a group of formula (iii); and when X is O and $R^{1C}$ is H or nitro, then $R^{1B}$ is not hydroxy or a $C_1$-$C_2$alkoxy group, and when X is S, $R^{2C}$ is not a substituted $C_1$-$C_2$ alkoxy group, and when X is NR, $R^{1C}$ is not H.

In one embodiment, when X is O and $R^{1C}$ is H or nitro, $R^{1B}$ is not hydroxy or a $C_1$-$C_6$alkoxy group. In another embodiment it is preferred that when X is S, $R^{2C}$ is not an optionally substituted $C_1$-$C_6$alkoxy.

The present invention also provides a method for treating a disease state by inhibiting tubulin polymerisation including the step of administering to a patient in need thereof a compound of formula (I) or a pharmaceutically acceptable salt thereof;

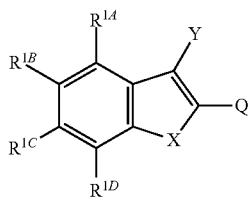

(I)

wherein;
X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$-$R^{1D}$ each independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or any of $R^{1A}$ and $R^{1B}$, $R^{1B}$ and $R^{1C}$, and $R^{1C}$ and $R^{1D}$ together form an optionally substituted aryl, optionally substituted heterocyclyl, optionally substituted heteroaryl, optionally substituted cycloalkyl, or optionally substituted cycloalkenyl;

Y represents a group of formula (I) or (ii);

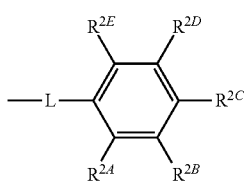

(i)

-continued

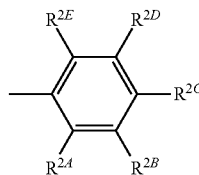

(ii)

wherein each $R^{2A}$-$R^{2D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

Q represents an optionally substituted heteroaryl group, optionally substituted heterocyclyl group, or a group of formula (iii);

-L-$R^3$ (iii)

wherein $R^3$ represents an optionally substituted heteroaryl group or an optionally substituted heterocyclyl group and L is as defined above; and when Y represents a group of formula (I), Q is an optionally substituted heteroaryl group or optionally substituted heterocyclyl group and when Y represents a group of formula (ii), Q is a group of formula (iii).

The present invention also provides the use of a compound of formula (I) or a salt thereof:

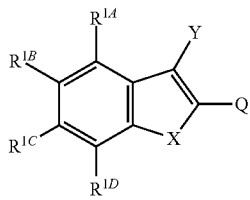
(I)

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{1A}$-$R^{1D}$ each independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{1A}$ and $R^{1B}$, $R^{1B}$ and $R^{1C}$, and $R^{1C}$ and $R^{1D}$ together form an optionally substituted aryl, optionally substituted heterocyclyl, optionally substituted heteroaryl, optionally substituted cycloalkyl, or optionally substituted cycloalkenyl;

Y represents a group of formula (i) or (ii);

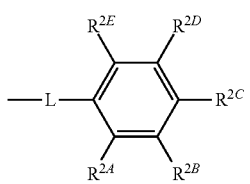
(i)

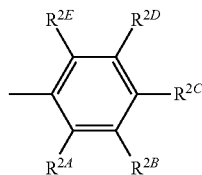
(ii)

wherein each $R^{2A}$-$R^{2D}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$ and $R^{2D}$ and $R^{2E}$, together form an optionally substituted aryl, optionally substituted heterocyclyl, optionally substituted heteroaryl, optionally substituted cycloalkyl, or optionally substituted cycloalkenyl;

L represents C=O, O, S, SO, SO$_2$, Se, SeO, SeO$_2$, C=NZ', or NR' where Z' is H, optionally substituted alkyl, optionally substituted aryl or optionally substituted amino; or NR' where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

Q represents an optionally substituted heteroaryl group, optionally substituted heterocyclyl group, or a group of formula (iii);

-L-R$^3$ (iii);

wherein R$^3$ represents an optionally substituted heteroaryl group or an optionally substituted heterocyclyl group and L is as defined above; and when Y represents a group of formula (i), Q is an optionally substituted heteroaryl group or optionally substituted heterocyclyl group and when Y represents a group of formula (ii), Q is a group of formula (iii);
in the manufacture of a medicament for the treatment of a disease state by inhibiting tubulin polymerisation.

DESCRIPTION OF THE PREFERRED EMBODIMENTS

Figure 1:
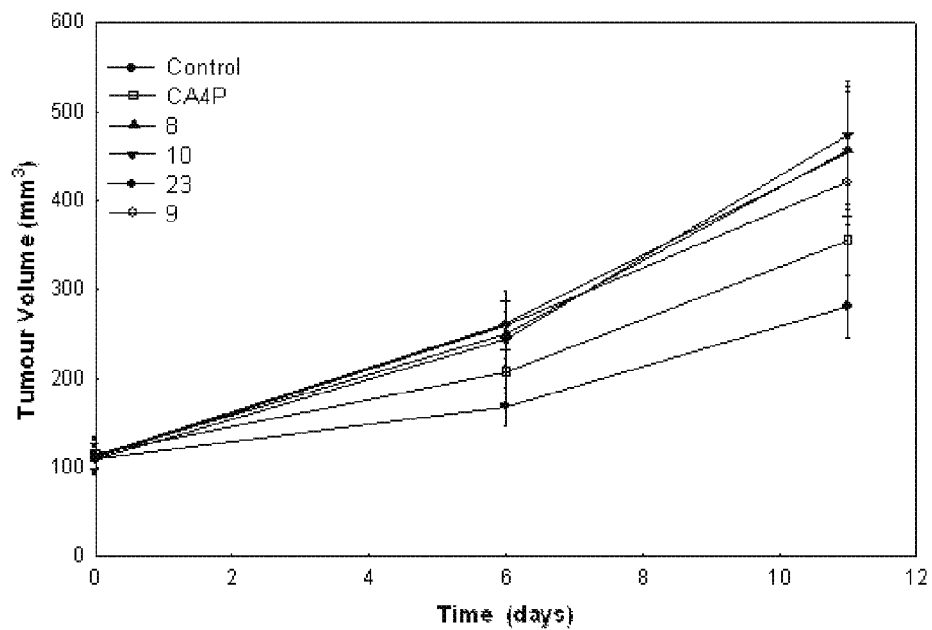
FIG. 1 depicts a graph of comparative Tumour Volume (mm$^3$) against time (days) for control, CA4-P, compound entry 8, compound entry 9, compound entry 10 and compound entry 23.

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Aryl" refers to an unsaturated aromatic carbocyclic group having a single ring (e.g. phenyl) or multiple condensed rings (e.g. naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$CCCH$_2$—CH$_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (i.e. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (e.g. pyridyl, pyrrolyl or N-oxides thereof or furyl) or multiple condensed rings (e.g. indolizinyl, benzoimidazolyl, coumarinyl, quinolinyl, isoquinolinyl or benzothienyl). It will be understood that where $R^3$ is an optionally substituted heteroaryl which has one or more ring heteroatoms, the heteroaryl group can be connected to the core molecule of the compounds of the present invention, as represented by formulae (I) (Ia) or (Ib), through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where $R^3$ is an optionally substituted heterocyclyl which has one or more ring heteroatoms, the heterocyclyl group can be connected to the core molecule of the compounds of the present invention, as represented by formulae (I), (Ia) or (Ib), through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR"—P(O)(R''')(OR'''') where R" represents H, alkyl, cycloalkyl, alkenyl, or aryl, R''' represents OR'''' or is hydroxy or amino and R'''' is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkylO—S(O)—NR"—, cycloalkylO—S(O)—NR"—, arylO—S(O)—NR"—, heteroarylO—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkylO—S(O)$_2$—NR"—, cycloalkylO—S(O)$_2$—NR"—, arylO—S(O)$_2$—NR"—, heteroarylO—S(O)$_2$—NR"—, and heterocyclylO—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl (which may be further substituted by amino, aminoacyl, oxyacyl, hydroxy, aryl and nitro), alkoxy, alkenyl, alkenyloxy, alkynyl, alkynyloxy, amino, aminoacyl, thio, arylalkyl, arylalkoxy (which may be further substituted by halogen, hydroxy, alkyl, nitro, alkoxy, acyl and amino), aryl (which may be further substituted by halogen, hydroxy, alkyl, nitro, alkoxy, acyl and amino), aryloxy (which may be further substituted by halogen, hydroxy, alkyl, nitro, alkoxy, acyl and amino), carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin).

In some embodiments $R^{1A}$-$R^{1D}$ and $R^{2A}$-$R^{2E}$ includes the following groups:

alkyl group, preferably methyl and ethyl;
substituted alkyl group, preferably 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;
acyl group, preferably formyl acetyl, propionyl, benzoyl (optionally substituted with methyl, methoxy, halogen, nitro, trifluoromethyl or cyano);
alkoxy group, preferably methoxy and ethoxy;
oxyacyl group, preferably methoxycarbonyl, ethoxycarbonyl, propoxycarbonyl, butyloxycarbonyl, isobutyloxycarbonyl;
acyloxy group, preferably acetoxy and propioxy;
substituted arylalkyl group, preferably 1-hydroxybenzyl, and 1-thiobenzyl;
sulfinyl group, preferably methylsulfinyl, ethylsulfinyl, benzene sulfinyl (optionally substituted with methyl, methoxy, halogen, nitro, trifluoromethane or cyano), methoxysulfinyl, ethoxysulfinyl;
sulfonyl group, preferably methylsulfonyl, ethylsulfonyl, benzenesulfonyl (optionally substituted with methyl, methoxy, halogen, nitro, trifluoromethane or cyano), methoxycarbo, trifluoromethane;
oxyacylamino group, preferably methoxycarbonylamido, and ethoxycarbonyl amido;
oxythioacyl group, preferably methoxythiocarbonyl and ethoxythiocarbonyl;
thioacyloxy group, preferably thionoacetoxy and thionopropionoxy;
sulphinylamino group, preferably methylsulfinylaminoi, ethylsulfinylamino, and benzenesulfinylamino (optionally substituted with methyl, methoxy, halogen, nitro, trifluoromethane or cyano);
amino group, preferably N-methylamino, and N,N'-dimethylamino;
substituted amino groups, preferably residues of L-valine, D-valine, L-alanine, D-alanine, aspartic acid, and alanylserine;
sulphonylamino group, preferably methylsulfonylamino, ethylsulfonylamino and benzene sulfonylamino (optionally substituted with methyl, methoxy, halogen, nitro, trifluoromethane or cyano);
substituted thio group, preferably alkylthio;
oxysulfinylamino group, preferably methoxysulfinylamino and ethoxysulfinylamino;
oxysulfonylamino group, preferably methoxysulfonylamino and ethoxysulfonylamino;
optionally substituted alkenyl group, preferably, 1-propenyl, vinyl, nitrovinyl, cyano vinyl, or trifluorovinyl and styryl (optionally substituted with methyl, methoxy, halogen, nitro, trifluoromethane or cyano);
alkynyl group, preferably 1-propynyl, ethynyl or trimethylsilylethynyl.

In a preferred embodiment Y represents a compound of formula (I) and Q represents an optionally substituted heteroaryl group or an optionally substituted heterocyclyl group and L is preferably a carbonyl group (C=O).

In this embodiment it is preferred that $R^{1C}$ represents hydroxy, an ether substituent, alkylthio, or mono or di-alkylamino Furthermore, it is preferred that $R^{2D}$ and $R^{2B}$ independently represent hydroxy or an ether substituent.

Accordingly, preferred compounds of the present invention are represented by formula (Ia)

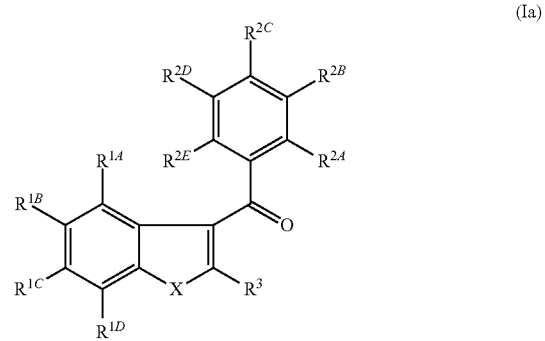

(Ia)

wherein;
X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;
$R^{1A}$, $R^{1B}$ and $R^{1D}$ each independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or $R^{1A}$ and $R^{1B}$, together form an optionally substituted aryl, optionally substituted heterocyclyl, optionally substituted heteroaryl, optionally substituted cycloalkyl, or optionally substituted cycloalkenyl;

$R^{1C}$ represents hydroxy, optionally substituted alkenyloxy, optionally substituted alkoxy, optionally substituted alkynyloxy, optionally substituted arylalkoxy, optionally substituted aryloxy, optionally substituted alkylthio or optionally substituted amino;

$R^{2A}$, $R^{2C}$ and $R^{2E}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy;

$R^{2D}$ and $R^{2B}$ independently represent hydroxy, optionally substituted arylalkoxy, optionally substituted alkenyloxy, optionally substituted alkoxy, optionally substituted alkynyloxy, or optionally substituted aryloxy;

$R^3$ represents an optionally substituted heteroaryl group or an optionally substituted heterocyclyl group; and when X is S, $R^{2C}$ is not a substituted $C_1$-$C_2$ alkoxy group.

In an even more preferred embodiment, $R^{1A}$, $R^{1B}$, $R^{2A}$ and $R^{2E}$ represent H and $R^{1C}$ represents $C_{1-3}$ alkoxy, $C_{1-3}$ alkylthio, $C_{1-3}$ alkylamino or $C_{1-3}$ dialkylamino. In this embodiment it is preferred that $R^{2C}$ represents H, halogen, or an alkoxy group, $R^{1D}$ represents halogen, hydroxy, optionally substituted amino or an optionally substituted alkoxy group, and $R^{2D}$ and $R^{2B}$ independently represent an alkoxy group.

Accordingly, even more preferred compounds of the present invention are represented by formula (Ib)

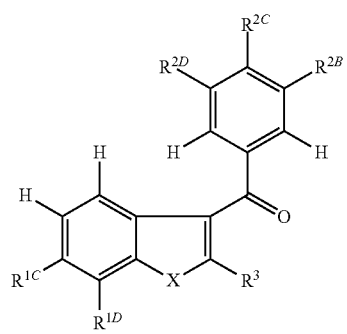

(Ib)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy, $C_{1-3}$ alkylthio, $C_{1-3}$ alkylamino or $C_{1-3}$ dialkylamino;

$R^{1D}$ represents H, hydroxy, halogen, optionally substituted alkoxy, or optionally substituted amino;

$R^{2D}$ and $R^{2B}$ independently represent alkoxy;

$R^{2C}$ represents H, halogen, or alkoxy; and $R^3$ represents an optionally substituted heteroaryl group or an optionally substituted heterocyclyl group.

In an even more preferred embodiment $R^{1D}$ is hydroxy or amino and $R^{2C}$ represents H, F or an alkoxy group, and more preferably methoxy. In this embodiment, $R^{2D}$ and $R^{2B}$ are the same and more preferably represent methoxy.

In the most preferred embodiment Y is a compound of formula (I) where L is C=O, $R^{1A}$, $R^{1B}$, $R^{2E}$ and $R^{2A}$ are H, $R^{2D}$, $R^{2C}$ and $R^{2B}$ are methoxy, $R^{1C}$ is $C_{1-3}$ alkoxy, $C_{1-3}$ alkylthio, $C_{1-3}$ alkylamino or $C_{1-3}$ dialkylamino and $R^{1D}$ is hydroxy or amino.

For the compounds represented by formulae I, Ia and Ib, X is preferably selected from O, S and NR. More preferably X is O or NR and most preferably X is O.

Furthermore, for the compounds of formulae (I), (Ia) and (Ib) it is even more preferred that $R^3$ represents an optionally substituted heteroaryl group. Accordingly, the most preferred compounds are represented by formulae (I), (Ia) and (Ib) where X is O and $R^3$ represents an optionally substituted heteroaryl group.

In the above mentioned embodiment, $R^3$ preferably represents either a 5 or 6 membered optionally substituted heteroaryl group, preferably having from 1 to 4 heteroatoms selected from O, S, Se, or N and mixtures thereof. Examples of preferred 5 membered optionally substituted heteroaryl groups include optionally substituted imidazolyl, optionally substituted triazolyl, optionally substituted pyrrolyl, optionally substituted pyrazolyl, optionally substituted thiazolyl, optionally substituted thiophenyl, optionally substituted furanyl, optionally substituted selenophenyl, optionally substituted oxazolyl, optionally substituted isoazolyl, optionally substituted isothiazolyl, optionally substituted oxadiazolyl, optionally substituted thiadiazolyl, optionally substituted tetrazolyl, optionally substituted oxatriazolyl, optionally substituted thiatriazolyl, optionally substituted indolyl, optionally substituted benzofuranyl and optionally substituted benzothiophenyl.

Examples of preferred 6 membered optionally substituted heteroaryl groups include optionally substituted pyridinyl, optionally substituted pyrimidinyl, optionally substituted pyronyl, optionally substituted coumarinyl, optionally substituted chromonyl, optionally substituted pyridonyl, optionally substituted purinyl (adeninyl and guaninyl), optionally substituted uracilyl, optionally substituted thymidinyl, optionally substituted cytosinyl, optionally substituted quinolinyl and optionally substituted isoquinolinyl.

The compounds of the present invention can be prepared by the multicomponent reaction system which has been described in PCT/AU02/00099 (WO 02/060872), the entire contents of which is incorporated herein by reference. In particular the compounds of the present invention can be prepared by the reaction sequence depicted in Scheme 1 below:

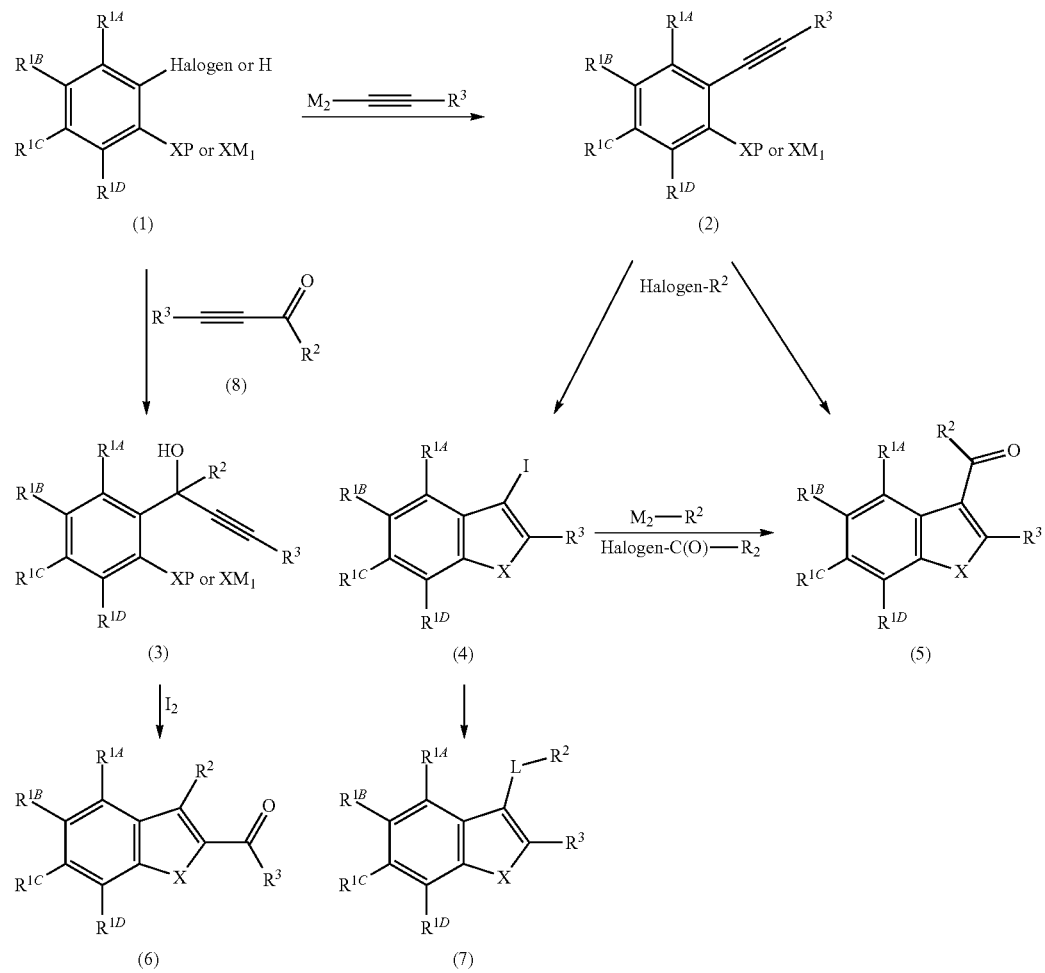

Scheme 1 where $R^3$ is an optionally substituted heteroaryl group,
$R^2$ is an optionally substituted aryl group of formula (II),
X is S, NR, O or Se, and
L is O, S, Se, SO, $SO_2$ or NR.

As shown above in Scheme 1, the compounds of formula I in which X is NR or O can be derived from reacting together a phenol or protected amine and terminal alkyne respectively. The starting phenol or aniline and terminal alkyne can be coupled together under conditions which allow for heteroannulation to spontaneously occur so as to form the target benzo[b]furan or indole in a "one-pot" synthetic strategy. Thus, the metal based compound required to form (2) (when $XM_1$) must be such that the phenol or protected amine is deprotonated to form the group $-OM_1$ or $NHM_1$.

Suitable $M_1$ are based on Li, Na, K, Mg, Cs and Ba as well as species formed therefrom, for example from Grignard reagents $C_{1-4}$alkyl MgHal (Hal=I, Cl or Br). Suitable metal species include MgCl, MgBr or MgI. Formation of (1) can be effected by treating the corresponding phenol or protected amine with, for example, $Li_2CO_3$, $Na_2CO_3$, $K_2CO_3$, $MgCO_3$, $Cs_2CO_3$, $BaCO_3$, MeMgCl, EtMgCl, MeMgBr, EtMgBr, MeMgI and EtMgI.

$M_2$ can be a hydrogen atom or metal species used in any palladium or nickel cross-coupling protocols known in the art, for example, Stille, Sonogashira, Suzuki or Negishi cross-coupling reactions using stannanes (e.g., aryl or alkylstannanes, boronic acids/esters or zinc based compounds e.g. $ZnCl$, $ZnI_2$, $ZnBr_2$, $ZnOTf_2$) for example based on Mg, Zn, Cu, B, Si, Mn, Sn, Ge or Al. Particularly suitable $M_2$ include $ZnCl$, $(alkyl)_3Sn$, $(aryl)_3Sn$, $B(OR)_2$ (R is, eg, H alkyl, alkenyl or alkynyl), MgBr, MgCl and MgI. Preferably the palladium catalysed coupling reactions may also include a co-catalyst, for instance, CuI, in the presence of a suitable base such as a trialkyl amine base.

In a particularly preferred form of this aspect of the invention both $M_1$ and $M_2$ are derived from a Grignard reagent such as an alkyl magnesium halide e.g. $C_{1-4}$alkylMgBr, (Cl) or (I). Suitable $M_1$ and $M_2$ thus include MgCl, MgBr and MgI.

Where X is NR, the nitrogen atom of the starting aniline is suitably protected by a nitrogen protecting group or as an imine. Suitable nitrogen protecting groups are known to those skilled in the art of organic synthesis and include acyl groups (eg acetyl, trifluoroacetyl), phenyl, benzyl and benzoyl. Other suitable nitrogen protecting groups may be found in *Protective Groups in Organic Synthesis*, T. W. Greene and P. Wutz, John Wiley & Son, 3$^{rd}$ Edition.

The coupling agent used in this first step to form (2) is preferably a nickel or palladium based coupling agent. Suitable coupling agents are known in the art and include $Pd(PPh_3)_2Cl_2$, $Pd(PPh_3)_4$, $Pd(dibenzylideneacetone)_3$ and $PdCl_2(CH_3CN)_2$.

Such coupling reactions are generally performed at temperatures below room temperature, most preferably at 0° C. and below. It is also preferred that such reactions are carried out under an inert atmosphere of either nitrogen or argon. Suitable solvents include ether solvents such as THF and diethyl ether.

The metallated (2) can be reacted, in situ, with Halogen-$R^2$ in the presence of a palladium catalyst in an atmosphere of CO to form (5). This may be accomplished by evacuating the inert reaction gas present in the initial coupling step and replacing said gases with CO. In this system it is also preferred that the initial reaction solvent is replaced with a more polar solvent such as, for instance, DMSO. Removal of the initial reaction solvent may be achieved in vacuo.

The preparation of benzo[b]thiophenes and benzo[b]selenophenes of formula (I) are constructed using a variation of the methods described for the benzo[b]furans and indoles of formula (I) above. In particular, the sulfur or selenium atom, X, must be protected by a suitable protecting group (P) to circumvent competitive coupling of a thiolate or selenoate to the aryl halide to afford xanthones or selenones. Suitable sulfur and selenium protecting groups are those which are capable of sustaining a positive charge. Examples include benzyl, allyl, and alkyl.

As used herein a Hal$^+$ producing agent is an agent which can effectively act as a Hal$^+$ source. Examples of Hal$^+$ producing agents include $I_2$, $Br_2$, $Cl_2$, IBr, ICl, chloroacetamide, iodoacetamide, N-chlorosuccinamide, N-bromosuccinamide and N-iodosuccinamide. Preferably, as shown in Chart 1, the Hal$^+$ producing agent is $I_2$. Cyclisation of (2) can be effected by treating (2) with Hal$^+$ to afford (4). Such reactions may be carried out in a variety of solvents including ionic liquids.

The coupling of (4) with the moiety $M^1$-$R^2$ or $R_2$—C(O)-Hal to produce (5) can be carried out via palladium-mediated coupling and/or metallation techniques as known in the art. For example, lithiation of (4) (e.g. using nBuLi) allows for coupling with $R_2$—C(O)-Hal (Hal is I, Br or Cl, preferably Cl). In another embodiment, a carbonylation reaction can be carried out to access (5) by reacting (4) and $M_2$-$R^2$ with a palladium catalyst in the presence of CO.

Compounds (7) can be prepared by reacting (4) with a phenolate, phenothiolate or phenoselenoate anions or with an appropriately activated aniline in the presence of a base and palladium or copper catalyst. SO, $SO_2$, SeO and $SeO_2$ derivatives can be prepared by controlled oxidation of the corresponding sulphides (i.e., where L=S) and selenides (i.e. where L=Se), respectively.

For the preparation of (6), the coupling of (1) and (8) can be carried out using suitable metallation techniques known in the art (metal exchange for when (1) is halogen, and directed metallation for when (1) is H). For example, the coupling may be carried out in the presence of n-BuLi sec-BuLi, t-BuLi or alkylMghalides such as iPrMgHalide. Cyclisation of (3) using a Hal$^+$ producing agent, e.g. iodocyclization using $I_2$, affords access to (6).

Scheme 2 represents an alternative approach to the compounds of formula (I) of the present invention.

Scheme 2

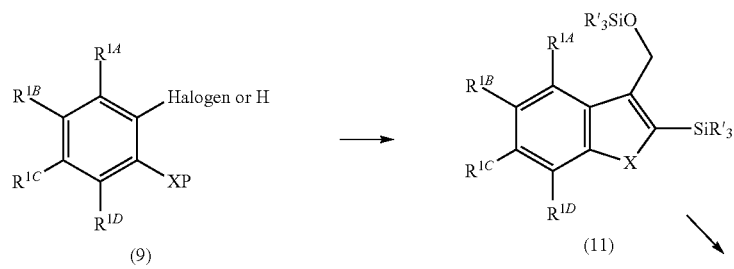

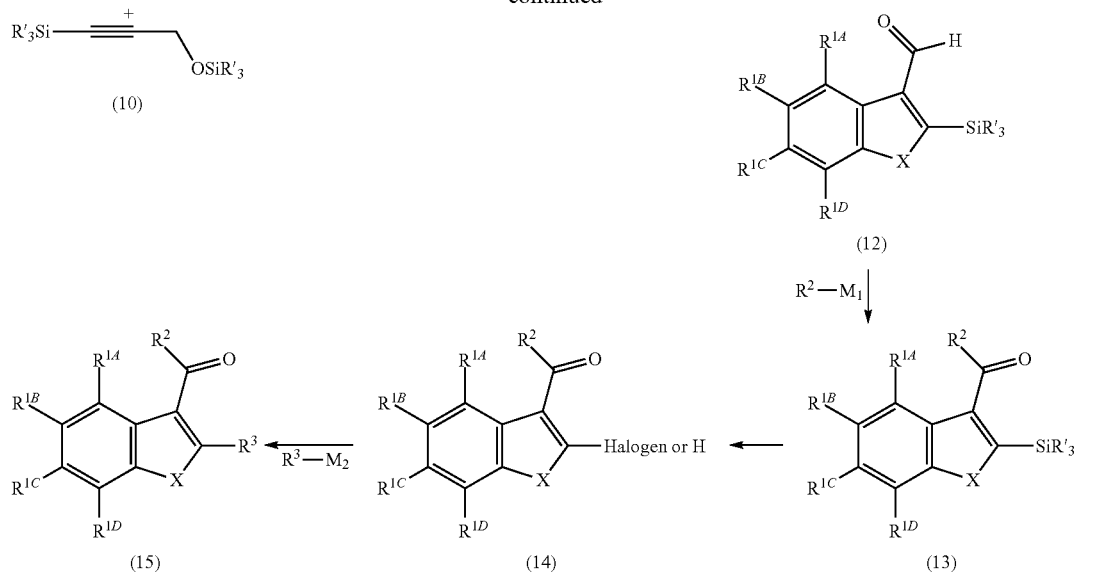

where $R^3$ is an optionally substituted heteroaryl group,
$R^2$ is an optionally substituted aryl group of formula (ii),
X is S, NR, O and Se, and
$R'_3$ is a trialkyl group.

The compounds of formula (I) represented by (15) can alternatively be prepared by palladium coupling compounds (9) with an alkyne (10) to form (11) under the conditions described by Bishop, B. C. et al Synthesis, 1997, 1315. The reaction sequence involves the desilylation and oxidation of the C-3 silyl ether to afford a formyl group (compound (12)). Desilylation can be carried out with the use of either an aqueous acid (for e.g. hydrochloric acid) or by using a fluoride source. Oxidation can be carried out using $CrO_3$, $MnO_2$, dichlorodicyanoquinone (DDQ) or under Swern conditions. Addition of $R^2$-$M_1$ to (12) can be carried out under standard 1,2-addition conditions (for example where $M_1$=Li or Mg) followed by oxidation of the tertiary alcohol to ketone (13). Suitable oxidants include $CrO_3$ (Collins reagent), $MnO_2$, dichorodicyanoquinone (DDQ) or under Swern conditions. Conversion of the C-2 silyl group of (13) to a group suitable for $R^3$ addition can be carried out with ICl, IBr or Br (for when (14) bears a halogen which is I or Br) or TBAF (for when (14) is H).

If the C-2 position bears a suitable halogen, (14) can be reacted with $R^3$-$M_2$ by either Suzuki coupling conditions (e.g. $M_2$=B(OH)$_2$)), Negishi coupling conditions (e.g. $M_2$=Zn), Stille coupling conditions (e.g. $M_2$=Sn(alkyl)$_3$), or other palladium mediated couplings where $M_2$=Cu, Zr, Al. These reactions provide for connection of $R^3$ to the C-2 position of (15) through a C—C bond. Connection of $R^3$ to the C-2 position of (15) through a C—N bond is also possible by direct nucleophilic substitution of a deprotonated heterocyclic N—H or by reaction of the N—H heterocycle with (14) in the presence of a base (e.g. trialkylamine, pyridine, $Na_2CO_3$, $K_2CO_3$, etc).

An important aspect of the present invention relates to compounds which possess tubulin binding activity. In particular it has been found that the introduction of 5- and 6-membered heteroaryl groups into the C2-position of benzofuran, indole, benzothiophene or benzoselenophene based TPIs, can give rise to improved anticancer activity over the same compounds which bear aryl groups at C-2. Furthermore, it has been shown in some cases that this activity can be increased by the introduction of a polar heteroatom in the C-7 position ($R^{1D}$) and even further increased by adding an electron donating group at the C-6 position ($R^{1C}$).

Scheme 3 represents a further approach to the compounds of formula (I) of the present invention.

Scheme 3

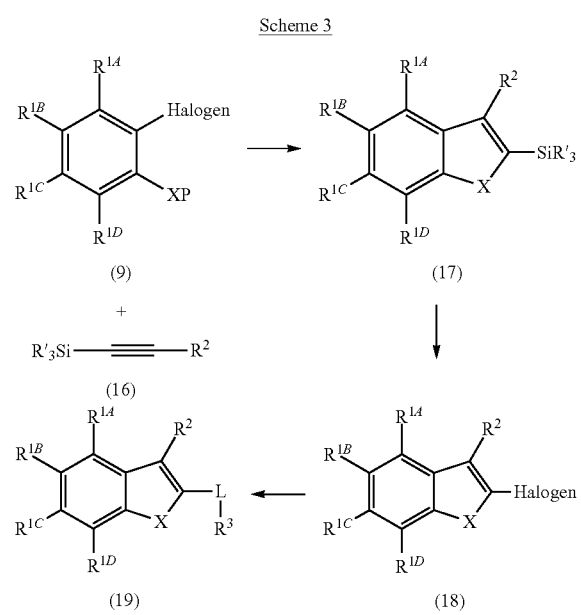

where $R^3$ is an optionally substituted heteroaryl group,
$R^2$ is an optionally substituted aryl group of formula (II),
X is S, NR, O or Se;
L is O, S, Se or NR; and
$R'_3$ is a trialkyl group.

This approach is amenable to the preparation of the compounds of formula (I) where Q is -L-$R^3$. Compound (17) can be prepared by palladium coupling compounds (9) with an alkyne (16) under the conditions discussed previously in relation to the analogous reaction depicted in Scheme 2. Conversion of the C-2 silyl group of (17) to a halogen substituent (18)

can be carried out with ICl, IBr, or $Br_2$. Subsequent coupling of (18) with a L-$R^3$ group may be carried out by reacting (18) with a reactive $^\ominus$O—$R^3$, $^\ominus$S—$R^3$, $^\ominus$Se—$R^3$ anion or with an appropriately activated HN—$R^3$ in the presence of a base and palladium or copper catalyst. Oxidation of the L heteroatom to prepare SO, $SO_2$, SeO, $SeO_2$ can be achieved under the typically applied controlled oxidation conditions known in the art.

As mentioned previously, preferred compounds of the invention having increased tubulin binding activity or anti-tumour vasculature activity, can be useful in methods of therapy. In particular these compounds may be used for treating tumours. As used herein the term "tumour" is used to define any malignant cancerous growth, and may include leukemias, melanomas, colon, lung, ovarian, skin, breast, prostate, CNS, and renal cancers, as well as other cancers.

The compounds of the invention having tubulin binding activity may also be used in the treatment of solid tumours, e.g. breast cancer.

The invention also provides for the use of a compound of formulae (I), (Ia), or (Ib) in the manufacture of a medicament for treating tumours.

There is also provided a method of treatment of solid tumours comprising the administration of an effective amount of a compound of formula (I), (Ia) or (Ib) to a subject in need thereof.

The compounds of the invention may be particularly useful in combination therapy, e.g. combining the treatment with other chemotherapeutic or radiation treatments.

However, it will be understood that the compounds of the invention can be used in the treatment of any disease state for which tubulin polymerisation plays a crucial role.

In particular, the present compounds can be used in treating inflammation. Such inflammatory conditions may include acute and chronic inflammatory conditions such as rheumatoid arthritis, inflammatory bowel disease, Crohn's disease, psoriasis, and the like.

Compounds of the invention which possess bioactivity, such as tubulin binding activity, can be formulated as a composition, particularly a pharmaceutical composition, together with a pharmaceutically acceptable additive.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts e.g. sodium or potassium salts, or alkyl esters (e.g. methyl, ethyl) of the phosphate group.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I) is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group (for instance at the C-7 position or $R^{1D}$) is converted into an ester, such as an acetate or phosphate ester, or where a free amino group is (for instance at the C-7 position or $R^{1D}$) converted into an amide (e.g. α-aminoacid amide). Procedures for esterifying, e.g. acylating, the compounds of the invention are well known in the art and may include treatment of the compound with an appropriate carboxylic acid, anhydride or chloride in the presence of a suitable catalyst or base. A particularly preferred prodrug is a disodium phosphate ester. The disodium phosphate ester of novel compounds of the invention may be useful in targeting tumour vasculature and thus may provide a means of selective delivery of the compounds to the body. The disodium phosphate ester may be prepared in accordance with the methodology described in Pettit, G. R., et al, *Anticancer Drug Des.,* 1995, 10, 299.

The compounds of the invention may be in crystalline form either as the free compounds or as solvates (e.g. hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The synthetic methods and processes described herein to prepare the compounds of the present invention are amenable to solid phase synthetic techniques and/or combinatorial chemistry to produce individual compounds or libraries of compounds.

Traditionally, drug candidates have been synthesised individually, this being a time consuming and laborious process if the synthetic sequence contains even just a few steps and large numbers of compounds are to be evaluated for their biological activity. Combinatorial synthesis is an emerging technique for effecting the generation of large libraries of molecules and has been successfully exploited in the synthesis and evaluation of small organic libraries. These libraries and their starting substrates may exist as molecules in free solution or preferably, linked to a solid support, for example, beads, pins, microtitre plates (wells) or microchips which can be polymeric, glass, silica or other suitable substrate. Chemical diversity can be achieved by either parallel or split (split and mix) syntheses wherein each step has the potential to afford a multitude of compounds. Solution phase libraries may be prepared via parallel syntheses wherein different compounds are synthesised in separate reaction vessels in parallel, often in an automated fashion. Alternatively, attachment of the individual components employed in a synthetic sequence to an appropriate solid phase support allows for the further creation of chemical diversity by utilising not only parallel synthesis but also split synthesis wherein the solid support containing the compounds prepared in the prior step can be split into a number of batches, treated with the appropriate reagent and recombined.

The substrates can be attached to a solid support surface by any linkers known in the art. The linkers may be any component capable of being cleaved to release the substrate or final compound from the support.

Preferably, the solid support is a polymer support. Examples of polymeric supports currently used in solid phase synthesis include: alkenyl resins: e.g. REM resins; BHA resins: e.g. benzhydrylamine (polymer-bound hydrochloride, 2% crosslinked), benzhydryl chloride (polymer bound); Br-functionalised resins: e.g. brominated PPOA resin, brominated Wang resin; Chloromethyl resins: e.g. 4-methoxybenzhydryl chloride (polymer bound); CHO-functionalised resins: e.g. indole resin, formylpolystyrene; Cl-functionalised resins: e.g. Merrifield's resin, chloroacetyl (polymer bound); $CO_2H$-functionalised resins: e.g. carboxypolystyrene; 1-functionalised resins: e.g. 4-iodophenol (polymer bound); Janda Jels™; MBHA resins: e.g. 4-methylbenzhydrylamine hydrochloride (polymer bound), 4-hydroxymethylbenzoic acid-4-methyl benzhydrylamine (polymer bound); Amine-functionalised resins: e.g. (aminomethyl)polystyrene, PAL resin, Sieber amide resin; Nitrophenyl carbonate resins: e.g. 4-nitrophenyl carbonate (polymer bound); OH-functionalised resins: e.g. 4-benzyloxybenzyl alcohol (polymer bound); Hydroxy methyl resins: e.g. benzyl alcohol (polymer bound); HMBA resin; Oxime resins; Rink acid resin; Triazine-based resin; Trityl amine resins; Trityl resins: e.g. trityl-chloride (polymer bound), 2-chlorotrityl alcohol, 1,3-diaminepropane trityl.

Thus, individual compounds or libraries of compounds can be synthesised by initially attaching the first compound substrate to a solid support surface which can be performed by providing a plurality of solid support surfaces, suitably derivatising each of the surfaces with groups capable of reacting with either the compound substrate or a linker moiety attached thereto. The various support surfaces with the attached first compound substrate can then be subjected to various reaction conditions and second compound substrates to provide a library of attached compounds, which may, if necessary, be reacted further with third and subsequent compound substrates or varying reactions conditions. Attachment and detachment of substrates and products can be performed under conditions similar to those as described in Johnson, M. G., et al., *Tetrahedron*, 1999, 55, 11641; Han Y., et al. *Tetrahedron* 1999, 55, 11669; and Collini, M. D., et al., *Tetrahedron Lett.*, 1997, 58, 7963.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Biological Data

TABLE 1

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 1. | 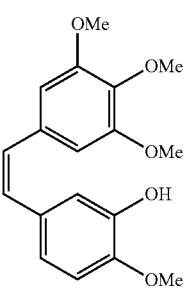 [SMILES: COc1ccc(/C=C\c2cc(OC)c(OC)c(OC)c2)cc1O] | 244.13 | 1.8 ± 0.2 | <10, 2.9 | 1-10 |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 2. | 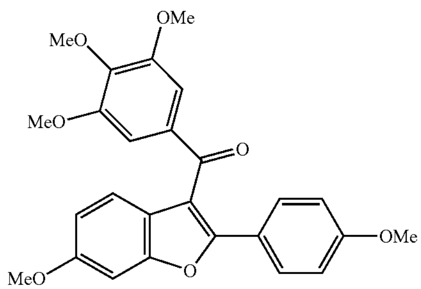 [SMILES: COc1ccc(-c2oc3cc(OC)ccc3c2C(=O)c2cc(OC)c(OC)c(OC)c2)cc1] | 438.12 | 1.5 ± 0.5 | 34 +/− 10 | ND |
| 3. | 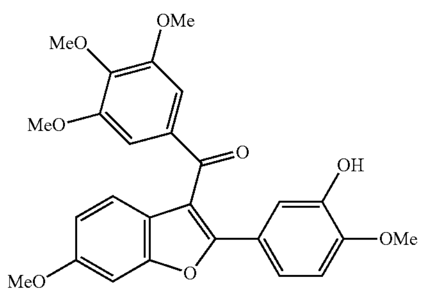 [SMILES: COc1ccc2c(C(=O)c3cc(OC)c(OC)c(OC)c3)c(-c3ccc(OC)c(O)c3)oc2c1] | 464.15 | 1.3 ± 0.1 | 57.21 | ND |
| 4. | 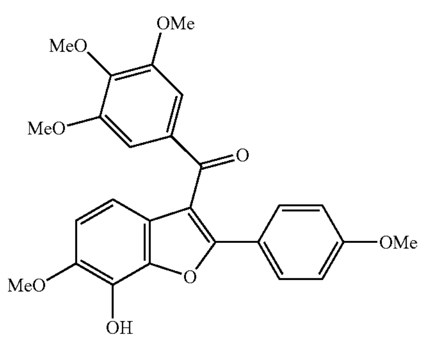 [SMILES: COc1ccc(-c2oc3c(O)c(OC)ccc3c2C(=O)c2cc(OC)c(OC)c(OC)c2)cc1] | 464.46 | 1.5 ± 0.4 | 1-2 | ND |
| 5. | 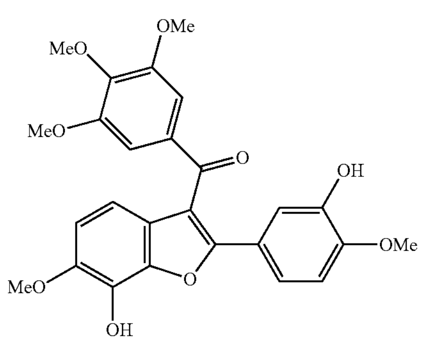 [SMILES: COc1ccc(-c2oc3c(O)c(OC)ccc3c2C(=O)c2cc(OC)c(OC)c(OC)c2)cc1O] | 480.46 | <4 | 3.9, 4.1 | ND |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 6. | (structure) | 342.11 | 1.6 ± 0.2 | 60, 50 | ND |
| 7. | (structure) | 358.35 |  | 62, 31 | 10-100 |
| 8. | (structure) | 588.41 | ND | 3.6, 4.2, 6.0, 4.7 | ND |
| 9. | (structure) | 482.30 | ND | 41; 82 | ND |

TABLE 1-continued

In vitro Data TPIs: These are the results for growth inhibition studies of compounds using the Sulforhodamine B (SRB) or Sysmex cell counting (CC) assays. IC$_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] IC$_{50}$ (μM) | MCF-7, cancer cell line[b] IC$_{50}$ (nM) | Inhib activated HUVECs[c] IC$_{50}$ (nM) |
|---|---|---|---|---|---|
| 10 | 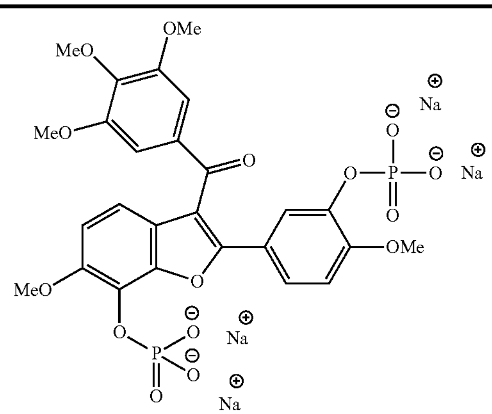 | 728.36 | ND | 5.0, 16 | ND |
| 11 | 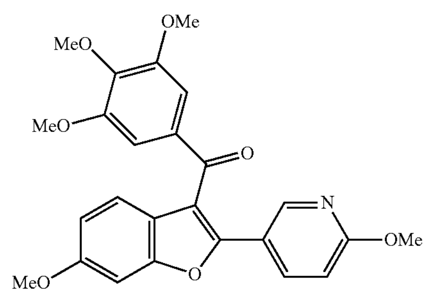 | 449.46 | <4 | 70, 72 | 10-100 |
| 12 | 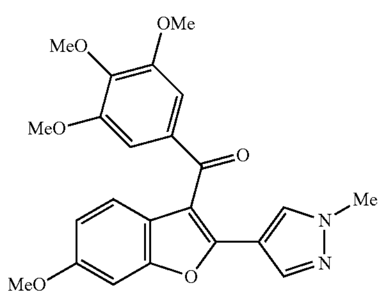 [SMILES: COc1ccc2c(C(=O)c3cc(OC)c(OC)c(OC)c3)c(-c3cnn(C)c3)oc2c1] | 422.44 | 1.2 ± 0.04 | 3.9, 4.0 | 1-10 |
| 13 | 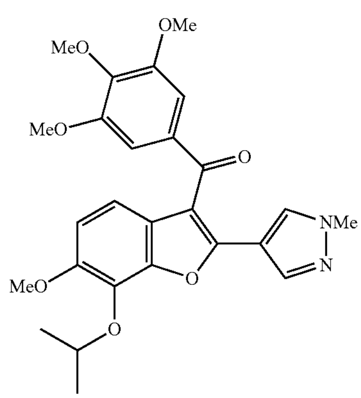 [SMILES: COc1cc(C(=O)c2c(-c3cnn(C)c3)oc3c(OC(C)C)c(OC)ccc23)cc(OC)c1OC] | 480.52 | ND | 48, 35 | ND |

TABLE 1-continued

In vitro Data TPIs: These are the results for growth inhibition studies of
compounds using the Sulforhodamine B (SRB) or Sysmex cell counting (CC) assays. $IC_{50}$
is the concentration required to inhibit net cell growth or tubulin polymerisation by 50%.
Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 14 | 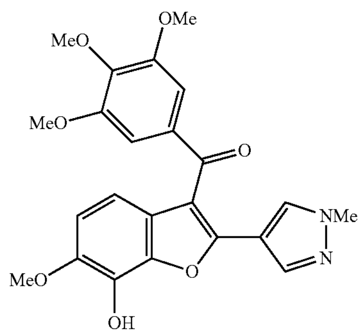 [SMILES: COc1cc(C(=O)c2c(-c3cnn(C)c3)oc3c(O)c(OC)ccc23)cc(OC)c1OC] | 438.44 | 1.3 ± 0.07 | 4, <1[a] | 0.1-1 |
| 15 | 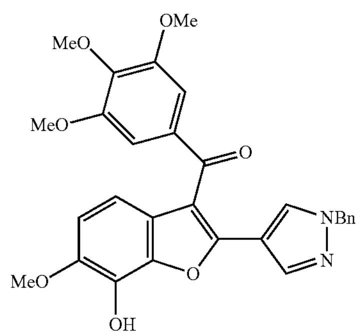 [SMILES: COc1cc(C(=O)c2c(-c3cnn(Cc4ccccc4)c3)oc3c(O)c(OC)ccc23)cc(OC)c1OC] | 514.54 | ND | 4.1, 3.3 | ND |
| 16 | 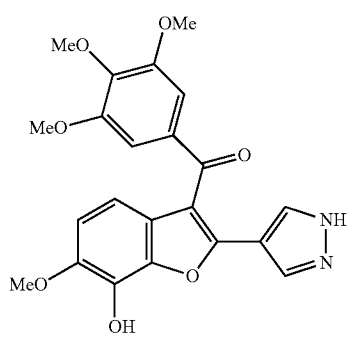 [SMILES: COc1cc(C(=O)c2c(-c3cn[nH]c3)oc3c(O)c(OC)ccc23)cc(OC)c1OC] | 424.41 | ND | 3.0, 3.4 | 1-10 |
| 17 | 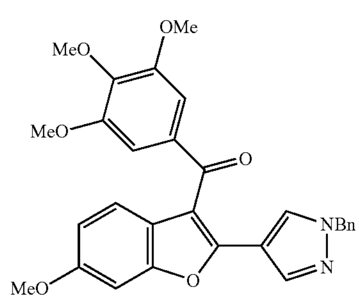 [SMILES: COc1ccc2c(C(=O)c3cc(OC)c(OC)c(OC)c3)c(-c3cnn(Cc4ccccc4)c3)oc2c1] | 498.54 | ND | 110, 83 | 100-1000 |

TABLE 1-continued

*In vitro Data TPIs: These are the results for growth inhibition studies of compounds using the Sulforhodamine B (SRB) or Sysmex cell counting (CC) assays. IC$_{50}$ is the concentration required to inhibit net cell growth or tubulin polymerisation by 50%. Entries 1-10 provided for comparison, entries 11-63 are compounds of the invention.*

| Entry | Structure | Mol w. | Inhib Tubulin polymerisation[a] IC$_{50}$ (μM) | MCF-7, cancer cell line[b] IC$_{50}$ (nM) | Inhib activated HUVECs[c] IC$_{50}$ (nM) |
|---|---|---|---|---|---|
| 18 | 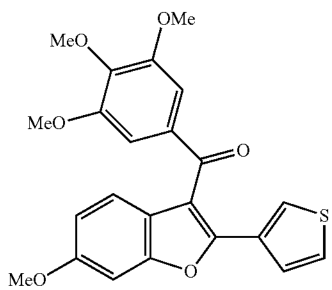 [SMILES: COc1ccc2c(C(=O)c3cc(OC)c(OC)c(OC)c3)c(-c3ccsc3)oc2c1] | 424.48 | ND | 17, 22 | 10-100 |
| 19 | 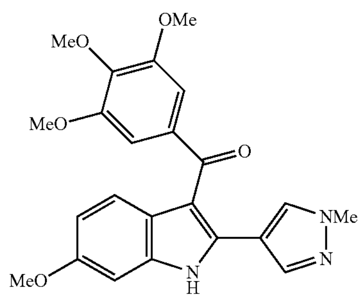 [SMILES: COc1ccc2c(C(=O)c3cc(OC)c(OC)c(OC)c3)c(-c3cnn(C)c3)[nH]c2c1] | 421.46 | ND | 12, 12 | 10-100 |
| 20 | 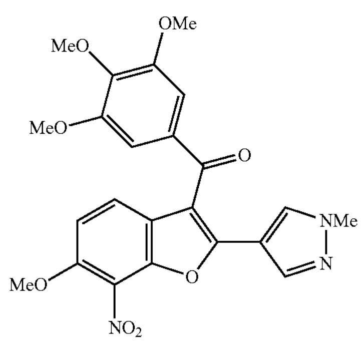 | 467.44 | ND | 33, 40 | 10-100 |
| 21 | 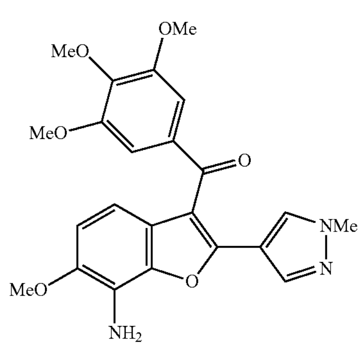 [SMILES: COc1cc(C(=O)c2c(-c3cnn(C)c3)oc3c([N+](=O)[O-])c(OC)ccc23)cc(OC)c1OC] | 437.46 | 1.5 ± 0.1 | <1, 1.2<br><1 | 1-10 |

TABLE 1-continued

In vitro Data TPIs: These are the results for growth inhibition studies of
compounds using the Sulforhodamine B (SRB) or Sysmex cell counting (CC) assays. IC$_{50}$
is the concentration required to inhibit net cell growth or tubulin polymerisation by 50%.
Entries 1-10 provided for comparison, entries 11-63 are compounds of the invention.

| Entry | Structure | Mol w. | Inhib Tubulin polymerisation[a] IC$_{50}$ (μM) | MCF-7, cancer cell line[b] IC$_{50}$ (nM) | Inhib activated HUVECs[c] IC$_{50}$ (nM) |
|---|---|---|---|---|---|
| 22 | 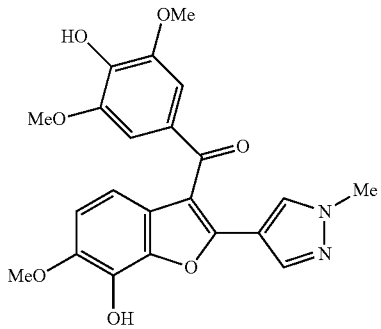 [SMILES: COc1cc(C(=O)c2c(-c3cnn(C)c3)oc3c(O)c(OC)ccc23)cc(OC)c1O] | 424.41 | ND | 25, 29 | ND |
| 23 | 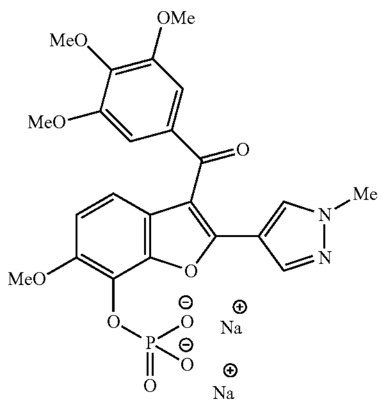 [SMILES: COc1cc(C(=O)c2c(-c3cnn(C)c3)oc3c(OP(=O)([O-])[O-])c(OC)ccc23)cc(OC)c1OC ; [Na+] ; [Na+]] | 562.38 | ND | 3.3; 0.9 | ND |
| 24 | 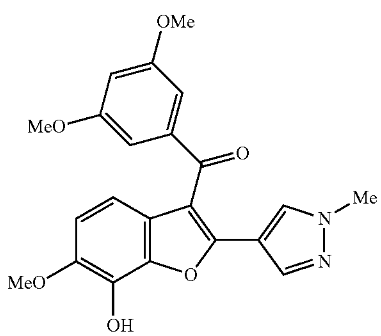 [SMILES: COc1cc(OC)cc(C(=O)c2c(-c3cnn(C)c3)oc3c(O)c(OC)ccc23)c1] | 408.41 | ND | 3.3; 4.4 | 1-10 |
| 25 | 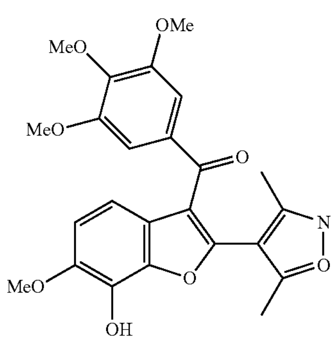 | 453.45 | ND | 68; 57 | 10-100 |

TABLE 1-continued

In vitro Data TPIs: These are the results for growth inhibition studies of
compounds using the Sulforhodamine B (SRB) or Sysmex cell counting (CC) assays. $IC_{50}$
is the concentration required to inhibit net cell growth or tubulin polymerisation by 50%.
Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 26 | 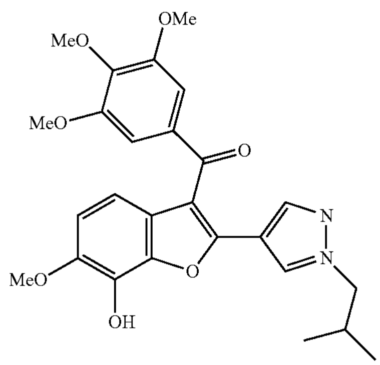 | 480.52 | ND | 21; 14 | 1-10 |
| 27 | 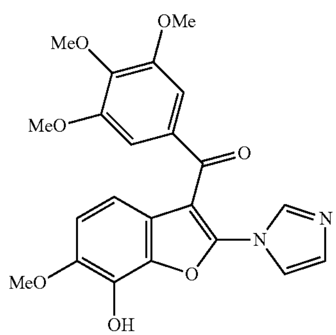 [SMILES: COc1cc(C(=O)c2c(-n3ccnc3)oc3c(O)c(OC)ccc23)cc(OC)c1OC] | 424.41 | ND | 1.6; <1 | 1-10 |
| 28 | 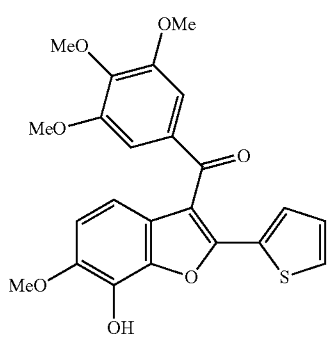 [SMILES: COc1cc(C(=O)c2c(-c3cccs3)oc3c(O)c(OC)ccc23)cc(OC)c1OC] | 440.48 | ND | <1; <1 | 0.1-1 |
| 29 | 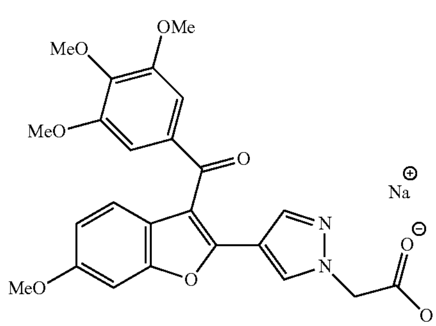 | 488.44 | ND | 900; 540 | 100-100 |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 30 | 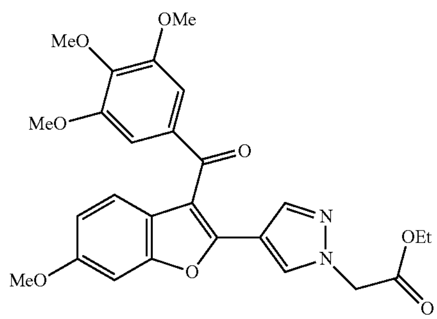 | 494.51 | ND | 29; 15 | 10-100 |
| 31 | 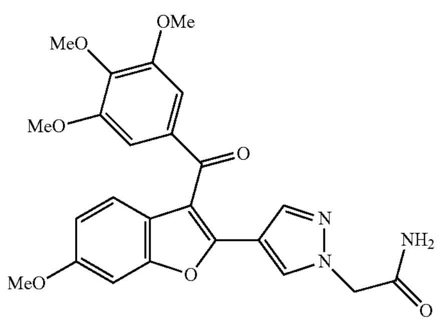 [SMILES: COc1ccc2c(C(=O)c3cc(OC)c(OC)c(OC)c3)c(-c3cnn(CC(N)=O)c3)oc2c1] | 465.47 | ND | 3.8; 4.0 | 1-10 |
| 32 | 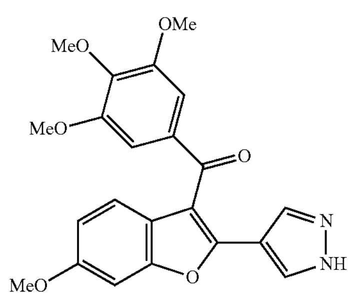 [SMILES: COc1ccc2c(C(=O)c3cc(OC)c(OC)c(OC)c3)c(-c3cn[nH]c3)oc2c1] | 408.42 | ND | 3.6; 4.0 | 1-10 |
| 33 | 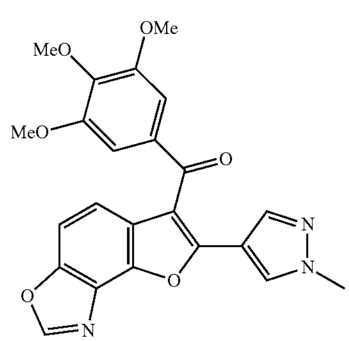 [SMILES: COc1cc(C(=O)c2c(-c3cnn(C)c3)oc3c2ccc2ocnc23)cc(OC)c1OC] | 433.42 | ND | 540; 600 | 100-1000 |

TABLE 1-continued

In vitro Data TPIs: These are the results for growth inhibition studies of
compounds using the Sulforhodamine B (SRB) or Sysmex cell counting (CC) assays. $IC_{50}$
is the concentration required to inhibit net cell growth or tubulin polymerisation by 50%.
Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 34 | 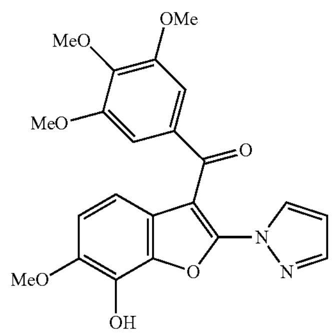 [SMILES: COc1cc(C(=O)c2c(-n3cccn3)oc3c(O)c(OC)ccc23)cc(OC)c1OC] | 424.41 | ND | 3.5; 2.4 | 100-1000 |
| 35 | 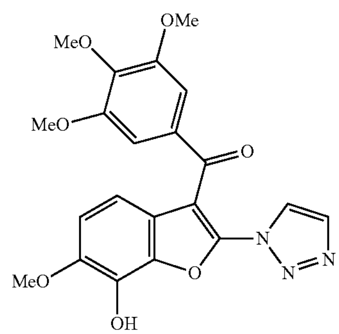 [SMILES: COc1cc(C(=O)c2c(-n3ccnn3)oc3c(O)c(OC)ccc23)cc(OC)c1OC] | 425.40 | | 0.42; 1.7 | 1-10 |
| 36 | 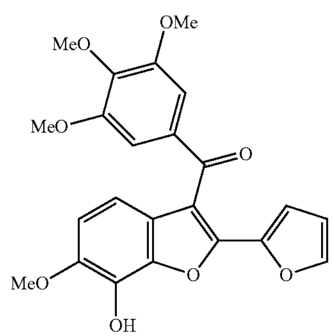 [SMILES: COc1cc(C(=O)c2c(-c3ccco3)oc3c(O)c(OC)ccc23)cc(OC)c1OC] | 424.41 | 8.7 ± 0.8 | 0.33; 0.75 | 1-10 |
| 37 | 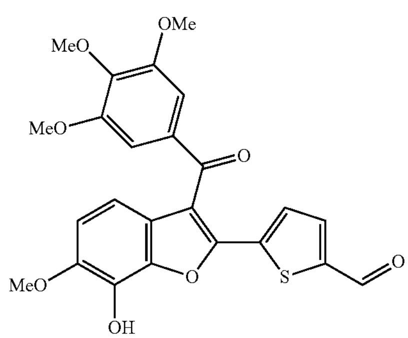 [SMILES: COc1cc(C(=O)c2c(-c3ccc(C=O)s3)oc3c(O)c(OC)ccc23)cc(OC)c1OC] | 468.49 | ND | 1.8; 2.3 | 1-10 |

TABLE 1-continued

In vitro Data TPIs: These are the results for growth inhibition studies of compounds using the Sulforhodamine B (SRB) or Sysmex cell counting (CC) assays. IC$_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] IC$_{50}$ (μM) | MCF-7, cancer cell line[b] IC$_{50}$ (nM) | Inhib activated HUVECs[c] IC$_{50}$ (nM) |
|---|---|---|---|---|---|
| 38 | 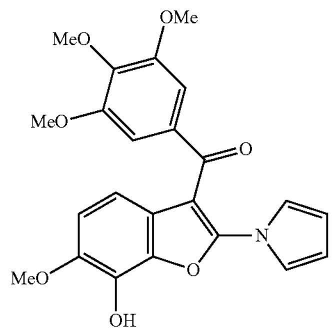 [SMILES: COc1cc(C(=O)c2c(-n3cccc3)oc3c(O)c(OC)ccc23)cc(OC)c1OC] | 423.43 | ND | 1.4; 2.1 | 1-10 |
| 39 | 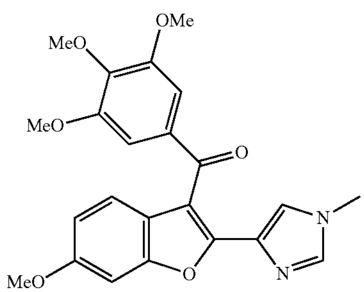 [SMILES: COc1ccc2c(C(=O)c3cc(OC)c(OC)c(OC)c3)c(-c3cn(C)cn3)oc2c1] | 422.15 | ND | 40; 35 | 10-100 |
| 40 | 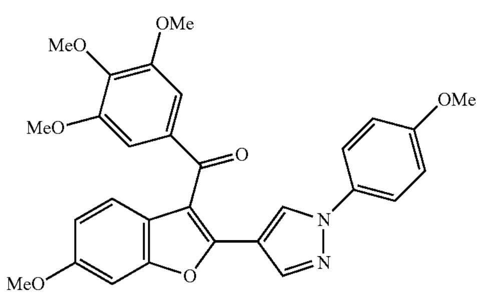 [SMILES: COc1ccc(-n2cc(-c3oc4cc(OC)ccc4c3C(=O)c3cc(OC)c(OC)c(OC)c3)cn2)cc1] | 514.53 | ND | 360; 350 | 100-1000 |
| 41 | 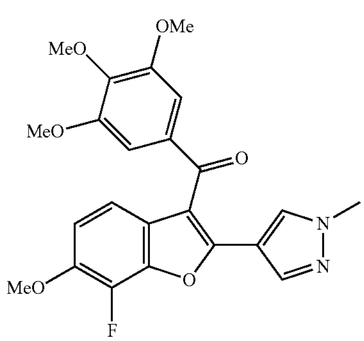 [SMILES: COc1cc(C(=O)c2c(-c3cnn(C)c3)oc3c(F)c(OC)ccc23)cc(OC)c1OC] | 440.43 | ND | 4.2; 3.6 | 1-10 |

TABLE 1-continued

*In vitro Data TPIs: These are the results for growth inhibition studies of compounds using the Sulforhodamine B (SRB) or Sysmex cell counting (CC) assays. IC$_{50}$ is the concentration required to inhibit net cell growth or tubulin polymerisation by 50%. Entries 1-10 provided for comparison, entries 11-63 are compounds of the invention.*

| Entry | Structure | Mol w. | Inhib Tubulin polymerisation[a] IC$_{50}$ (µM) | MCF-7, cancer cell line[b] IC$_{50}$ (nM) | Inhib activated HUVECs[c] IC$_{50}$ (nM) |
|---|---|---|---|---|---|
| 42 | 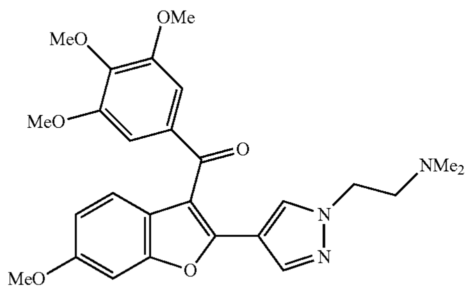 [SMILES: COc1ccc2c(C(=O)c3cc(OC)c(OC)c(OC)c3)c(-c3cnn(CCN(C)C)c3)oc2c1] | 479.52 | ND | 300; 310 | 100-1000 |
| 43 | 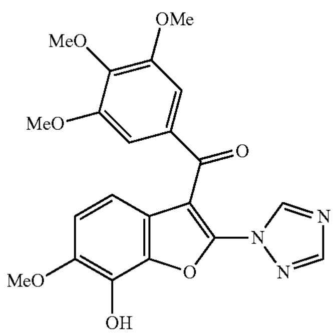 | 425.39 | ND | 0.37; 0.32 | 0.1-1 |
| 44 | 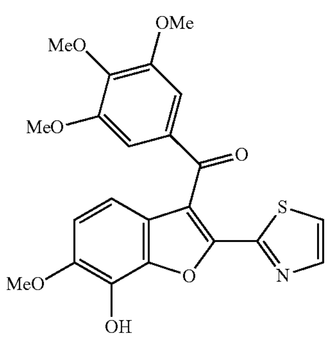 [SMILES: COc1cc(C(=O)c2c(-c3nccs3)oc3c(O)c(OC)ccc23)cc(OC)c1OC] | 441.45 | 2.2 ± 0.4 | 0.37; 0.32 | 0.1-1 |
| 45 | 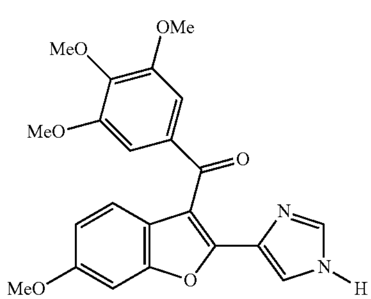 [SMILES: COc1ccc2c(C(=O)c3cc(OC)c(OC)c(OC)c3)c(-c3c[nH]cn3)oc2c1] | 408.40 | ND | 4.5; 5.7 | 1-10 |

TABLE 1-continued

In vitro Data TPIs: These are the results for growth inhibition studies of compounds using the Sulforhodamine B (SRB) or Sysmex cell counting (CC) assays. IC$_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation$^a$ IC$_{50}$ (μM) | MCF-7, cancer cell line$^b$ IC$_{50}$ (nM) | Inhib activated HUVECs$^c$ IC$_{50}$ (nM) |
|---|---|---|---|---|---|
| 46 | 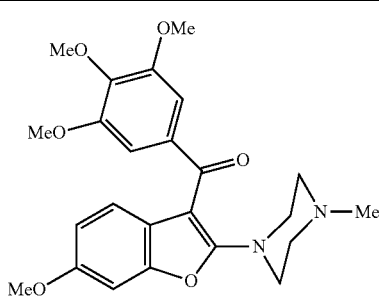 | 440.5 | ND | 200, 230 | 100-1000 |
| 47 | 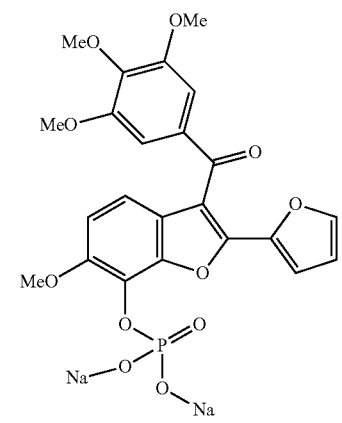 | 548.34 | ND | 0.26, 0.31 | ND |
| 48 | 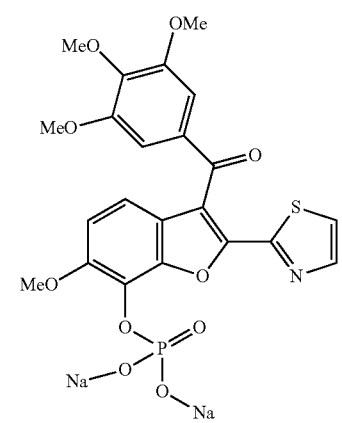 | 565.40 | ND | 0.53, 0.40 | ND |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (µM) | MCF-7, cancer cell line[b] $IC_{50}$ (nM) | Inhib activated HUVECs[c] $IC_{50}$ (nM) |
|---|---|---|---|---|---|
| 49 | 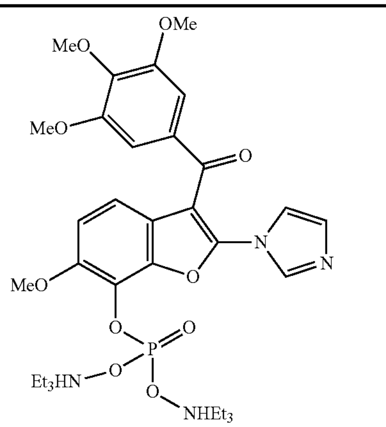 | 706.76 | ND | 1.4, 2.2 | ND |
| 50 | 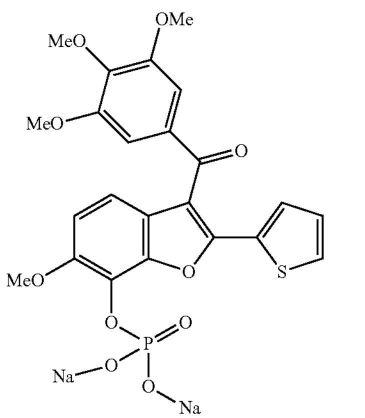 | 564.41 | ND | 0.69, 0.33 | ND |
| 51 | 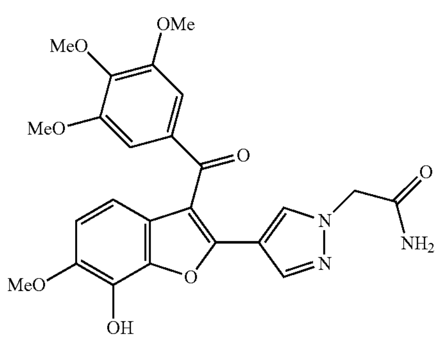 [SMILES: COc1cc(C(=O)c2c(-c3cnn(CC(N)=O)c3)oc3c(O)c(OC)ccc23)cc(OC)c1OC] | 481.45 | ND | 1.5, 0.62 | 0.1-1 |
| 52 | 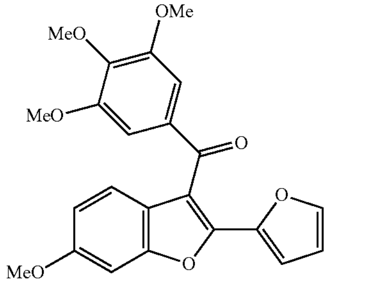 [SMILES: COc1ccc2c(C(=O)c3cc(OC)c(OC)c(OC)c3)c(-c3ccco3)oc2c1] | 408.40 | ND | 6.9, 7.9 | 1-10 |

TABLE 1-continued

In vitro Data TPIs: These are the results for growth inhibition studies of
compounds using the Sulforhodamine B (SRB) or Sysmex cell counting (CC) assays. $IC_{50}$
is the concentration required to inhibit net cell growth or tubulin polymerisation by 50%.
Entries 1-10 provided for comparison, entries 11-63 are compounds of the invention.

| Entry | Structure | Mol w. | Inhib Tubulin polymerisation[a] $IC_{50}$ (μM) | MCF-7, cancer cell line[b] $IC_{50}$ (nM) | Inhib activated HUVECs[c] $IC_{50}$ (nM) |
|---|---|---|---|---|---|
| 53 | 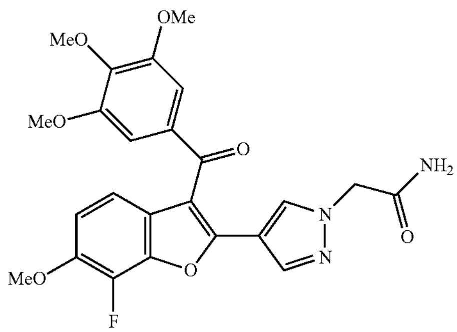 [SMILES: COc1cc(C(=O)c2c(-c3cnn(CC(N)=O)c3)oc3c(F)c(OC)ccc23)cc(OC)c1OC] | 483.46 | ND | 7.8, 8.1 | 0.1-1 |
| 54 | 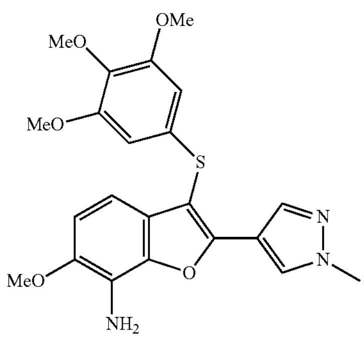 [SMILES: COc1cc(Sc2c(-c3cnn(C)c3)oc3c(N)c(OC)ccc23)cc(OC)c1OC] | 441.51 | ND | 0.1-1.0 | 1-10 |
| 55 | 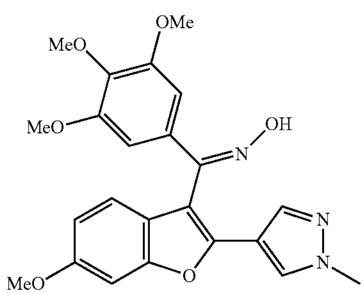 [SMILES: COc1ccc2c(/C(=N/O)c3cc(OC)c(OC)c(OC)c3)c(-c3cnn(C)c3)oc2c1] | 437.46 | ND | 100-1000 | 100-1000 |
| 56 | 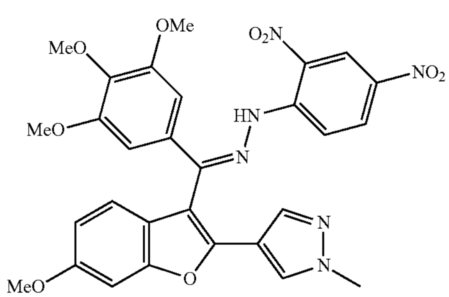 [SMILES: COc1ccc2c(/C(=N/Nc3ccc([N+](=O)[O-])cc3[N+](=O)[O-])c3cc(OC)c(OC)c(OC)c3)c(-c3cnn(C)c3)oc2c1] | 602.57 | ND | >1000 | 100-1000 |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (µM) | MCF-7, cancer cell line[b] $IC_{50}$ (nM) | Inhib activated HUVECs[c] $IC_{50}$ (nM) |
|---|---|---|---|---|---|
| 57 | 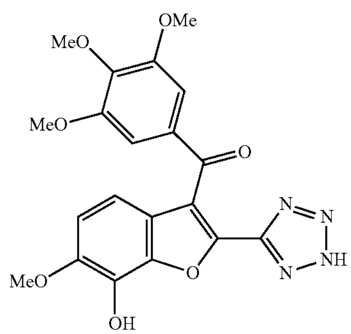 | 426.39 | ND | 10-100 | 10-100 |
| 58 | 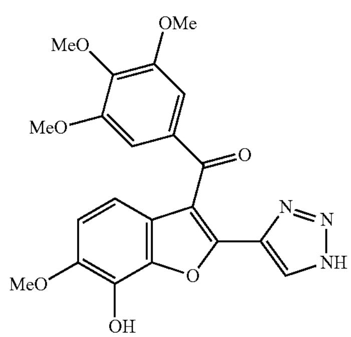 | 425.40 | ND | 1-10 | 1-10 |
| 59 | 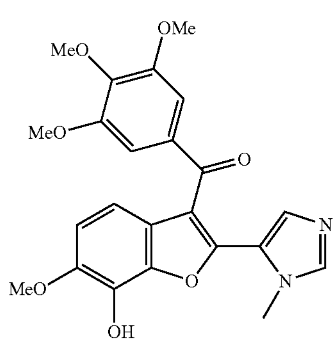 [SMILES: COc1cc(C(=O)c2c(-c3cncn3C)oc3c(O)c(OC)ccc23)cc(OC)c1OC] | 438.43 | ND | 1-10 | 1-10 |

TABLE 1-continued

In vitro Data TPIs: These are the results for growth inhibition studies of compounds using the Sulforhodamine B (SRB) or Sysmex cell counting (CC) assays. $IC_{50}$ is the concentration required to inhibit net cell growth or tubulin polymerisation by 50%. Entries 1-10 provided for comparison, entries 11-63 are compounds of the invention.

| Entry | Structure | Mol w. | Inhib Tubulin polymerisation[a] $IC_{50}$ (µM) | MCF-7, cancer cell line[b] $IC_{50}$ (nM) | Inhib activated HUVECs[c] $IC_{50}$ (nM) |
|---|---|---|---|---|---|
| 60 | (structure) | 556.0 | ND | ND | ND |
| 61 | (structure) | 739.64 | | | |

[a] The tubulin concentration was 10 µM. Inhibition of extent of assembly, after a 20 min incubation at 30 °C., was the parameter measured: For a description of the method see Verdier-Pinard, P. et. al. *Mol. Pharmacol.* 1998, 53, 62-76.

[b] For a description of the method of MCF-7 inhibition see: Verdier-Pinard, P. et. al. *Mol. Pharmacol.* 1998, 53, 62-76. For entries 59-60 the cell line was MDA-MB-231 and values are given as a range within which the $IC_{50}$ value falls, for the method see Biological methods, below

[c] The value is given as a range within which the $IC_{50}$ values falls. For a description of the method used see Biological Methods, below.

Synthetic Protocols

Example 1

A series of compounds of the invention were prepared by carbonylative multicomponent coupling (see Scheme 1).

General Procedure for Carbonylative Multicomponent Coupling

To a solution of iodophenol (1 eq) and alkyne (1.2 eq) in dry THF (5 mL/mmol) under nitrogen at 0° C. was added methyl magnesium chloride (solution in THF, 2.5 eq) and the reaction allowed to warm to room temperature. After stirring for 10 minutes, Pd(Ph$_3$P)$_2$Cl$_2$ (5 mol %) was added and the reaction heated to 65° C. for 4-8 h (tlc). The THF was removed under vacuum and replaced with DMSO (12 mL/mmol) and the nitrogen atmosphere was replaced with carbon monoxide. The aryl iodide (1.05 eq) was added and the reaction heated to 90-100° C. overnight then quenched with 10% NH$_4$Cl$_{(aq)}$ and extracted with ethyl acetate. The organic layer was washed with brine and the solvent removed under vacuum. The residue was concentrated onto silica gel and purified by flash column chromatography.

a) Preparation of 6-Methoxy-2-(1H-pyrazol-4-yl)-3-(3,4,5-trimethoxybenzoyl)benzo[b]furan (entry 32, Table 1)

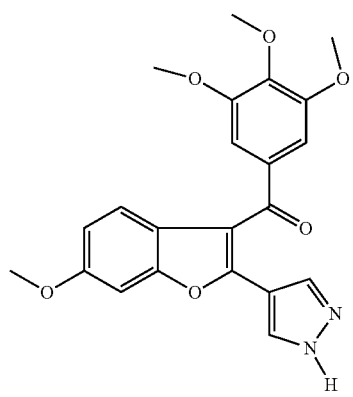 [SMILES: COc1ccc2c(C(=O)c3cc(OC)c(OC)c(OC)c3)c(-c3cn[nH]c3)oc2c1]

(i) 4-Iodo-1-(4-methoxy-benzyl)-1H-pyrazole

To a stirred solution of 4-iodo-1H-pyrazole (1.50 g, 7.73 mmol) in dry DMF (15 mL) at 0° C. was added sodium hydride (9.28 mmol, 60% dispersion in mineral oil) and the reaction mixture was allowed to warm to room temperature. After the evolution of hydrogen had ceased, 4-methoxy-benzyl chloride (1.06 mL, 7.80 mmol) was added and the reaction was stirred for 2 h and then quenched with water (50 mL) and extracted with diethyl ether (100 mL). The organic layer was washed with water (3×30 mL) and brine, dried over magnesium sulphate and the solvent removed under vacuum. The crude residue was washed with small portions of hexane and dried in vacuo, providing the product as a white solid (2.26 g, 93% yield). $^1$H-NMR (CDCl$_3$) δ 7.51 (s, 1H), 7.34 (s, 1H), 7.17 (d, J=8.5 Hz, 2H), 6.87 (d, J=8.5 Hz, 2H), 5.21 (s, 2H), 3.78 (s, 3H).

(ii) 4-Ethynyl-1-(4-methoxy-benzyl)-1H-pyrazole

A vigorously stirred solution of 4-iodo-1-(4-methoxy-benzyl)-1H-pyrazole (1.0 g, 3.18 mmol) and Pd(Ph$_3$P)$_2$Cl$_2$ (60 mg, 3 mol %) in a mixture of DCM (10 mL) and triethylamine (3 mL) was evacuated and backfilled with nitrogen three times and then treated sequentially with trimethylsilylacetylene (0.53 mL, 3.83 mmol) and copper (I) iodide (70 mg, 12 mol %). The reaction rapidly became dark and after stirring for 3 h the solvents were removed in vacuo and the residue treated with methanol (10 mL) and potassium hydroxide (300 mg, 5.35 mmol). After stirring for 30 minutes the mixture was concentrated onto silica gel and purified by flash column chromatography (eluent-hexane:diethyl ether 2:1) to afford the title compound as a white solid (550 mg, 81% yield over two steps). $^1$H-NMR (CDCl$_3$) δ 7.61 (s, 1H), 7.46 (s, 1H), 7.17 (d, J=8.6 Hz, 2H), 6.86 (d, J=8.6 Hz, 2H), 5.18 (s, 2H), 3.78 (s, 3H), 2.96 (s, 1H).

(iii) 6-Methoxy-2-(1-(4-methoxybenzyl)-1H-pyrazol-4-yl)-3-(3,4,5-trimethoxybenzoyl)benzo[b]furan This compound was prepared by application of the general procedure to 2-iodo-5-methoxy-phenol, 4-ethynyl-1-(4-methoxy-benzyl)-1H-pyrazole and 3,4,5-trimethoxy-iodobenzene. The crude product was stirred with potassium carbonate (excess) in methanol for 3 h to hydrolyse ester by-products and submitted to silica-gel flash chromatography (eluent=2:1 hexanes:ethyl acetate) to afford a mixture of the title compound and the corresponding non-carbonyl inserted derivative. This mixture was used directly in the subsequent deprotection. An analytical sample was purified by recrystallisation from dichloromethane/hexane. $^1$H-NMR (CDCl$_3$) δ 8.03 (s, 1H), 8.01 (s, 1H), 7.18 (d, J=8.6 Hz, 2H), 7.14 (d, J=8.7 Hz, 1H), 7.10 (s, 2H), 7.02 (d, J=2.2 Hz, 1H), 6.86 (d, J=8.6 Hz, 2H), 6.79 (dd, J=8.7, 2.2 Hz, 1H), 5.22 (s, 2H), 3.92 (s, 3H), 3.85 (s, 3H), 3.78 (s, 3H), 3.75 (s, 6H). $^{13}$C-NMR (CDCl$_3$) δ 190.2, 159.5, 158.1, 154.2, 153.3, 152.9, 142.3, 139.1, 133.6, 129.8, 129.3, 127.6, 121.7, 120.9, 114.2, 113.8, 112.9, 112.2, 107.0, 95.5, 60.9, 56.1, 55.8, 55.6, 55.2.

(iv) 6-Methoxy-2-(1H-pyrazol-4-yl)-3-(3,4,5-trimethoxybenzoyl)benzo[b]furan

The mixture from the multicomponent coupling was dissolved in trifluoroacetic acid (5 mL/200 mg) and shaken overnight in a sealed tube at 65° C. The solvent was removed by passing a stream of air over the contents of the flask and the product was purified by flash chromatography (silica gel, sequential elution-2:1 hexanes:ethyl acetate, 1:1) to give the product as a pale yellow resin that was solidified by freeze-drying in t-butanol. Yield=29% over two steps. $^1$H-NMR (CDCl$_3$) δ 8.27 (br s, 1H), 7.77 (br s, 1H), 7.15 (d, J=8.6 Hz, 1H), 7.14 (s, 2H), 7.05 (d, J=2.2 Hz, 1H), 6.80 (dd, J=8.6, 2.2 Hz, 1H), 3.92 (s, 3H), 3.85 (s, 3H), 3.76 (s, 6H).

b) Preparation of [2-(1-Benzyl-1H-pyrazol-4-yl)-6-methoxy-benzofuran-3-yl]-(3,4,5-trimethoxyphenyl)-methanone (entry 17, Table 1)

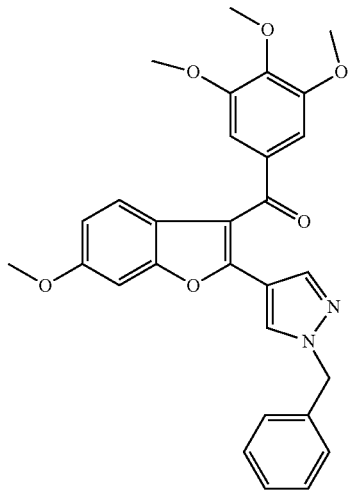 [SMILES: COc1ccc2c(C(=O)c3cc(OC)c(OC)c(OC)c3)c(-c3cnn(Cc4ccccc4)c3)oc2c1]

(i) 1-Benzyl-4-iodo-1H-pyrazole

To a stirred suspension of 4-iodo-1H-pyrazole (1.50 g, 7.73 mmol) and potassium carbonate (2.67 g, 19.3 mmol) in acetone was added benzyl bromide (0.96 mL, 8.07 mmol) and the reaction was refluxed for 3 h. After cooling to room temperature the mixture was concentrated onto silica gel in vacuo and eluted through a short silica plug (sequential elution-hexane, 10% diethyl ether in hexanes) to provide the title compound as a white solid (2.12 g, 97% yield).
Literature reference—Tetrahedron Letters, 2001, p 863.

(ii) 1-Benzyl-4-ethynyl-1H-pyrazole

This compound was prepared from 1-benzyl-4-iodo-1H-pyrazole using a similar procedure to that employed in the preparation of 4-ethynyl-1-(4-methoxy-benzyl)-1H-pyrazole (see a)(ii) above). The reaction time was extended to 5 h and 1.6 equivalents of trimethylsilylacetylene were added. Silica-gel flash chromatography of the crude reaction mixture afforded the product as a white solid (83% yield over two steps).
$^1$H-NMR (CDCl$_3$) δ 7.63 (s, 1H), 7.50 (s, 1H), 7.37-7.28 (m, 3H), 7.22-7.19 (m, 2H), 5.26 (s, 2H), 2.97 (s, 1H).

(iii) [2-(1-Benzyl-1H-pyrazol-4-yl)-6-methoxy-benzofuran-3-yl]-(3,4,5-trimethoxyphenyl)-methanone This compound was prepared by application of the general procedure to 2-iodo-5-methoxy-phenol, 1-benzyl-4-ethynyl-1H-pyrazole and 3,4,5-trimethoxy-iodo-benzene. The crude product was stirred with potassium carbonate (excess) in methanol to hydrolyse ester by-products and submitted to silica-gel flash chromatography (eluent=2:1 hexanes:ethyl acetate) to afford the title compound as a yellow resin that crystallised after trituration in diethyl ether (31% yield). An analytical sample was obtained by preparative thin layer chromatography (eluent=2:1 hexane:ethyl acetate). $^1$H-NMR (CDCl$_3$) δ 8.10 (s, 1H), 8.03 (s, 1H), 7.36-7.21 (m, 5H), 7.13 (d, J=8.7 Hz, 1H), 7.11 (s, 2H), 7.03 (d, J=2.0 Hz, 1H), 6.79 (dd, J 8.7, 2.0 Hz, 1H), 5.29 (s, 2H), 3.92 (s, 3H), 3.85 (s, 3H), 3.75 (s, 6H). $^{13}$C-NMR (CDCl$_3$) δ 190.3, 158.2, 154.3, 153.3, 153.0, 142.4, 139.3, 135.7, 133.7, 130.3, 128.9, 128.3, 127.8, 121.8, 120.9, 114.0, 113.1, 112.3, 107.1, 95.6, 61.1, 56.4, 56.3, 55.8.

c) Preparation of [7-Hydroxy-6-methoxy-2-(1H-pyrazol-4-yl)-benzofuran-3-yl]-(3,4,5-trimethoxyphenyl)-methanone (entry 16, Table 1)

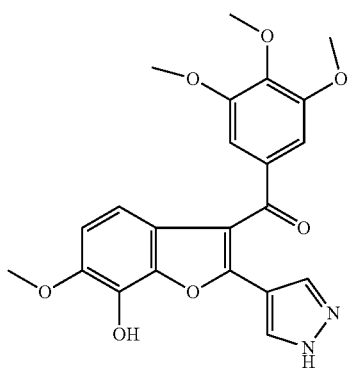 [SMILES: COc1cc(C(=O)c2c(-c3cn[nH]c3)oc3c(O)c(OC)ccc23)cc(OC)c1OC]

(i) 2-Benzyloxy-3-methoxy-6-iodo-phenol

To a suspension of 2-benzyloxy-3-methoxy-phenol (3.80 g, 16.5 mmol) and cupric acetate monohydrate (3.28 g, 16.5 mmol) in acetic acid (45 mL) was added iodine (4.62 g, 18.2 mmol) and the reaction was heated to 55° C. and stirred overnight. After this time the reaction was quenched with 10% aqueous sodium thiosulphate (40 mL) and diluted with diethyl ether (150 mL). The resultant emulsion was filtered through celite and the organic layer was washed with water (4×40 mL) and brine (40 mL), dried over magnesium sulphate and the solvent removed under vacuum. The crude residue was purified by silica-gel flash chromatography (sequential elution—5% diethyl ether in hexane, 10%). Concentration of fractions containing the pure product as indicated by thin layer chromatography gave 2.85 g of the desired product. Later impure fractions were combined and re-chromatographed to yield a further 520 mg of material (combined mass=3.37 g, 57% yield). $^1$H-NMR (CDCl$_3$) δ 7.40-7.33 (m, 5H), 7.34 (d, J=8.9 Hz, 1H), 6.34 (d, J=8.9 Hz, 1H), 6.06 (s, 1H), 5.06 (s, 2H), 3.86 (s, 3H).

(ii) [2-(1-Benzyl-1H-pyrazol-4-yl)-7-hydroxy-6-methoxy-benzofuran-3-yl]-(3,4,5-trimethoxyphenyl)-methanone Application of the general procedure to 2-benzyloxy-6-iodo-3-methoxy-phenol, 1-benzyl-4-ethynyl-1H-pyrazole and 3,4,5-trimethoxy-iodo-benzene (NB—the initial coupling proceeded slowly and was continued overnight) and silica-gel flash chromatography (eluent=40% ethyl acetate in hexane) gave a mixture of the title compound, [2-(1-benzyl-1H-pyrazol-4-yl)-7-benzyloxy-6-methoxy-benzofuran-3-yl]-(3,4,5-trimethoxyphenyl)-methanone and the corresponding non-carbonyl inserted derivative. This mixture was again subjected to silica-gel flash chromatography (sequential elution—2% diethyl ether in DCM, 10%). Concentration of the first eluted fractions afforded a mixture of the 7-benzyloxy derivative and the non-carbonyl inserted material and was used in subsequent chemistry. The later fractions gave the title compound (2% yield) as a pale yellow solid. An analytical sample was obtained by recrystallisation from DCM and hexane. $^1$H-NMR (CDCl$_3$) δ 8.08 (s, 1H), 8.03 (s, 1H), 7.36-7.27 (m, 3H), 7.22-7.19 (m, 2H), 7.10 (s, 2H), 6.80 (d, J=8.6 Hz, 1H), 6.74 (d, J=8.6 Hz, 1H), 5.28 (s, 2H), 3.92 (s, 3H), 3.91 (s, 3H), 3.74 (s, 6H).

(iii) [7-Hydroxy-6-methoxy-2-(1H-pyrazol-4-yl)-benzofuran-3-yl]-(3,4,5-trimethoxyphenyl)-methanone A suspension of crude [2-(1-benzyl-1H-pyrazol-4-yl)-7-benzyloxy-6-methoxy-benzofuran-3-yl]-(3,4,5-trimethoxyphenyl)-methanone (29 mg), 10% palladium on carbon (20 mg) and 6M HCl$_{(aq)}$ (2 drops) in ethyl acetate (2 mL) and methanol (1 mL) was stirred at room temperature overnight. After this time the reaction mixture was filtered through celite and the solvent removed under vacuum. The crude residue was purified by preparative thin layer chromatography to afford the product as a pale yellow resin that was solidified by freeze-drying with t-butanol (5 mg, 2% over two steps).

$^1$H-NMR (CDCl$_3$) δ 7.55 (br s, 2H), 7.15 (s, 1H), 7.14 (d, J=8.8 Hz, 1H), 6.95 (d, J=8.8 Hz, 1H), 3.94 (s, 3H), 3.88 (s, 3H), 3.79 (s, 6H).

d) Preparation of [2-(1H-Imidazol-4-yl)-6-methoxy-benzofuran-3-yl]-(3,4,5-trimethoxyphenyl)-methanone (entry 45, Table 1)

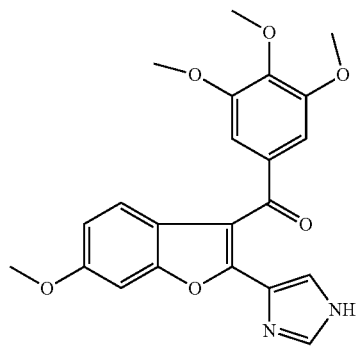 [SMILES: COc1ccc2c(C(=O)c3cc(OC)c(OC)c(OC)c3)c(-c3c[nH]cn3)oc2c1]

(i) 4-Iodo-1-trityl-1H-imidazole

This compound was prepared in 3 steps from imidazole by application of literature procedures (J. Chem. Soc. Perkins Trans 1, 1983 p 735; Biochemistry, 1967 p 17; J. Heterocyclic Chem. 1985, p 57).

(ii) 4-Ethynyl-1-trityl-1H-imidazole

To a stirred solution of 4-iodo-1-trityl-1H-imidazole (830 mg, 1.96 mmol) and Pd(Ph$_3$P)$_2$Cl$_2$ (40 mg, 3 mol %) in THF (8 mL) and triethylamine (2 mL) was added 2-methyl-but-3-yn-2-ol (0.30 mL, 3.10 mmol) and the reaction vessel was evacuated and backfilled with nitrogen three times to remove atmospheric oxygen. Copper (I) iodide (40 mg, 10 mol %) was added and the reaction was stirred at room temperature for 5 h. After this time the solvent was removed under vacuum and the residue was filtered through a plug of silica gel (eluent=2:1 hexane:ethyl acetate) to give the crude alkynol product. This material was dissolved in isopropanol (10 mL) and treated with potassium hydroxide (150 mg, 2.67 mmol). The reaction mixture was heated to 70° C. for 4 h and then concentrated under vacuum and purified by silica-gel chromatography (eluent=4:1 hexane:ethyl acetate) to afford the product as a white solid (258 mg, 41% yield over two steps). $^1$H-NMR (CDCl$_3$) δ 7.41 (s, 1H), 7.38-7.31 (m, 9H), 7.13-7.07 (m, 6H), 7.05 (d, J=1 Hz, 1H), 3.05 (s, 1H).

(iii) [2-(1H-Imidazol-4-yl)-6-methoxy-benzofuran-3-yl]-(3,4,5-trimethoxyphenyl)-methanone Application of the general procedure to 2-iodo-5-methoxy-phenol, 4-ethynyl-1-trityl-1H-imidazole and 3,4,5-iodobenzene and silica-gel flash chromatography (sequential elution—3:1 hexane:ethyl acetate, 2:1, 1:1) provided crude [6-methoxy-2-(1-trityl-1H-imidazol-4-yl)-benzofuran-3-yl]-(3,4,5-trimethoxyphenyl)-methanone, contaminated with the corresponding non-carbonyl inserted derivative. This material was dissolved in methanol (~3 mL/100 mg) in a sealed vial and treated with trifluoroacetic acid (10% by volume). The reaction mixture was shaken overnight at 40° C. and the solvent removed by evaporation under a stream of air.

The crude residue was dissolved in ethyl acetate and washed with 10% NaOH$_{(aq)}$ solution. The organic layer was separated, dried over magnesium sulphate and the solvent removed under vacuum to give a dark residue that was purified by silica-gel chromatography (sequential elution—DCM:ethyl acetate 1:1, ethyl acetate). The pure product was solidified by freeze-drying with t-butanol. $^1$H-NMR (CDCl$_3$) δ 7.88 (br s, 1H), 7.80 (br s, 1H), 7.09 (s, 2H), 7.07 (d, J=2.0 Hz, 1H), 6.97 (d, J=8.8 Hz, 1H), 6.77 (dd, J=8.8, 2.0 Hz, 1H), 3.95 (s, 3H), 3.85 (s, 3H), 3.79 (s, 6H).

e) Preparation of 2-(4-N-Methylpyrazolyl)-3-(3,4,5-trimethoxybenzoyl)-6-methoxy-7-hydroxy-benzofuran (entry 14, Table 1)

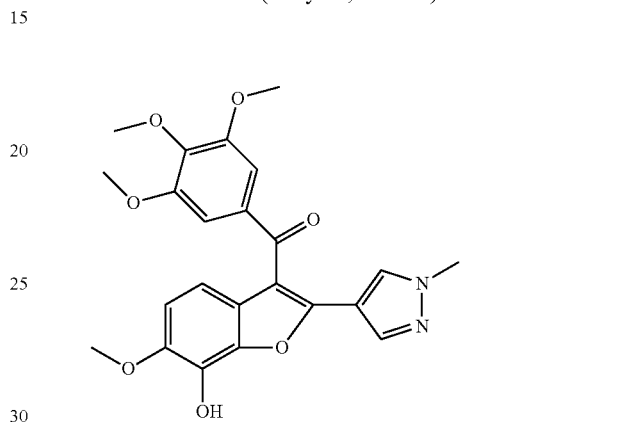

(i) 2-(4-N-Methylpyrazolyl)-3-(3,4,5-trimethoxybenzoyl)-6-methoxy-7-isopropoxy-benzofuran Application of the general procedure to 2-isopropoxy-3-methoxy-5-iodophenol (200 mg, 0.65 mmol), 4-ethynyl-1-methyl-1-H-pyrazole (83 mg, 0.78 mmol), 3,4,5-trimethoxy-iodobenzene (210 mg 0.71 mmol) afforded the title compound as a yellow paste which was crystallised from methanol to give a yellow crystalline solid; (172 mg, 55%); $^1$H NMR (300 MHz, CDCl$_3$) δ 8.12 (s, 1H), 7.98 (s, 1H), 7.13 (s, 2H, benzoyl Hs), 6.84 (d, 1H, J=8.63 Hz), 6.79 (d, 1H, J=8.67 Hz), 4.73 (m, 1H), 3.93 (bs, 6H), 3.88 (s, 3H), 3.77 (s, 6H, 2×OMe), 1.41 (d, 6H, J=6.16 Hz).

(ii) 2-(4-N-Methylpyrazolyl)-3-(3,4,5-trimethoxybenzoyl)-6-methoxy-7-hydroxy-benzofuran To a solution of 2-(4-N-methylpyrazolyl)-3-(3,4,5-trimethoxybenzoyl)-6-methoxy-7-isopropoxy-benzofuran (85 mg, 0.18 mmol) in dry dichloromethane (3 mL) was added solid aluminium chloride (48 mg, 0.36 mmol). The reaction mixture was stirred vigorously at room temperature for 10 minutes and another portion of aluminium chloride (10 mg) was added and stirring continued for 20 minutes (tlc), quenched with saturated ammonium chloride solution and extracted with ethyl acetate (20 mL). The organic layer was washed with water (5 mL), dried over magnesium sulphate and concentrated under vacuum. The crude product was purified by flash chromatography (silica gel, gradient elution=hexane/diethyl ether; 2:8 to neat diethyl ether) to afford the title compound as a crystalline yellow solid. (37 mg, 47%); $^1$H NMR (300 MHz, CDCl$_3$) δ 8.15 (s, 1H), 8.03 (s, 1H), 7.13 (s, 2H, benzoyl Hs), 6.79 (d, 1H, J=8.62 Hz), 6.69 (d, 1H, J=8.58 Hz), 3.92 (bs, 6H), 3.91 (s, 3H), 3.77 (s, 6H).

f) Preparation of 2-(4-N-methylpyrazolyl)-3-(3,5-dimethoxybenzoyl)-6-methoxy-7-hydroxy-benzofuran (entry 24, Table 1)

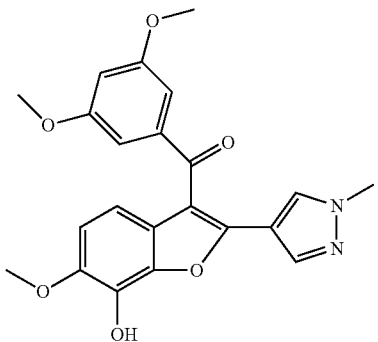

(i) 2-(4-N-methylpyrazolyl)-3-(3,5-dimethoxybenzoyl)-6-methoxy-7-isopropoxy-benzofuran Application of the general procedure applied to 2-isopropoxy-3-methoxy-5-iodophenol, 4-ethynyl-1-methyl-1-H-pyrazole, but replacing 3,4,5 trimethoxyiodobenzene with 3,5-dimethoxyiodobenzene afforded the title compound as a yellow crystalline solid. (102 mg, 77%); $^1$H NMR (300 MHz, CDCl$_3$) δ 8.18 (s, 1H), 7.98 (s, 1H), 6.96 (d, 2H, J=2.30 Hz, benzoyl Hs), 6.79 (d, 1H, J=8.70 Hz), 6.75 (d, 1H, J=8.68 Hz), 6.66 (t, 1H, J=2.32 Hz), 4.71 (quin, 1H), 3.92 (s, 3H), 3.87 (s, 3H), 3.76 (s, 6H, 2×OMe), 1.41 (d, 6H, J=6.16 Hz).

(ii) 2-(4-N-methylpyrazolyl)-3-(3,5-dimethoxybenzoyl)-6-methoxy-7-hydroxy-benzofuran When 2-(4-N-methylpyrazolyl)-3-(3,4,5-trimethoxybenzoyl)-6-methoxy-7-isopropoxy-benzofuran was substituted with 2-(4-N-methylpyrazolyl)-3-(3,5-dimethoxybenzoyl)-6-methoxy-7-isopropoxy-benzofuran in example 1 (e)(ii) above the identical procedure afforded the title compound as a yellow crystalline solid. (44 mg, 69%); $^1$H NMR (300 MHz, CDCl$_3$) δ 8.19 (s, 1H), 8.03 (s, 1H), 6.96 (d, 2H, J=2.86 Hz), 6.78 (d, 1H, J=8.63 Hz), 6.65 (t, 1H, J=1.95 Hz), 6.63 (d, 1H, J=8.50 Hz), 3.91 (s, 6H), 3.76 (s, 6H, 2×OMe).

g) 2-(N-Methyl-pyrazole)-6,7-oxazol-7-yl]-(3,4,5-trimethoxy-phenyl)-benzofuran (entry 33, Table 1)

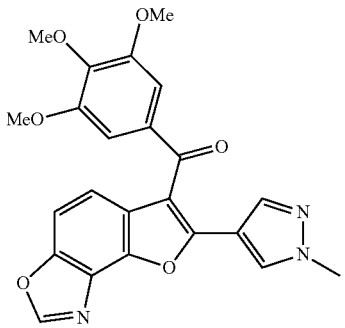 [SMILES: COc1cc(C(=O)c2c(-c3cnn(C)c3)oc3c2ccc2ocnc23)cc(OC)c1OC]

This material was prepared according to the general procedure for carbonylative multicomponent coupling using 7-hydroxy-6-iodobenzoxazole, 4-ethynyl-1-methyl-1-H-pyrazole and 3,4,5-trimethoxyiodobenzene.

$^1$H NMR (300 MHz, CDCl$_3$) δ 8.32 (s, 1H), 8.10 (s, 1H), 7.90 (s, 1H), 7.03 (s, 2H, benzoyl Hs), 6.85 (d, 1H, J=8.62 Hz), 6.77 (d, 1H, J=8.77 Hz), 3.84 (s, 3H), 3.83 (s, 3H), 3.69 (s, 6H, 2×OMe).

Example 2

A series of compounds of the invention were prepared by derivatization of the 1-pyrazolyl position of [6-Methoxy-2-(1H-pyrazol-4-yl)-benzofuran-3-yl]-(3,4,5-trimethoxyphenyl)-methanone a) Preparation of {4-[6-Methoxy-3-(3,4,5-trimethoxy-benzoyl)-benzofuran-2-yl]-pyrazol-1-yl}-acetic acid ethyl ester (entry 30, Table 1)

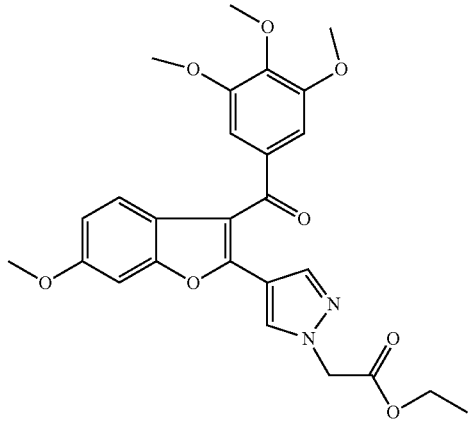 [SMILES: CCOC(=O)Cn1cc(-c2oc3cc(OC)ccc3c2C(=O)c2cc(OC)c(OC)c(OC)c2)cn1]

To a stirred solution of [6-Methoxy-2-(1H-pyrazol-4-yl)-benzofuran-3-yl]-(3,4,5-trimethoxyphenyl)-methanone (45 mg, 0.091 mmol) and potassium carbonate (40 mg, 0.29 mmol) in dry DMF (2.5 mL) was added ethyl bromoacetate (30 µL, 0.27 mmol) and the reaction heated to 70° C. for 2 h. After cooling to room temperature the reaction mixture was quenched with 10% NH$_4$Cl$_{(aq)}$ (20 mL) and extracted with ethyl acetate (30 mL). The organic layer was separated and washed with water (3×10 mL) and brine (10 mL), dried over magnesium sulphate and the solvent removed under reduced pressure. The crude residue was purified by flash column chromatography (silica gel, eluent=2:1 hexane:ethyl acetate) to give the title compound as a yellow solid (44 mg, 98%). $^1$H-NMR (CDCl$_3$) δ 8.28 (s, 1H), 8.06 (s, 1H), 7.13 (s, 2H), 7.10 (d, J=8.7 Hz, 1H), 7.04 (d, J=2.1 Hz, 1H), 6.79 (dd, J=8.7, 2.1 Hz, 1H), 4.91 (s, 2H), 4.23 (q, J=7.1 Hz, 2H), 3.93 (s, 3H), 3.86 (s, 3H), 3.77 (s, 6H), 1.27 (t, J=7.1 Hz, 3H).

b) Preparation of Sodium {4-[6-Methoxy-3-(3,4,5-trimethoxy-benzoyl)-benzo[b]furan-2-yl]-pyrazol-1-yl}-acetate (entry 29, Table 1)

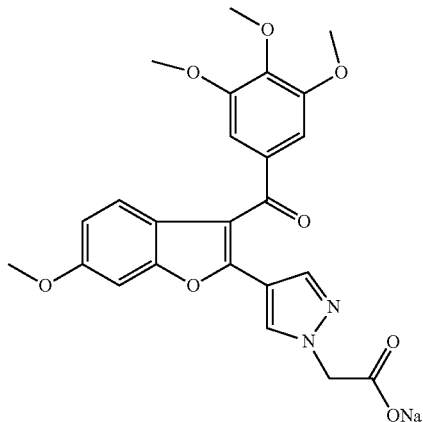

To a stirred solution of {4-[6-methoxy-3-(3,4,5-trimethoxy-benzoyl)-benzofuran-2-yl]-pyrazol-1-yl}-acetic acid ethyl ester (25 mg, 0.051 mmol) in a mixture of THF (1 mL) and water (1 mL) was added sodium hydroxide (70 mg, 1.75 mmol) and the reaction allowed to stir overnight at ambient temperature. After this time the reaction was concentrated under vacuum and the residue dissolved in water (20 mL) and washed with diethyl ether (5 mL). The aqueous layer was acidified to pH 1-2 with concentrated hydrochloric acid and extracted with ethyl acetate (2×15 mL). The combined organic layers were concentrated under vacuum, the residue was dissolved in methanol (2 mL) and the resulting solution was treated with a methanolic solution of sodium methoxide until a pH of 9 was obtained. The solvent was removed under vacuum and the resulting yellow solid was washed with small portions of cold diethyl ether and isopropanol to provide the title compound (22 mg, 89%). $^1$H-NMR (D$_2$O) δ 7.48 (s, 1H), 7.28 (s, 1H), 6.68-6.60 (m, 2H), 6.60 (s, 2H), 6.28 (d, J=7.6 Hz, 1H), 4.49 (s, 2H), 3.61 (s, 3H), 3.49 (s, 3H), 3.39 (s, 6H).

c) Preparation of 2-{4-[6-Methoxy-3-(3,4,5-trimethoxy-benzoyl)-benzo[b]furan-2-yl]-pyrazol-1-yl}-acetamide (entry 31, Table 1)

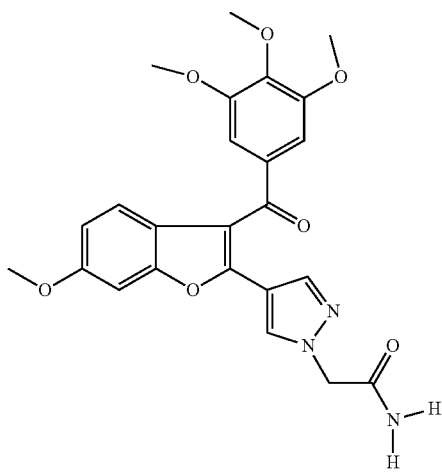 [SMILES: COc1ccc2c(C(=O)c3cc(OC)c(OC)c(OC)c3)c(-c3cnn(CC(N)=O)c3)oc2c1]

{4-[6-methoxy-3-(3,4,5-trimethoxy-benzoyl)-benzofuran-2-yl]-pyrazol-1-yl}-acetic acid ethyl ester (30 mg, 0.061 mmol) was treated with 28% aqueous ammonia solution and the resulting reaction mixture was stirred at 80° C. for 3 h. After cooling to room temperature the solution was concentrated under vacuum and the residue subjected to flash column chromatography (silica gel, sequential elution—1:1 hexane:ethyl acetate, ethyl acetate). The resulting product was further purified by trituration with 1:1 hexane:diethyl ether to give the title compound as a yellow solid (4 mg, 14%). $^1$H-NMR (CDCl$_3$) δ 8.29 (s, 1H), 8.14 (s, 1H), 7.13 (s, 2H), 7.12 (d, J=8.7 Hz, 1H), 7.05 (d, J=2.1 Hz, 1H), 6.81 (dd, J=8.7, 2.1 Hz, 1H), 6.14 (br s, N—H), 5.46 (br s, N—H), 4.83 (s, 2H), 3.93 (s, 3H), 3.86 (s, 3H), 3.78 (s, 6H).

d) Preparation of {6-Methoxy-2-[1-(4-methoxy-phenyl)-1H-pyrazol-4-yl]-benzofuran-3-yl}-(3,4,5-trimethoxyphenyl)-methanone (entry 40, Table 1)

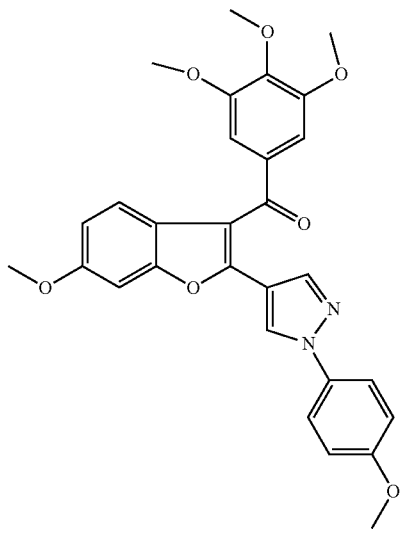 [SMILES: COc1ccc(-n2cc(-c3oc4cc(OC)ccc4c3C(=O)c3cc(OC)c(OC)c(OC)c3)cn2)cc1]

To an 8 mL screw cap glass vial was added [6-methoxy-2-(1H-pyrazol-4-yl)-benzofuran-3-yl]-(3,4,5-trimethoxyphenyl)-methanone (11 mg, 0.027 mmol), 3 Å molecular sieves, dichloromethane (0.5 mL), cupric acetate (10 mg, 0.054 mmol), 4-methoxy-phenyl boronic acid (9 mg, 0.059 mmol) and pyridine (15 μL, excess) and the capped vial was shaken at room temperature for two days with occasional removal of the cap to expose the mixture to atmospheric oxygen. After this time the reaction mixture was filtered through celite and the filtrate was concentrated and purified by silica-gel flash chromatography (eluent=hexane:ethyl acetate, 3:1) to afford the product as a yellow solid (2 mg, 15% yield). $^1$H-NMR (CDCl$_3$) δ 8.56 (s, 1H), 8.17 (s, 1H), 7.60 (d, J=8.9 Hz, 2H), 7.15 (s, 2H), 7.14 (d, J=8.7 Hz, 1H), 7.07 (d, J=2.0 Hz, 1H), 6.96 (d, J=8.9 Hz, 2H), 6.81 (dd, J=8.7, 2.0 Hz, 1H), 3.92 (s, 3H), 3.87 (s, 3H), 3.84 (s, 3H), 3.78 (s, 6H).

e) Preparation of {2-[1-(2-Dimethylamino-ethyl)-1H-pyrazol-4-yl]-6-methoxy-benzofuran-3-yl}-(3,4,5-trimethoxyphenyl)-methanone (entry 42, Table 1)

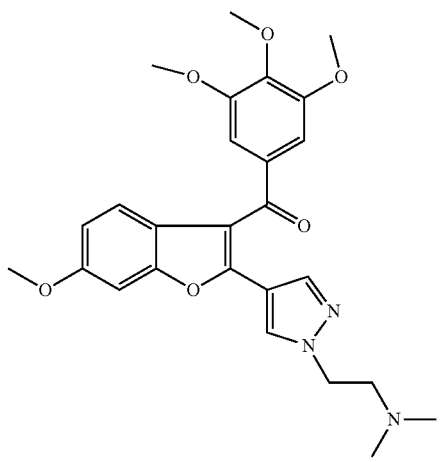

To a stirred solution of [6-Methoxy-2-(1H-pyrazol-4-yl)-benzofuran-3-yl]-(3,4,5-trimethoxyphenyl)-methanone (45 mg, 0.11 mmol) in dry DMSO (1.5 mL) was added sodium hydride (60% dispersion in mineral oil, 13 mg, 0.33 mmol) and the reaction was stirred at room temperature for 20 minutes. After this time the resulting yellow suspension was treated with 2-chloroethyl-dimethylamine hydrogen chloride (24 mg, 0.17 mmol) and heated to 35-40° C. for 5 h. The reaction was quenched with water (15 mL) and ethyl acetate (20 mL) and the aqueous layer was washed with further portions of ethyl acetate (2×10 mL). The combined organic layers were dried over magnesium sulphate and the solvent was removed under vacuum. The crude residue was purified by flash chromatography (alumina activated with 1.2% water, sequential elution—1:1 DCM:hexane, 9:1 DCM:ethyl acetate) to afford the product as a yellow resinous gum (23 mg, 44% yield). $^1$H-NMR (CDCl$_3$) δ 8.17 (s, 1H), 8.00 (s, 1H), 7.12 (s, 2H), 7.11 (d, J=8.7 Hz, 1H), 7.03 (d, J=2.2 Hz, 1H), 6.79 (dd, J=8.7, 2.2 Hz, 1H), 4.23 (t, J=6.7 Hz, 2H), 3.92 (s, 3H), 3.85 (s, 3H), 3.77 (s, 6H), 2.78 (t, J=6.7 Hz, 2H), 2.27 (s, 6H). $^{13}$C-NMR (CDCl$_3$) δ 190.3, 158.1, 153.6, 152.9, 142.2, 139.0, 133.7, 130.4, 121.7, 120.9, 113.7, 112.5, 112.2, 111.5, 106.9, 95.5, 61.0, 58.7, 56.1, 55.7, 50.4, 45.4.

f) 2-{4-[7-Hydroxy-6-methoxy-3-(3,4,5-trimethoxy-benzoyl)-benzofuran-2-yl]-pyrazol-1-yl}-acetamide (entry 51, Table 1)

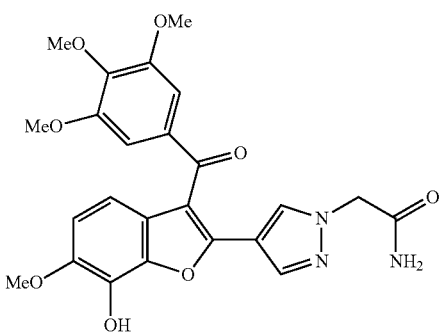 [SMILES: COc1cc(C(=O)c2c(-c3cnn(CC(N)=O)c3)oc3c(O)c(OC)ccc23)cc(OC)c1OC]

General procedure for carbonylative multicomponent coupling described above was applied to 6-iodo-2-isopropoxy-3-methoxy-phenol (440 mg, 1.43 mmol) with 4-ethynyl-1-(4-methoxybenzyl)-1H-pyrazole and 3,4,5-trimethoxy-iodobenzene followed by flash chromatography (silica-gel, eluted with EtOAc:hexanes, 2:3) gave the crude product (730 mg) contaminated with the non-carbonyl inserted material and other unidentified impurities. A portion of this crude material (460 mg) was dissolved in trifluoroacetic acid (7 ml) and refluxed for 2 days. The reaction was cooled, concentrated under reduced pressure and subjected to flash chromatography (silica-gel, eluted with EtOAc:hexanes, 3:2) to give the yellow solid product contaminated with the non-carbonyl inserted material (120 mg). This material was used directly in the next step.

To a suspension of the crude 2-pyrazolyl-benzofuran (100 mg) and K$_2$CO$_3$ $_{(s)}$ (2 eqs) in dry MeCN (4 ml) was added 2-bromoacetamide (1.2 eqs) and the reaction was heated to 70° C. for 3 hours. The mixture was cooled, concentrated onto silica-gel under reduced pressure and subjected to flash chromatography (silica-gel, eluted with 1:1 CH$_2$Cl$_2$: EtOAc+1% MeOH) to give the crude product (100 mg) which was used directly in the next step.

The crude acetamide (100 mg) was dissolved in dry CH$_2$Cl$_2$ (5 ml), cooled to 0° C. and treated with AlCl$_3$ (50 mg). TLC analysis of the reaction mixture revealed rapid but incomplete formation of the product. Three additional portions of AlCl$_3$ were added at 20 minute intervals until no starting material could be detected by TLC. The reaction was then quenched with saturated NaHCO$_{3(aq)}$ and extracted with CH$_2$Cl$_2$. The organic layer was washed with brine, dried over MgSO$_4$ and concentrated under reduced pressure and the resulting residue purified by preparative TLC (eluted with 5:1 CH$_2$Cl$_2$: EtOAc) to give the product as a yellow solid (8 mg, 2% from starting iodophenol). $^1$H-NMR (300 MHz, d$^6$-DMSO) δ 9.54 (s, 1H), 8.25 (s, 1H), 7.86 (s, 1H), 7.71 (s, 1H), 7.53 (s, 1H), 7.25 (s, 1H), 7.09 (s, 2H), 6.93 (d, J=8.3 Hz, 1H), 6.60 (d, J=8.3 Hz, 1H), 4.80 (s, 2H), 3.79 (s, 3H), 3.73 (s, 3H), 3.67 (s, 6H). MS (ESI) m/z (%): 482 (M+H$^+$, 100).

Example 3

Derivitisation of the 1-imidazoyl position of [2-(1H-Imidazol-4-yl)-6-methoxy-benzofuran-3-yl]-(3,4,5-trimethoxyphenyl)-methanone a) Preparation of [2-(1-methyl-1H-Imidazol-4-yl)-6-methoxy-benzofuran-3-yl]-(3,4,5-trimethoxyphenyl)-methanone (entry 39, Table 1)

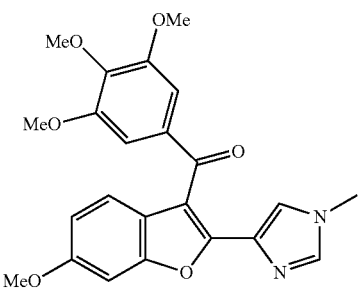 [SMILES: COc1ccc2c(C(=O)c3cc(OC)c(OC)c(OC)c3)c(-c3cn(C)cn3)oc2c1]

This material was prepared by N-methylation of [2-(1H-Imidazol-4-yl)-6-methoxy-benzofuran-3-yl]-(3,4,5-trimethoxyphenyl)-methanone (entry 45, Table 1) was made from I1-0085 by N-methylation. 20 mg of starting material (0.049 mmol) was dissolved in 1 ml dry THF then treated with 9 mg of 60% NaH (0.225 mmol) then after 10 minutes with MeI (15 uL, 0.24 mmol) and left over night then quenched with 10% NH4Cl extracted with EtOAc and chromatographed with straight EtOAc to give 12 mg product (58% yield). Proton data is 7.86 (s, 1H), 7.62 (s, 1H), 7.13-7.09 (m, 2H), 7.12 (s, 2H), 6.79 (dd, J=8.7, 2.1 Hz, 1H), 3.92 (s, 3H), 3.84 (s, 3H), 3.76 (s, 6H), 3.72 (s, 3H).

Example 4

Introduction of a Physiologically Labile Group, e.g. Disodium Phosphate Ester or Aminoacid Ester or Amide a) Preparation of 2-(4-N-methylpyrazolyl)-3-(3,4,5-trimethoxybenzoyl)-6-methoxy-7-O-disodiumphosphate-benzofuran (entry 23, Table 1)

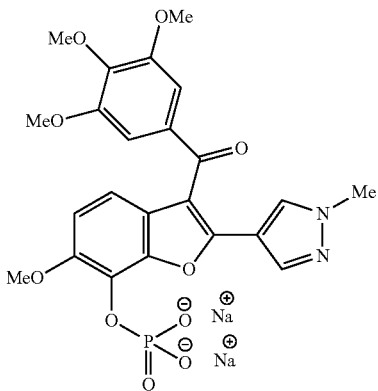 [SMILES: COc1cc(C(=O)c2c(-c3cnn(C)c3)oc3c(OP(=O)([O-])[O-])c(OC)ccc23)cc(OC)c1OC ; [Na+] ; [Na+]]

(i) 2-(4-N-methylpyrazolyl)-3-(3,4,5-trimethoxybenzoyl)-7-O-dibenzylphosphate-6-methoxybenzo[b]furan To a stirred solution of 2-(4-N-methylpyrazolyl)-3-(3,4,5-trimethoxyphenyl)-6-methoxy-7-hydroxy-benzofuran (62 mg, 0.14 mmol), carbontetrabromide (57 mg, 0.17 mmol) and triethylamine (29 μL, 0.20 mmol) in dry acetonitrile (4 mL) at 0° C. was added a solution of dibenzyl-phosphite (37 μL, 0.17 mmol) in dry acetonitrile (1 mL). After 1.5 hrs the reaction was quenched with water (2 mL) and diluted with ethyl acetate (20 mL). The organic layer was washed with water, dried over magnesium sulphate and the solvent was removed under vacuum. The crude product was purified by flash chromatography (silica gel, eluent=hexane/ethyl-acetate 4:6) to afford the title compound as a pale yellow paste; (19 mg, 20%); $^1$H NMR (300 MHz, CDCl$_3$) δ 7.88 (s, 1H), 7.78 (s, 1H), 7.42-7.29 (m, 10 Hs), 7.12 (s, 2H, benzoyl Hs), 6.99 (dd, 1H, J=8.75, 1.29 Hz), 6.84 (d, 2H, J=8.74 Hz), 5.40-5.28 (m, 4H), 3.93 (s, 3H, OMe), 3.84 (s, 3H, OMe), 3.80 (s, 3H, OMe), 3.78 (s, 6H, 2×OMe).

(ii) 2-(4-N-methylpyrazolyl)-3-(3,4,5-trimethoxybenzoyl)-6-methoxy-7-β-disodiumphosphate-benzofuran To a stirred solution of 2-(4-N-methylpyrazolyl)-3-(3,4,5-trimethoxybenzoyl)-6-methoxy-7-O-dibenzylphosphate-benzofuran (19 mg, 0.028 mmol) in dry acetonitrile (2 mL) at 0° C. under nitrogen was added trimethylsilylbromide (10 μL, 0.074 mmol) and the reaction mixture was stirred for 5 hours at room temperature. After this time the solvent was distilled and the residue was dissolved in distilled methanol (2 mL). A solution of sodium methoxide in methanol was added until the pH was 12. The solvent was removed under vacuum and isopropyl alcohol (1 mL) was added. The precipitate were filtered and washed with isopropyl alcohol and dried to afford the title compound as a crystalline yellow solid; (11 mg, 69%); $^1$H NMR (300 MHz, D$_2$O) δ 7.80 (s, 1H), 7.49 (s, 1H), 7.19 (d, 1H, J=8.19 Hz), 6.91 (s, 2H, benzoyl Hs), 6.98 (d, 1H, J=8.34 Hz), 3.83 (s, 3H, OMe), 3.74 (s, 3H, OMe), 3.71 (s, 3H, OMe), 3.64 (s, 6H, 2×OMe).

b) Preparation of 2-(2-Thiazolyl)-7-O-disodiumphosphate-6-methoxy-3-(3,4,5-trimethoxybenzoyl)-benzo[b]furan (entry 48, Table 1)

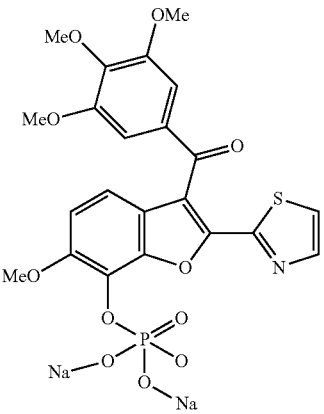

This material was prepared from 7-hydroxy-2-(2-thiazolyl)-3-(3,4,5-trimethoxybenzoyl)-6-methoxy-benzo[b]furan (entry 44, Table 1) using an identical two step procedure as that described for 2-(4-N-methylpyrazolyl)-3-(3,4,5-trimethoxybenzoyl)-7-O-disodiumphosphate-6-methoxy-benzo[b]furan (entry 23, Table 1), above.

(i) 2-(2-Thiazolyl)-7-O-dibenzylphosphate-6-methoxy-3-(3,4,5-trimethoxybenzoyl)-benzo[b]furan Yield 221 mg, 78%; $^1$H NMR (300 MHz, CDCl$_3$)-δ: 7.73 (d, J=3.1 Hz, 1H), 7.39 (d, J=7.22 Hz, 1H), 6.14 (s, 1H), 7.34 (m, 2H), 7.05-6.87 (m, 11H), 5.32-5.24 (m, 4H, benzyl Hs), 3.90 (s, 3H, OMe), 3.77 (s, 3H, OMe), 3.74 (s, 6H, 2×OMe).

(ii) 2-(2-Thiazolyl)-7-O-disodiumphosphate-6-methoxy-3-(3,4,5-trimethoxybenzoyl)-benzo[b]furan Yield 87 mg, 58%; $^1$H NMR (300 MHz, D$_2$O)-δ: 7.65 (bs, 1H), 7.64 (bs, 1H), 7.24 (d, J=8.68 Hz, 1H), 7.10 (s, 2H, benzoyl Hs), 7.08 (d, 1H), 3.86 (s, 3H, OMe), 3.73 (s, 3H, OMe), 3.65 (s, 6H, 2×OMe).

c) 7-(O-disodiumphosphate)-2-(2-furyl)-6-methoxy-3-(3,4,5-trimethoxybenzoyl)benzo-[b]furan (entry 47, Table 1)

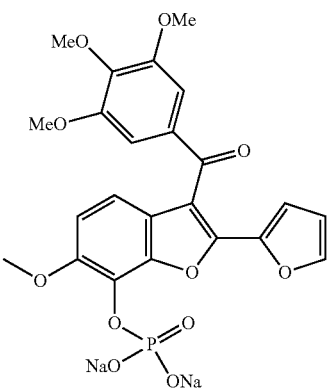

This material was prepared from 2-(2-furanyl)-7-hydroxy-6-methoxy-3-(3,4,5-trimethoxybenzoyl)benzo[b]furan (entry 36, Table 1) using an identical two step procedure as that described for 2-(4-N-methylpyrazolyl)-3-(3,4,5-trimethoxybenzoyl)-7-O-disodiumphosphate-6-methoxybenzo[b]furan (entry 23, Table 1), above (i) 7-(O-dibenzylphosphate)-2-(2-furyl)-6-methoxy-3-(3,4,5-trimethoxybenzoyl)benzo-[b]furan Yield (95%). $^1$H NMR (300 MHz, CDCl$_3$) δ 3.76 (s, 6H), 3.86 (s, 3H), 3.91 (s, 3H), 5.39 (m$_c$, 4H), 6.37 (dd, J=1.8, 3.6, 1H), 6.78 (d, J=3.6, 1H), 6.94 (d, J=8.7, 1H), 7.14 (s, 2H), 7.22-7.41 (m, 11H).

(ii) 7-(O-Disodiumphosphate)-2-(2-furyl)-6-methoxy-3-(3,4,5-trimethoxybenzoyl)benzo-[b]furan Yield (83%). $^1$H NMR (300 MHz, CDCl$_3$) δ 3.61 (s, 6H), 3.71 (s, 3H), 3.83 (s, 3H), 6.40-6.43 (m, 1H), 6.91 (d, J=3.6, 1H), 6.96 (d, J=8.7, 1H), 7.02 (s, 2H), 7.11 (d, J=8.7, 1H), 7.29 (bs, 1H).

d) 7-(O-Disodiumphosphate)-2-(2-thiophenyl)-6-methoxy-3-(3,4,5-trimethoxybenzoyl)benzo-[b]furan (entry 50, Table 1)

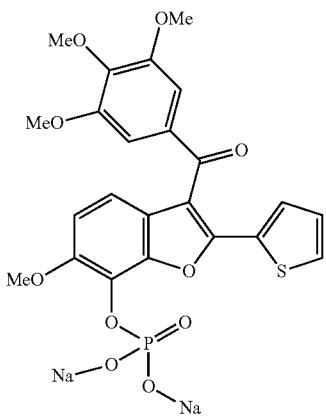

This material was prepared from 7-hydroxy-2-(2-thiophenyl)-3-(3,4,5-trimethoxybenzoyl)-6-methoxy-benzo[b]furan (entry 28, Table 1) using an identical two step procedure as that described for 2-(4-N-methylpyrazolyl)-3-(3,4,5-trimethoxybenzoyl)-7-O-disodiumphosphate-6-methoxybenzo[b]furan (entry 23, Table 1), above (i) 7-(O-dibenzylphosphate)-2-(2-thiophenyl)-6-methoxy-3-(3,4,5-trimethoxybenzoyl)benzo-[b]furan Yield=97%

(ii) 7-(O-Disodiumphosphate)-2-(2-furyl)-6-methoxy-3-(3,4,5-trimethoxybenzoyl)benzo-[b]furan Yield 90%. $^1$H-NMR (300 MHz, D$_2$O) δ 7.45 (d, J=4.9 Hz, 1H), 7.34 (d, J=3.4 Hz, 1H), 7.16 (d, J=8.9 Hz, 1H), 7.09 (s, 2H), 7.00 (d, J=8.9 Hz, 1H), 6.92 (dd, J=4.9, 3.4 Hz, 1H), 3.84 (s, 3H), 3.71 (s, 3H), 3.65 (s, 6H). $^{13}$C-NMR (75 MHz, D$_2$O) δ 193.0, 154.3, 151.9, 150.0, 146.7, 141.3, 132.7, 130.7, 129.8, 129.6, 128.1, 128.0, 127.3, 122.4, 114.3, 110.8, 107.6, 60.6, 56.7, 55.8.

e) Preparation of 2-Imidazol-1-yl-7-O-bis-(triethylammonium)phosphate-6-methoxy-3-(3,4,5-trimethoxybenzoyl)-benzo[b]furan (entry 49, Table 1)

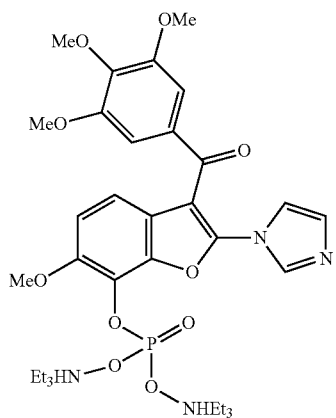

(i) 2-Imidazol-1-yl-7-O-dibenzylphosphate-6-methoxy-3-(3,4,5-trimethoxybenzoyl)-benzo[b]furan This material was prepared using an identical procedure as that described for 2-(4-N-methylpyrazolyl)-3-(3,4,5-trimethoxybenzoyl)-7-O-dibenzylphosphate-6-methoxybenzo[b]furan, above.

Yield 430 mg, 86%. $^1$H NMR (300 MHz, CDCl$_3$)-δ: 7.80 (s, 1H), 7.39-7.27 (m, 14 Hs), 7.16 (s, 1H), 6.98 (d, J=8.84 Hz, 1H), 5.35-5.24 (m, 4H, benzyl Hs), 3.89 (s, 3H, OMe), 3.87 (s, 3H, OMe), 3.76 (s, 6H, 2×OMe).

(ii) 2-Imidazol-1-yl-7-O-bis-(triethylammonium)-6-methoxy-3-(3,4,5-trimethoxybenzoyl)-benzo[b]furan To a stirred solution of 2-imidazol-1-yl-7-O-di-benzylphosphate-3-(3,4,5-trimethoxybenzoyl)-6-methoxybenzo[b]furan (310 mg, 0.45 mmol) in dry acetonitrile (1.5 mL) at 0° C. was added trimethylsilylbromide (250 μL, 1.93 mmol) and the reaction mixture was stirred for 35 minutes (tlc). Solvent was distilled and the residue was put under high vacuum for 1 hr and then water (2 mL) was added to the residue. Triethylamine (138 μl, 0.93 mmol) was added and the residue went into solution after stirring for 15 minutes at room temperature. Ethyl acetate (6 mL) and water (3 mL) was added and stirring was continued for another 15 minutes. The aqueous layer was separated and washed with ethyl acetate (10 mL). The solvent was distilled under vacuum to gave the title compound as light yellow solid; (290 mg, 91%); $^1$H NMR (300 MHz, CDCl$_3$)-δ: 8.12 (s, 1H), 7.53 (s, 1H), 7.12 (d, J=8.53 Hz, 1H), 7.08 (s, 2H, benzoyl Hs), 6.96 (s, 1H), 6.87 (d, J=8.69 Hz, 1H), 3.90 (s, 3H, OMe), 3.88 (s, 3H, OMe), 3.75 (s, 6H, 2×OMe), 2.99 (q, J=14.5 and 7.21 Hz, 12H), 1.29 (t, J=7.24 Hz, 18H).

d) Preparation of 2S-2-Amino-3-hydroxy-N-(6-methoxy-2-(1-methyl-1H-pyrazol-4-yl)-3-(3,4,5-trimethoxybenzoyl)benzofuran-7-yl)propanamide Hydrochloride Salt (entry 60 Table 1)

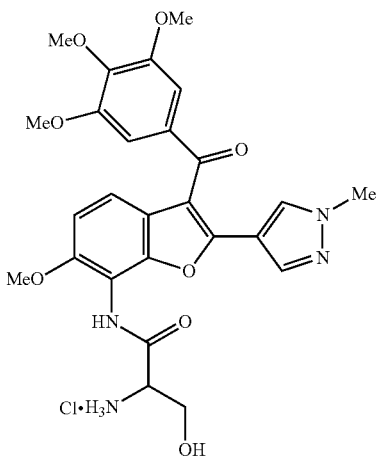

(i) tert-Butyl 4S-4-(6-methoxy-2-(1-methyl-1H-pyrazol-4-yl)-3-(3,4,5-trimethoxybenzoyl)-benzofuran-7-ylcarbamoyl)-2,2-dimethyloxazolidine-3-carboxylate To a solution of 7-amino-6-methoxy-2-(1-methyl-1H-pyrazol-4-yl)-3-(3,4,5-trimethoxybenzoyl)benzo[b]furan (entry 21, Table 1) (0.081 g, 0.185 mmol), 2,2-dimethyl-3-(1,1-dimethylethyl-4S-3,4-ozazolidinedicarboxylic acid (0.067 g, 0.27 mmol) and N,N-diisopropylethylamine (0.08 ml, 0.46 mmol) in anhydrous CH$_2$Cl$_2$ (1 ml) PyBroP (0.128 g, 0.46 mmol) was added at room temperature under N$_2$. The resulting mixture was stirred for 1 h at room temperature, than diluted to 15 ml with ethyl acetate and washed with 10% aqueous citric acid (1 ml), water, brine and dried over anhydrous MgSO$_4$ and filtered off. The filtrate was evaporated to dryness under reduced pressure and the residue was purified by flash column chromatography (silica-gel, CH$_2$Cl$_2$/ethyl acetate 9:1) giving the title compound (0.106 g, 87%) as a creamy solid. $^1$H NMR (300 MHz, CDCl$_3$) 8.09 (s, 1H), 7.93 (s, 1H), 7.13 (s, 2H), 7.03 (d, J=8.75 Hz, 1H), 6.8 (d, J=8.75 Hz, 1H), 4.1-4.7 (broad m, 2H), 3.91 (s, 3H), 3.89 (s, 3H), 3.87 (s, 3H), 3.82 (s, 3H), 3.77 (s, 6H), 3.33 (m, 1H), 1.23-1.7 (m, 14H).

(ii) 2S-2-Amino-3-hydroxy-N-(6-methoxy-2-(1-methyl-1H-pyrazol-4-yl)-3-(3,4,5-trimethoxybenzoyl)benzofuran-7-yl)propanamide Hydrochloride Salt To a solution of the product of the above reaction (0.106 g, 0.159 mmol) in anhydrous methanol (0.3 ml) chlorotrimethylsilane (0.148 ml, 1.2 mmol) was added drop wise at 0° C. under N$_2$. The resulting mixture was stirred overnight at room temperature and evaporated to dryness under reduced pressure. The solid residue was washed with methanol (1.5 ml), ethyl ether (2×2 ml) and hexane (2×2 ml) and dried, giving pure title compound (0.072 g, 81%), as a yellowish solid. $^1$H NMR (300 MHz, D$_2$O) 7.45 (s, 1H), 7.34 (s, 1H), 6.99 (d, J=8.77 Hz, 1H), 6.73 (d, J=8.77 Hz, 1H), 6.7 (s 2H), 4.66 (H$_2$O), 4.44 (m, 1H), 4.0-4.12 (m, 2H), 3.77 (s, 3H), 3.68 (s, 3H), 3.63 (s, 3H), 3.52 (s, 6H). MS (70 eV) 525.0 (M+1), 525.9 (M+2), 527.0 (M+3).

e) Preparation of 2-(Furan-2-yl)-6-methoxy-3-(3,4,5-trimethoxybenzoyl)benzofuran-7-yl ester of N$^\gamma$-nitro-L-arginine trifluoroacetate salt (entry 63, Table)

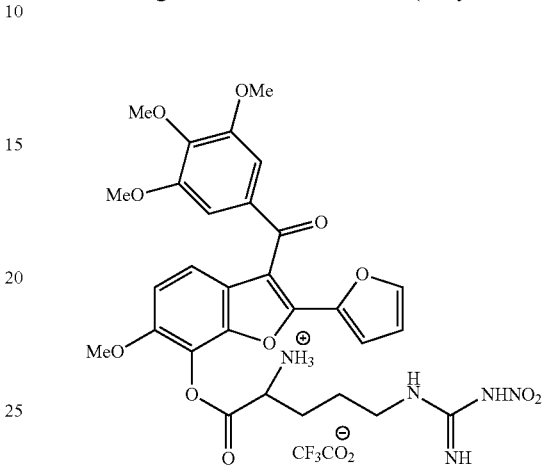

(i) 2-(Furan-2-yl)-6-methoxy-3-(3,4,5-trimethoxybenzoyl)benzofuran-7-yl Ester of N$^\alpha$-BOC-N$^\gamma$-nitro-L-arginine To a solution of 2-(furano-2-yl)-7-hydroxy-6-methoxy-3-(3,4,5-trimethoxybenzoyl)benzo[b]furan (entry 36, Table 1) (0.0353 g, 0.083 mmol), N$^\alpha$-BOC-N$^\gamma$-nitro-L-arginine (Etemad-Moghadam G, et al European J. Med. Chem., 1988, 23(6), 577-585) (0.067 g, 0.21 mmol) and N,N-diisopropylethylamine (0.072 ml, 0.42 mmol) in anhydrous dimethyl acetate (1 ml) PyBroP (0.097 g, 0.21 mmol) was added at room temperature under N$_2$. The resulting mixture was stirred for 2 h at room temperature, than diluted to 15 ml with ethyl acetate and washed with 10% aqueous citric acid (1 ml), water, brine and dried over anhydrous MgSO$_4$ and filtered off. The filtrate was evaporated to dryness under reduced pressure and the residue was purified by flash column chromatography (silica-gel, CH$_2$Cl$_2$/ethyl acetate 9:1) giving the title compound (0.041 g, 68%) as a creamy solid. $^1$H NMR (300 MHz, CDCl$_3$) 8.83 (broad s, 1H), 7.65 (broad s, 2H), 7.37 (m, 2H), 7.12 (s, 2H), 6.84-6.99 (m, 2H), 6.42 (m, 1H), 5.47 (m, 1H), 4.79 (m, 1H), 3.89 (s, 3H), 3.87 (s, 3H), 3.75 (s, 6H), 3.62 (m, 1H), 3.40 (m, 1H), 2.26 (m, 1H), 1.91 (m, 3H), 1.46 (s, 9H).

(ii) 2-(Furan-2-yl)-6-methoxy-3(3,4,5-trimethoxybenzoyl)benzofuran-7-yl ester of N$^\gamma$-nitro-L-arginine trifluoroacetate salt Trifluoroacetic acid (0.1 ml) was added to a solution of the product from the above reaction (0.041 g, 0.0564 mmol) in anhydrous CH$_2$Cl$_2$ (1.5 ml) at 0° C. and the mixture allowed to come to room temperature and stir for 16 h. The mixture was evaporated to dryness under reduced pressure and ethanol (2 ml) was added. The resulting solution was concentrated under reduced pressure and the procedure repeated twice. The residue was triturated with diethyl ether, giving the title compound (0.014 mg) as brownish solid. MS (70 eV) 625.9 (M+1), 626.9 (M+2).

Example 5 a) Preparation of [6-Methoxy-2-(1-methyl-1H-pyrazol-4-yl)-1H-indol-3-yl]-(3,4,5-trimethoxyphenyl)-methanone (entry 19, Table 1)

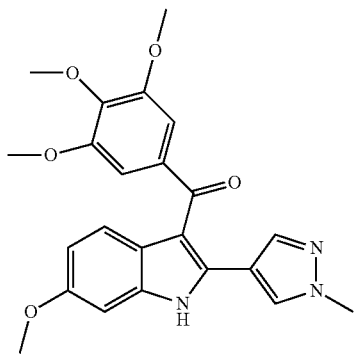

(i) 4-(2-N-acetamino-4-methoxy-phenylethynyl)-1-methyl-1H-pyrazole

To a mixture of 0.278 g (0.95 mmol) of 2-iodo-5-methoxyacetanilide, 0.122 g (1.15 mmol) of 4-ethynyl-1-methyl-1H-pyrazole, 0.028 g (0.04 mmol) of dichlorobis(triphenylphosphine)palladium (II) and 8 mg (0.042 mmol) of copper (I) iodide 4 mL of anhydrous acetonitrile and 2 mL of triethylamine were added under nitrogen atmosphere at room temperature. The resulting mixture was stirred for 1 hour, when TLC indicated a consumption of iodobenzene. The solvent was evaporated under reduced pressure and the residue purified by flash column chromatography (silica gel; dichloromethane:ethyl acetate 9:1) to give 0.24 g of pure product as colourless crystals. $H^1$-NMR ($CDCl_3$) 2.2 (s, 3H, $CH_3CO$); 3.81 (s, 3H, Me); 3.91 (s, 3H, MeO); 6.58 (dd, 1H, CH aromatic. J=8.56 Hz; J=2.28 Hz); 7.32 (d, 1H aromatic, J=8.56 Hz); 7.55 (s, 1H, CH pyr); 7.62 (s, 1H, CH pyr); 7.9 (s, 1H, NH); 8.019 s, 1H, CH aromatic).

(ii) 6-Methoxy-2-(1-methyl-1H-pyrazol-4-yl)-1H-indole

To 0.157 g (0.58 mmol) of the above product in 3 mL of anhydrous tetrahydrofuran 1.45 mL of 1M solution of tetrabutylammonium fluoride in tetrahydrofuran was added under nitrogen atmosphere. The resulting mixture was refluxed overnight (until TLC showed no starting material). The solvent was evaporated under reduced pressure and the residue was diluted to 25 mL with water. The product was extracted with ethyl acetate (3×25 mL). The combined organic phase was washed with saturated sodium chloride (20 mL) dried over anhydrous magnesium sulfate, filtered off, evaporated to dryness and purified by flash column chromatography (silica gel (hexane:ethyl acetate 1:1) to give 0.111 g (84% yield of the title compound as a colourless crystals. $H^1$ NMR ($CDCl_3$) 3.75 (s, 3H, Me), 3.98 (s, 3H, Me); 6.44 (s, 1H, CH-indole); 7.4 (dd, 1H, aromatic, J=2 Hz, J=8.6 Hz); 6.84 (s, 1H, aromatic); 7.41 (d, 1H, CH aromatic, J=8.6 Hz); 7.56 (s, 1H, CH pyr); 7.7 (s, 1H, CH pyr); 8.1 (broad s, 1H, NH indole).

(iii) [6-Methoxy-2-(1-methyl-1H-pyrazol-4-yl)-1H-indol-3-yl]-(3,4,5-trimethoxyphenyl)-methanone To a mixture of 0.1 g (0.44 mmol) of above product and 0.12 (0.88 mmol) of anhydrous zinc chloride in 3 mL of anhydrous dichloromethane 0.2 mL of 3M solution of methylmagnesium bromide in tetrahydrofuran was added dropwise at room temperature. The resulting suspension was stirred for one hour and to it a solution of 0.111 g (0.48 mmol) of 3,4,5-trimethoxybenzoyl chloride in 2 mL of anhydrous dichloromethane was added dropwise over 5 minutes at room temperature. The resulting mixture was stirred for one hour followed by addition of 0.052 mL (0.44 mmol) of tin(IV) chloride. The resulting mixture was stirred overnight at room temperature than quenched with 5 mL of water, extracted with dichloromethane (30 mL). The organic phase was dried over anhydrous magnesium sulfate, filtered off. Evaporation of filtrate and purification by flash column chromatography (silica gel, dichloromethane:ethyl acetate 1:1) gave 0.051 g (26% yield) of the title compound as a yellow crystals. $H^1$NMR (Acetone-$d_6$) 3.71 (s, 6H, 3,5-MeO); 3.77 (s, 3H, 4-Me)); 3.79 (s, 3H, Me); 3.86 (s, 3H, 6-MeO); 6.71 (dd, 1H, 5-CH, J=8.8 Hz, J=2.3 Hz); 6.93 (d, 1H, 7-H, J=2.3 Hz); 7.03 (s, 2H, 2,6-CH); 7.33 (d, 1H, 4-H, J=8.8 Hz); 7.74 (s, 1H, CH pyr); 7.96 (s, 1H, CH pyr).

Example 6 a) Preparation of 7-Amino-6-methoxy-2-(1-methyl-1H-pyrazol-4-yl)-3-(3,4,5-trimethoxybenzoyl)benzo[b]furan (entry 21, Table 1)

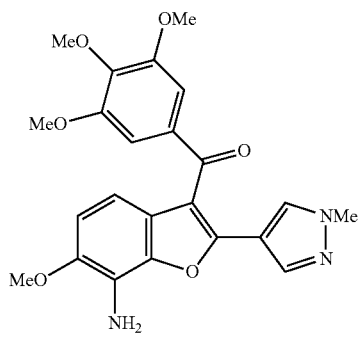 [SMILES: COc1cc(C(=O)c2c(-c3cnn(C)c3)oc3c(N)c(OC)ccc23)cc(OC)c1OC]

(i) 2,4-Dimethoxy-3-nitro-iodobenzene

A mixture of 1 g (6.4 mmol) of 2-nitroresorcinol, 1.42 g (6.4 mmol) of silver trifluoroacetate and 1.64 g (6.4 mmol) of iodine in 25 mL of chloroform was stirred overnight at room temperature. The reaction mixture was filtered through celite, washed with 20 mL of dichloromethane. The combined filtrate was washed with 10% aqueous sodium metabisulfite, water, brine and dried over anhydrous magnesium sulfate, evaporated to dryness to give 1.6 g of crude 4-iodo-2-nitroresorcinol [$H^1$ NMR ($CDCl_3$) 6.52 (d, 1H, CH, J=8.9 Hz); 7.85 (d, 1H, CH, J=8.9 Hz); 10.67 (s, 1H, OH); 11.43 (s, 1H, OH)] which was used in the next step without further purification. To a mixture of above product in 10 mL of anhydrous dimethylformamide 1.77 g (12.8 mmol) of anhydrous potassium carbonate was added at room temperature followed by 3 mL (48 mmol) of methyl iodide. After stirring overnight at room temperature resulting mixture was diluted to 150 mL with ethyl acetate, washed with water (3×15 mL) brine and dried over anhydrous magnesium sulfate, filtered off and filtrate evaporated to dryness to give 1.6 g of crude product, which was purified by flash column chromatography (silica gel hexane dichloromethane 7:3) to give 1.1 g (56%) of the title compound as a colourless crystals. H¹ NMR (CDCl₃) 3.87 (s, 3H, OMe); 3.91 (s, 1H, OMe); 6.6 (d, 1H, CH, J=8.9 Hz); 7.75 (d, 1H, CH, J=8.9 Hz).

(ii) 4-(2,4-Dimethoxy-3-nitro-phenylethynyl)-1-methyl-1H-pyrazole

To a mixture of 2,4-dimethoxy-3-nitro-iodobenzene (0.95 mmol), 0.122 g (1.15 mmol) of 4-ethynyl-1-methyl-1H-pyrazole, 0.028 g (0.04 mmol) of dichlorobis(triphenylphosphine)palladium (II) and 8 mg (0.042 mmol) of copper (I) iodide 4 mL of anhydrous acetonitrile and 2 mL of triethylamine were added under nitrogen atmosphere at room temperature. The resulting mixture was stirred for 1 hour, when TLC indicated a consumption of the iodobenzene. The solvent was evaporated under reduced pressure and the residue purified by flash column chromatography (silica gel; dichloromethane:ethyl acetate 9:1) to give the title compound in 71% yield as creamy crystals. H¹ NMR (CDCl₃) 3.88 (s, 3H, Me); 3.9 (s, 3H, OMe); 4.07 (s, 3H, OMe); 6.7 (d, 1H, CH, J=8.9 Hz); 7.44 (d, 1H, CH, J=8.9 Hz); 7.56 (s, 1H, CH pyr); 7.62 (s, 1H, CH pyr).

(iii) 4-(3-Iodo-6-methoxy-7-nitro-benzofurnan-2-yl)-1-methyl-1H-pyrazole

A mixture of 0.13 g (045 mmol) of above product and 0.21 g (0.543 mmol) of bis(pyridine) iodonium tetrafluoroborate in 3 mL of anhydrous tetrahydrofuran was refluxed for 1 hour under nitrogen atmosphere. After cooling to room temperature the reaction mixture was diluted to 50 mL with ethyl acetate, washed with 5% aqueous sodium metabisulfite, water, brine and dried over anhydrous magnesium sulfate and filtered off. Evaporation of the filtrate yielded 0.17 g of crude product which purified by flash column chromatography (silica gel, dichloromethane) to give 0.152 g (83% yield) of pure product as an yellow crystals. H¹-NMR (CDCl₃) 3.98 (s, 3H, Me); 3.99 (s, 3H, Me); 7.01 (d, 1H, CH, J=8.75 Hz); 7.405 (d, 1H, CH, J=8.75 Hz); 8.08 (s, 1H, CH pyr); 8.22 (s, 1H, CH pyr).

(iv) [6-Methoxy-7-nitro-2-(1-methyl-1H-pyrazol-4-yl)-benzofuran-3-yl]-(3,4,5-trimethoxyphenyl)-methanone (entry 20 Table 1)

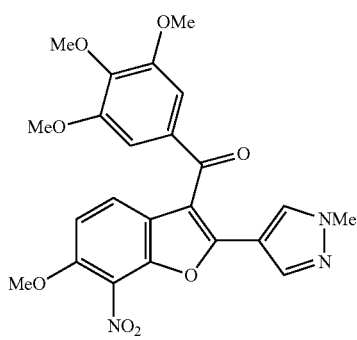 [SMILES: COc1cc(C(=O)c2c(-c3cnn(C)c3)oc3c([N+](=O)[O-])c(OC)ccc23)cc(OC)c1OC]

A mixture of 0.06 g (0.15 mmol) of above product 0.091 g (0.27 mmol) of trimethyl-(3,4,5-trimethoxyphenyl)-stannane, 0.024 g (0.02 mmol) of tetrakis(triphenylphosphine) palladium(0) in 4 mL of anhydrous dimethylsulfoxide was stirred for 7 hours at 80-90° C. under carbon monoxide atmosphere. After cooling to room temperature the mixture was diluted to 100 mL with ethyl acetate and washed with water (3×15 mL), brine (20 mL) and dried over anhydrous magnesium sulfate and filtered off. Evaporation of filtrate gave 0.126 g of crude product, which was purified by ethyl acetate to give 0.023 mg (33% yield) of pure product as an yellow crystals. H¹ NMR (CDCl₃) 3.78 (s, 6H, OMe); 3.91 (s, 3H, Me); 3.93 (s, 3H, Me); 3.98 (s, 3H, OMe); 6.91 (d, 1H, CH, j=8.9 Hz); 7.09 (s, 2H, CH); 7.34 (d, 1H, CH, J=8.9 Hz); 7.88 (s, 1H, CH pyr); 8.05 (s, 1H, CH pyr).

(v) [7-Amino-6-methoxy-2-(1-methyl-1H-pyrazol-4-yl)-benzofuran-3-yl]-(3,4,5-trimethoxyphenyl)-methanone To a solution of 0.012 g (0.0256 mmol) of the above product in 0.5 mL of glacial acetic acid 0.1 g (1.51 mmol) of zinc powder was at room temperature. The resulting mixture was stirred for one hour at room temperature, filtered trough a celite. The celite was washed with dichloromethane (2×10 mL). The combined filtrate was evaporated to dryness under reduced pressure and the residue purified by flash column chromatography (ethyl acetate dichloromethane 1:1) to give 4 mg (36% yield) of pure product as a yellow solid. H¹ NMR (CDCl₃) 2.0 (broad s, NH₂+H₂O); 3.77 (s, 6H, OMe); 3.84 (s, 3H, Me); 3.9 (s, 3H, OMe); 3.92 (s, 3H, OMe); 6.6-6.8 (m, 2H, CH); 7.12 (s, 2H, CH); 7.99 (s, 1H, CH pyr); 8.15 (s, 1H, CH pyr).

b) Preparation of 7-Amino-6-methoxy-2-(1-methyl-1H-pyrazol-4-yl)-3-(3,4,5-trimethoxyphenylthio) benzo[b]furan (entry 59 Table 1)

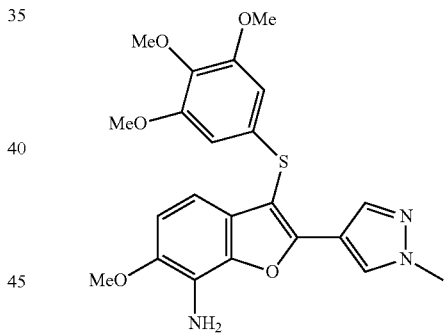

(i) 6-Methoxy-2-(1-methyl-1H-pyrazol-4-yl)-7-nitro-3-(3,4,5-trimethoxyphenylthio)benzo[b]furan A modified procedure of Buchwald et al (Organic Letters 2002, 4 (20) 3517-3520) was used. A mixture of 4-(3-iodo-6-methoxy-7-nitrobenzofuran-2-yl)-1-methyl-1H-pyrazole (0.0538 g, 0.135 mmol), 3,4,5-trimethoxy thiophenol (Dawson et al, J. Am. Chem. Soc., 2002, 124, 4642-4646), (0.041 g, 0.202 mmol), dry K₂CO₃ (0.038 g, 0.272 mmol), CuI (0.0051 g, 0.027 mmol) and 2-phenylphenol (0.0091 g, 0.053 mmol) in dry toluene (1.5 ml) was degassed under reduced pressure and saturated with dry N₂. The resulting mixture was stirred for 30 h at 110° C. under N₂, cooled to room temperature and filtered through a pad of celite. The celite was washed with CH₂Cl₂ (3×20 ml). The combined filtrates were evaporated to dryness under reduced pressure and the residue purified by flash column chromatography (silica-gel, CH₂Cl₂/ethyl acetate 9:1) giving the title compound as a creamy solid (0.016 g, 25%). $^1$H NMR (300 MHz, CDCl$_3$) 8.17 (s, 1H), 8.06 (s, 1H), 7.46 (d, J=8.75 Hz, 1H), 6.94 (d, J=8.75 Hz, 1H), 6.4 (s, 2H), 3.97 (s, 3H), 3.95 (s, 3H), 3.77 (s, 3H), 3.68 (s, 6H).

(ii) 7-Amino-6-methoxy-2-(1-methyl-1H-pyrazol-4-yl)-3-(3,4,5-trimethoxyphenylthio)benzofuran To a mixture of the product from the previous reaction (0.016 g, 0.034 mmol) in ethanol (10 ml) 10% palladium on carbon (30 mg) was added under N$_2$. The resulting suspension was stirred for 30 min under H$_2$ balloon than filtered through a celite pad. The celite was washed with CH$_2$Cl$_2$ (20 ml) and combined filtrates evaporated to dryness under reduced pressure. The residue was purified by flash column chromatography (silica-gel, CH$_2$Cl$_2$/ethyl acetate 9:1) giving the title compound as a colorless solid. $^1$H NMR (300 MHz, CDCl$_3$) 8.12 (s, 1H), 8.07 (s, 1H), 6.79 (s, 2H), 6.4 (s, 2H), 4.02 broad s, 2H), 3.94 (s, 3H), 3.88 (s, 3H), 3.75 (s, 3H), 3.65 (s, 6H).

Example 7 a) Preparation of 7-Fluoro-6-methoxy-2-(1-methyl-1H-pyrazol-4-yl)-benzofuran-3-yl]-(3,4,5-trimethoxyphenyl)-methanone (entry 41, Table 1)

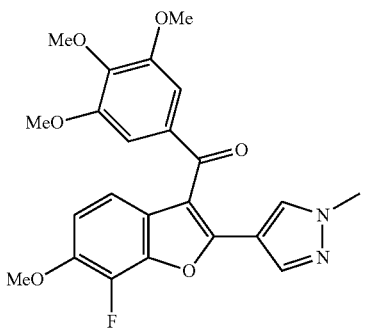

(i) 2,4-Dimethoxy-3-fluoro-nitrobenzene

A freshly prepared solution of sodium methoxide [0.58 g (25 mmol) of sodium dissolved in 3 mL of anhydrous methanol] was added dropwise to a solution of 2 g (11.2 mmol) of 1,2,3-trifluoro-4-nitrobenzene in 30 mL of anhydrous methanol under nitrogen at +4° C. The resulting mixture was stirred overnight at room temperature and quenched with 1 M aqueous citric acid (0.1 eq) and methanol was evaporated under reduced pressure. The residue was taken up with ether, washed with 1 M citric acid, brine and dried over anhydrous magnesium sulfate and filtered off. The filtrate was evaporated under reduced pressure to give 2.2 g (99% yield) of the crude product, which was purified by crystallisation from hexane. H$^1$ NMR (CDCl$_3$) 3.95 (s, 3H, OMe); 4.06 (d, 3H, J=1.6 Hz); 6.72 (dd, 1H, CH, J=9.4 Hz, J=7.5 Hz) 7.72 (dd, 1H, CH, J=9.4 Hz, J=2.23 Hz).

(ii) 2,4-Dimethoxy-3-fluoro-iodobenzene

A mixture of 1.81 g (9 mmol) of above product and 0.24 g of 10% palladium on charcoal in 30 mL of ethanol/ethyl acetate (1:1) was stirred under hydrogen for 5 hours. When the reduction was completed, the catalyst was collected on celite over a glass frit via filtration. The filtrate was evaporated to dryness giving 1.54 g (100% yield) of pure 2,4-dimethoxy-3-fluoro-aniline as an oil. This was dissolved in 30 mL of water/conc. hydrochloric acid chilled in an ice-salt bath and treated with a cold solution of 0.65 g (9.4 mmol) of sodium nitrite in 2 mL of water. The resulting solution was stirred for 15 minutes and then 1.51 g (9.1 mmol) of potassium iodide in 5 mL of water was added dropwise. The resulting mixture was stirred for 2 hours at room temperature and the product was taken up by extraction with ether (3×20 mL). The organic phase was washed with 10% aqueous sodium metabisulfite, brine, and dried over anhydrous magnesium sulfate and filtered off. Evaporation of the solvent and purification by flash column chromatography gave 1.26 g (50%) of pure product as a colourless crystals. H$^1$NMR (CDCl$_3$) 3.85 (s, 3H, MeO); 3.922 (d, 3H, MeO, J=1.43); 6.5 (tr, 1H, CH, J=8.63); 7.4 (dd, 1H CH, J=8.63, J=2.31).

(iii) 4-(2,4-Dimethoxy-3-fluoro-phenylethynyl)-1-methyl-1H-pyrazole

To a mixture of (0.95 mmol) of 2,4-dimethoxy-3-fluoro-iodo benzene, 0.122 g (1.15 mmol) of 4-ethynyl-1-methyl-1H-pyrazole, 0.028 g (0.04 mmol) of dichlorobis(triphenylphosphine)palladium (II) and 8 mg (0.042 mmol) of copper (I) iodide 4 mL of anhydrous acetonitrile and 2 mL of triethylamine were added under nitrogen atmosphere at room temperature. The resulting mixture was stirred for 1 hour, when TLC indicated a consumption of the iodobenzene. The solvent was evaporated under reduced pressure and the residue purified by flash column chromatography (silica gel; dichloromethane:ethyl acetate 9:1) to give the title compound in an 86% yield as creamy crystals. H$^1$ NMR (CDCl$_3$) 3.88 (s, 3H, Me); 3.89 (s, 3H, MeO); 4.05 (d, 3H, MeO, J=1.34 Hz); 6.62 (tr, 1H, CH, J=8.2 Hz); 7.12 (dd, 1H, CH, J=8.2 Hz, J=2.55 Hz); 7.53 (s, 1H, CH pyr); 7.62 s, 1H, CH pyr).

(iv) 4-(3-Iodo-6-methoxy-7-fluoro-benzofuran-2-yl)-1-methyl-1H-pyrazole

A mixture of (0.45 mmol) of above product and 0.21 g (0.543 mmol) of bis(pyridine) iodonium tetrafluoroborate in 3 mL of anhydrous tetrahydrofuran was refluxed for 1 hour under nitrogen atmosphere. After cooling to room temperature the reaction mixture was diluted to 50 mL with ethyl acetate, washed with 5% aqueous sodium metabisulfite, water, brine and dried over anhydrous magnesium sulfate and filtered off. Evaporation of the filtrate yielded 0.17 g of crude product which purified by flash column chromatography (silica gel, dichloromethane) provided the title compound in 90% yield as creamy crystals. H$^1$NMR (CDCl$_3$) 3.95 (s, 3H, Me); 3.98 (s, 3H, MeO); 6.9-7.02 (m, 2H, CH); 8.25 (m, 2H CH pyr).

(v) 7-Fluoro-6-methoxy-2-(1-methyl-1H-pyrazol-4-yl)-benzofuran-3-yl]-(3,4,5-trimethoxyphenyl)-methanone To a mixture of 0.07 g (0.187 mmol) of above product in 2 mL of anhydrous tetrahydrofuran 0.102 mL (0.206 mmol) of 2M isopropylmagnesium chloride was added dropwise at −78° C. under nitrogen. The resulting mixture was stirred for one hour, while the temperature of the bath was kept between −78 to −50° C. then 0.086 g (0.374 mmol) of 3,4,5-trimethoxybenzoyl chloride was added and the resulting mixture was allowed to warm to 0° C. with stirring. The mixture was quenched with saturated ammonium chloride. The product was taken up with ethyl acetate (20 mL) washed with brine and dried over anhydrous magnesium sulfate. Evaporation of the filtrate and purification by flash column chromatography (silica gel, acetonitrile/dichloromethane 9:1) gave 0.011 g (13.4% yield) of pure product as an yellowish solid. H$^1$NMR (CDCl$_3$) 3.77 (s, 6H, MeO)); 3.93 (m, 9H, MeO, Me); 6.82-6.91 (m, 2H, CH); 7.11 (s, 2H, CH); 8.0 (s, 1H, CH pyr); 8.14 (s, 1H, CH pyr).

b) Preparation of 2-{4-[7-Fluoro-6-methoxy-3-(3,4,5-trimethoxybenzoyl)benzofuran-2-yl]-1H-pyrazol-1-yl}acetamide (entry 53 Table 1)

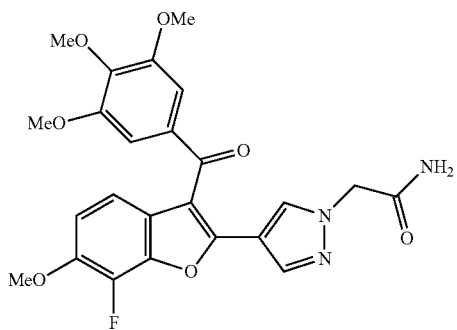 [SMILES: COc1cc(C(=O)c2c(-c3cnn(CC(N)=O)c3)oc3c(F)c(OC)ccc23)cc(OC)c1OC]

(i) 4-(3-Fluoro-2,4-dimethoxyphenylethynyl)-1-(4-methoxybenzyl)-1H-pyrazole

To a stirred solution of 3-fluoro-2,4-dimethoxy-iodobenzene (200 mg, 0.71 mmol) and 4-ethynyl-1-(4-methoxy-benzyl)-1H-pyrazole (180 mg, 0.85 mmol) in dry MeCN (4 ml) and NEt$_3$ (2 ml) was added Pd(Ph$_3$P)$_2$Cl$_2$ (15 mg, 3 mol %) and the reaction vessel was evacuated and backfilled with N$_2$ $_{(g)}$ three times. Copper (I) iodide (6 mol %) was added and the reaction rapidly became dark. Stirring was continued at room temperature for 3 hours, then the crude mixture was concentrated directly onto silica-gel and purified by flash chromatography (silica-gel, eluted sequentially with hexanes:EtOAc, 3:1, 2:1) to give the product as a resin that crystallised slowly upon standing in the freezer (230 mg, 89%). $^1$H-NMR (300 MHz, CDCl$_3$) δ 7.66 (s, 1H), 7.50 (s, 1H), 7.19 (d, J=8.6 Hz, 2H), 7.10 (dd, J=8.7, 2.1 Hz, 1H), 6.87 (d, J=8.6 Hz, 2H), 6.61 (t, J=8.2 Hz, 1H), 5.24 (s, 2H), 4.01 (s, 3H), 3.87 (s, 3H), 3.79 (s, 3H).

(ii) 4-(7-Fluoro-3-iodo-6-methoxy-benzofuran-2-yl)-1-(4-methoxybenzyl)-1H-pyrazole To a stirred solution of the alkyne (110 mg, 0.30 mmol) in dry THF (2.5 ml) was added bis-pyridine-iodonium tetrafluoroborate (120 mg, 0.32 mmol) and the reaction was heated to reflux for 2 hours. After this time a further portion of the iodonium salt (30 mg) was added and heating was continued for 0.5 hours. TLC analysis revealed complete consumption of the starting material and the reaction was cooled, quenched with 10% Na$_2$S$_2$O$_3$ $_{(aq)}$ and extracted with EtOAc. The organic layer was washed with water and brine, dried over MgSO$_4$ and concentrated under reduced pressure to give the product as a white solid (138 mg, 96%). $^1$H-NMR (300 MHz, CDCl$_3$) δ 8.28 (s, 1H), 8.06 (s, 1H), 7.24 (d, J=8.6 Hz, 2H), 7.01-6.93 (m, 2H), 6.90 (d, J=8.6 Hz, 2H), 5.29 (s, 2H), 3.94 (s, 3H), 3.80 (s, 3H).

(iii) 4-(7-Fluoro-6-methoxy-3-(3,4,5-trimethoxybenzoyl)benzofuran-2-yl)-1-(4-methoxybenzyl)-1H-pyrazole A suspension of 4-(7-fluoro-3-iodo-6-methoxy-benzofuran-2-yl)-1-(4-methoxybenzyl)-1H-pyrazole (0.087 g, 0.182 mmol), 3,4,5-trimethoxyphenyl boronic acid (0.058 g, 0.27 mmol), dry K$_2$CO$_3$ (0.075 g, 0.55 mmol) and Pd(PPh$_3$)$_2$Cl$_2$ (0.016 g, 0.014 mmol) in anhydrous anisole (8 ml) was placed in Parr mini bench top reactor (series 4561, 300 ml. The reactor was degassed under reduced pressure and flashed with dry N$_2$ than flashed three times with CO by pressurizing the reactor up to 180 psi and depressurizing. Finally, the reactor was pressurized to 180 psi and stirred at 85±5° C. (the temperature of external oil bath) for ~30 h. The reactor was cooled down to room temperature and the reaction mixture was diluted to 20 ml with CH$_2$Cl$_2$ and filtered through celite. The celite pad was washed with fresh portion of CH$_2$Cl$_2$ (3×20 ml) and combined filtrates were evaporated to dryness under reduced pressure. The residue was purified by flash column chromatography (silica-gel, eluted with CH$_2$Cl$_2$/ethyl acetate 9:1) giving the product of Step 1 as a creamy solid (0.05 g, 50.25%) $^1$H NMR (300 MHz, CDCl$_3$) 7.98 (s, 1H), 7.97 (s, 1H), 7.08 (s, 2H), 6.9-6.97 (m, 1H), 6.82-6.86 (m, 1H), 5.21 (s, 2H), 3.7-3.96 (m, 15H).

(iv) 4-(7-Fluoro-6-methoxy-3-(3,4,5-trimethoxybenzoyl)benzofuran-2-yl)-1H-pyrazole A mixture of the product of Step 1 (0.0483 g 0.088 mmol) and anisole (0.048 ml, 0.44 mmol) in trifluoroacetic acid (5 ml) was refluxed under N$_2$ overnight. After cooling to room temperature, the resulting mixture was evaporated to dryness under reduced pressure and the residue was dissolved in CH$_2$Cl$_2$ (15 ml), washed with 5% aqueous NaHCO3 and dried over anhydrous MgSO4 and filtered off. The filtrate was evaporated to dryness under reduced pressure giving the title compound as a creamy solid (0.037 g, 100%), which was used in next step without further purification. $^1$H NMR (300 MHz, CDCl$_3$) 8.18 (broad s, 2H), 7.12 (s, 2H), 6.83-6.97 (m, 2H), 3.7-3.99 (m, 12H).

(v) 2-{4-[7-Fluoro-6-methoxy-3-(3,4,5-trimethoxybenzoyl)benzofuran-2-yl]-1H-pyrazol-1-yl}acetamide A mixture of the product of Step 2 (0.037 g, 0.0867 mmol), bromoacetamide (0.02 g, 0.13 mmol) and dry K$_2$CO$_3$ (0.022 g, 0.13 mmol) in anhydrous acetonitrile (1.5 ml) was refluxed for 5 h under N$_2$. After cooling to room temperature the solvent was evaporated to dryness under reduced pressure and the residue was washed with water (5 ml), acetonitrile (3×5 ml) giving pure title compound (0.027 g, 64%) as a colorless solid. $^1$H NMR (300 MHz, DMSO-d$_6$) 8.29 (s, 1H), 7.7 (s, 1H), 7.53 (s, 1H), 7.25 (s, 1H), 7.13 (d, J=8.6 Hz, 1H), 7.1 (s, 2H), 6.97 (d, J=8.6 Hz, 1H), 4.8 (s, 2H), 3.87 (s, 3H), 3.73 (s, 3H), 3.67 (s, 6H).

c) Preparation of 7-Hydroxy-6-methoxy-2-(3-methyl-3H-imidazol-4-yl)-3-(3,4,5-trimethoxybenzoyl)-benzo[b]furan (entry 59, Table 1)

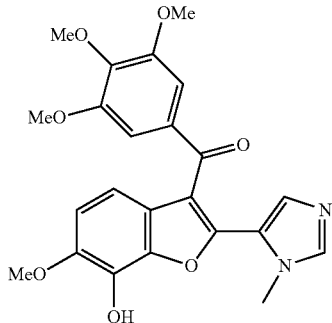 [SMILES: COc1cc(C(=O)c2c(-c3cncn3C)oc3c(O)c(OC)ccc23)cc(OC)c1OC]

(i) 3-Acetoxy-2,4-dimethoxyiodobenzene

To an ice-cooled suspension of acetic acid 2,6-dimethoxyphenyl ester (1.0 g, 5.1 mmol) and silver trifluoroacetate (5.1 mmol) in $CHCl_3$ (16 ml) was added iodine (1.3 g, 5.1 mmol) and the reaction stirred for 1 hour. The crude mixture was filtered through celite to remove the precipitated silver iodide and the filtrate was washed with 10% $Na_2S_2O_3\ _{(aq)}$. An emulsion was formed and the mixture was again passed through celite and the filtrate washed with brine, dried over $MgSO_4$ and concentrated under reduced pressure to give the product as a tan solid (1.57 g, 96%). $^1$H-NMR (300 MHz, $CDCl_3$) δ 7.55 (d, J=8.9 Hz, 1H), 6.54 (d, J=8.9 Hz, 1H), 3.80 (s, 6H), 2.33 (s, 3H).

(ii) Acetic acid 2,6-dimethoxy-3-(3-methyl-3H-imidazol-4-ylethynyl)-phenyl ester To a stirred solution of 3-acetoxy-2,4-dimethoxy-iodobenzene (250 mg, 0.776 mmol) and 5-ethynyl-1-methyl-1H-imidazole (100 mg, 1.09 mmol) in dry MeCN (3 ml) and dry $NEt_3$ (1 ml) was added $Pd(Ph_3P)_2Cl_2$ (20 mg, 3.7 mol %) and the reaction vessel was evacuated and backfilled with $N_2\ _{(g)}$ three times. Copper (I) iodide (15 mg) was added and the reaction was heated to 60° C. and stirred overnight. The resulting dark solution was cooled, diluted with EtOAc and filtered through celite. The filtrate was concentrated onto silica-gel under reduced pressure and the solid residue was purified by flash chromatography (silica-gel, eluted with EtOAc) to give the product as a tan solid (130 mg, 56%). $^1$H-NMR (300 MHz, $CDCl_3$) δ 7.45 (br s, 1H), 7.30 (d, J=8.7 Hz, 1H), 7.30 (br s, 1H), 6.68 (d, J=8.7 Hz, 1H), 3.94 (s, 3H), 3.83 (s, 3H), 3.71 (s, 3H), 2.33 (s, 3H).

(iii) 7-acetoxy-3-iodo-6-methoxy-2-(3-methyl-3H-imidazol-4-yl)benzo[b]furan

To a solution of the alkyne (115 mg, 0.38 mmol) in dry THF (3 ml) was added bispyridine-iodonium tetrafluoroborate (150 mg, 0.40 mmol) and the reaction was refluxed for 1 hour. TLC analysis revealed incomplete consumption of the starting material and a further portion of the iodonium salt (25 mg) was added and the reaction continued for a further 0.5 hours after which time only trace starting material could be detected by TLC analysis. The crude reaction mixture was cooled, diluted with EtOAc and quenched with 10% $Na_2S_2O_3\ _{(aq)}$ and the organic layer was washed with brine, dried over $MgSO_4$ and concentrated onto silica-gel. The solid residue was purified by flash chromatography (silica-gel, eluted with EtOAc) to give the product as a white solid (60 mg, 38%). $^1$H-NMR (300 MHz, $CDCl_3$) δ 7.72 (s, 1H), 7.53 (s, 1H), 7.20 (d, J=8.6 Hz, 1H), 7.02 (d, J=8.6 Hz, 1H), 3.90 (s, 3H), 3.78 (s, 3H), 2.38 (s, 3H).

(iv) 7-Hydroxy-6-methoxy-2-(3-methyl-3H-imidazol-4-yl)-3-(3,4,5-trimethoxybenzoyl)-benzofuran A mixture of the 3-iodo-benzofuran (52 mg, 0.126 mmol), dry potassium carbonate (52 mg, 0.38 mmol), 3,4,5-trimethoxyphenyl-boronic acid (53 mg, 0.25 mmol) and $Pd(Ph_3P)_4$ (20 mg, 14 mol %) in dry anisole (12 ml) was placed in a high-pressure reaction vessel and charged with a carbon monoxide atmosphere (180 psi). The reaction vessel was heated to 90° C. for 70 hours. After this time the solvent had completely evaporated filtrate concentrated onto silica-gel and purified by flash chromatography (silica-gel, eluted sequentially with EtOAc:$CH_2Cl_2$ 1:4, 1:2). The crude product acetate (39 mg) was stirred in MeOH (2 ml) containing $K_2CO_3\ _{(s)}$ (20 mg) to liberate the free phenol. The reaction was quenched with saturated $NH_4Cl_{(aq)}$ and extracted with $CH_2Cl_2$. The organic layer was washed with brine, dried over $MgSO_4$ and concentrated under reduced pressure to give a residue that was applied to a preparative TLC plate and eluted with a 3:1 mixture of $CH_2Cl_2$: EtOAc. The product thus obtained (12 mg) was contaminated with ~15% of the non-carbonyl inserted material and was further purified by crystallisation from EtOAc and hexane to give the desired compound as a yellow solid (7 mg, 13%). $^1$H-NMR (300 MHz, $CDCl_3$) δ 7.56 (br s, 2H), 7.11 (s, 2H), 7.02 (d, J=8.6 Hz, 1H), 6.93 (d, J=8.6 Hz, 1H), 3.96 (s, 3H), 3.89 (s, 3H), 3.75 (s, 6H). MS (ESI) m/z (%): 439 (M+H$^+$, 100).

Example 8

A series of compounds of the invention were prepared by Suzuki coupling to a C-2 bromides (see Scheme 2)

a) Preparation of 2-Bromo-3-(3,4,5-trimethoxybenzoyl)-6-methoxy-benzofuran

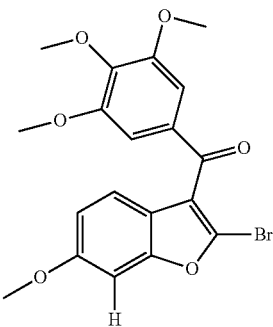 [SMILES: COc1ccc2c(C(=O)c3cc(OC)c(OC)c(OC)c3)c(Br)oc2c1]

(i) 2-t-Butyldimethylsilanyl-3-(t-butyldimethylsilanyloxymethylene)-6-methoxy-benzofuran A suspension of 2-iodo-5-methoxyphenol (1.1 g, 4.41 mmol), 1-(tert-butyl-dimethylsilanyl)-3-(tert-butyl-dimethyl-silanyloxy)-propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to give the title compound as a yellow oil; (1.09 g, 87%); $^1$H NMR (300 MHz, $CDCl_3$) δ 7.52 (d, 1H, J=8.57 Hz), 6.97 (d, 1H, J=2.15 Hz), 6.83 (dd, 1H, J=8.54, 2.18 Hz), 4.81 (s, 2H, $CH_2$), 3.83 (s, 3H, OMe), 0.93 (s, 9H), 0.91 (s, 9H), 0.34 (s, 6H), 0.11 (s, 6H).

(ii) 2-t-Butyldimethylsilyl-3-formyl-6-methoxy-benzofuran

To a solution of 2-t-butyldimethylsilanyl-3-(t-butyldimethylsilanyloxymethylene)-6-methoxy-benzofuran (1.09 g, 2.69 mmol) in methanol (100 mL) was added concentrated hydrochloric acid (200 μL) and the reaction was stirred for 30 minutes (tlc), quenched with triethylamine (2 mL) and the solvent removed by distillation under vacuum. The residue was dissolved in dichloromethane (20 mL), washed with water (10 mL), dried over magnesium sulphate, concentrated under vacuum and co-distilled with toluene (20 mL); 1H NMR (300 MHz, CDCl$_3$)-7.57 (d, 1H, J=8.57 Hz), 7.00 (d, 1H, J=2.17 Hz), 6.86 (dd, 1H, J=8.55, 2.22 Hz), 4.81 (s, 2H, CH2), 3.84 (s, 3H, OMe), 0.94 (s, 9H), 0.37 (s, 6H). The crude yellow paste (~985 mg) was dissolved in dry dichloromethane (4 mL) and added to a stirred solution of Collin's reagent [chromium trioxide (1.01 g), pyridine (1.65 mL) in dry dichloromethane (30 mL)]. The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil which crystallised on standing; (485 mg, 68%); $^1$H NMR (300 MHz, CDCl$_3$) δ 10.25 (s, 1H, CHO), 8.06 (d, 1H, J=8.61 Hz), 7.03 (d, 1H, J=2.16 Hz), 6.95 (dd, 1H, J=8.60, 2.19 Hz), 3.84 (s, 3H, OMe), 0.97 (s, 9H), 0.46 (s, 6H); $^{13}$C NMR (75 MHz, CDCl$_3$) δ 186.91 (CHO), 174.18, 159.19, 159.17, 132.82, 122.77, 117.34, 113.56, 95.36, 55.60, 27.04, 17.09, −5.24.

(iii) 2-t-Butyldimethylsilyl-3-(3,4,5-trimethoxybenzoyl)-6-methoxy-benzofuran

To a stirred solution of 3,4,5-trimethoxy-iodobenzene (377 mg, 1.27 mmol) in dry tetrahydrofuran (1 mL) at −78° C. under nitrogen was added n-butyllithium (795 μL, 1.59 mmol, 2M solution in cyclohexane) and the reaction mixture was stirred at this temperature for 40 minutes. After this time a solution of 2-t-butyldimethylsilyl-3-formyl-6-methoxy-benzofuran (310 mg, 1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulphate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (tlc) and then loaded onto silica (10 g) and purified by flash chromatography (silica gel, eluent=hexane/diethyl ether/triethylamine, 90:9:1) to afford the title compound as a light yellow paste that crystallised on standing; (232 mg, 48%); $^1$H NMR (300 MHz, CDCl$_3$) δ 7.14 (s, 2H, benzoyl Hs), 7.05 (d, 1H, J=2.45 Hz), 6.77 (dd, 1H, J=8.76, 2.17 Hz), 6.56 (d, 1H, J=8.38 Hz), 3.94 (s, 3H, OMe), 3.85 (s, 6H, 2×OMe), 3.78 (s, 3H, OMe), 1.00 (s, 9H), 0.28 (s, 6H); $^{13}$C NMR (75 MHz, CDCl$_3$) δ 190.51 (CO), 164.77, 158.23, 158.12, 152.64, 142.35, 133.19, 131.37, 123.19, 121.04, 119.63, 112.26, 107.03, 104.96, 95.00, 60.47, 55.81, 55.60, 55.13, 26.43, 17.29, −6.09.

(iv) 3-(3,4,5-trimethoxybenzoyl)-6-methoxy-benzofuran

To a stirred solution of 2-t-butyldimethylsilyl-3-(3,4,5-trimethoxy-benzoyl)-6-methoxy-benzofuran (30 mg, 0.066 mmol) in tetrahydrofuran (1 mL) was added tetrabutylammoniumfluoride (76.5 μL, 0.076 mmol, 1M solution in tetrahydrofuran). The reaction mixture was stirred at room temperature for 20 minutes (tlc), diluted with ethyl acetate (10 mL) and washed with 1M hydrochloric acid (5 mL). The organic layer was dried over magnesium sulphate and the solvent was removed under vacuum. The crude product was purified by flash chromatography (silica gel, eluent=hexane/diethyl ether; 7:3) to afford the title product as a creamy crystalline solid; (19.3 mg, 86%); $^1$H NMR (300 MHz, CDCl$_3$) δ 8.02 (d, 1H, J=8.97 Hz), 8.01 (s, 1H, C$_2$H), 7.14 (s, 2H, benzoyl Hs), 7.05 (d, 1H, J=2.11 Hz), 7.00 (dd, 1H, J=8.63, 2.11 Hz), 3.93 (s, 3H, OMe), 3.90 (s, 6H, 2×OMe), 3.87 (s, 3H, OMe); $^{13}$C NMR (75 MHz, CDCl$_3$) δ 188.71 (CO), 158.64, 156.31, 152.82, 150.22, 141.72, 133.97, 122.58, 120.87, 118.12, 113.11, 106.07, 95.53, 60.63, 55.99, 55.40.

(v) 2-Bromo-3-(3,4,5-trimethoxybenzoyl)-6-methoxy-benzofuran

To a stirred solution of 2-t-butyldimethylsilanyl-3-(3,4,5-trimethoxybenzoyl)-6-methoxy-benzofuran (200 mg, 0.44 mmol) in 1,2-dichloroethane (2 mL) at 0° C. under nitrogen was added bromine (23 μl, 0.44 mmol) dropwise and the reaction mixture was stirred for 10 minutes. After this time the reaction was quenched with saturated sodium thiosulphate solution, extracted with ethyl acetate (20 mL), dried over magnesium sulphate and the solvent removed by distillation under vacuum. The crude product was re-crystallised from acetonitrile to afford the title compound as a colourless crystalline solid; (69 mg, 37%); $^1$H NMR (300 MHz, CDCl$_3$) δ 7.45 (d, 1H, J=8.78 Hz), 7.15 (s, 2H, benzoyl-Hs), 7.01 (d, 1H, J=2.18 Hz), 6.90 (dd, 1H, J=8.74, 2.27 Hz), 3.94 (s, 3H, OMe), 3.85 (s, 9H, 3×OMe); $^{13}$C NMR (75 MHz, CDCl$_3$) δ 188.21 (CO), 158.29, 155.80, 152.72, 142.55, 131.99, 130.69, 120.98, 119.97, 119.67, 112.90, 107.00, 95.30, 60.67, 55.94, 55.43.

b) Preparation of 2-Bromo-7-acetoxy-3-(3,4,5-trimethoxybenzoyl)-6-methoxy-benzofuran

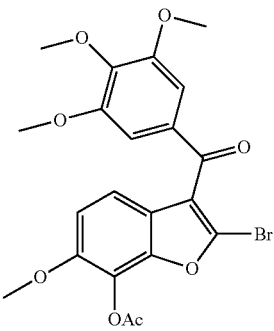 [SMILES: COc1cc(C(=O)c2c(Br)oc3c(OC(C)=O)c(OC)ccc23)cc(OC)c1OC]

(i) 2-t-Butyldimethylsilanyl-3(t-butyldimethylsilanyloxymethylene)-6-methoxy-7-isopropoxy-benzofuran A suspension of 2-isopropoxy-3-methoxy-5-iodophenol (4.41 mmol), 1-(tert-butyl-dimethylsilanyl)-3-(tert-butyl-dimethyl-silanyloxy)-propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to afforded the title compound a yellow oil; (1.45 g, 96%); $^1$H NMR (300 MHz, CDCl$_3$) δ 7.24 (d, 1H, J=8.45 Hz), 6.88 (d, 1H, J=8.47 Hz), 4.80 (s, 2H, CH2), 4.73 (m, 1H), 3.88 (s, 3H, OMe), 1.36 (d, 6H, J=6.17 Hz), 0.94 (s, 9H), 0.92 (s, 9H), 0.35 (s, 6H), 0.12 (s, 6H).

(ii) 2-t-Butyldimethylsilanyl-3-formyl-6-methoxy-7-isopropoxy-benzofuran

To a solution of 2-t-butyldimethylsilyl-3-(t-butyldimethyl-silyloxymethylene)-6-methoxy-7-isopropoxy-benzofuran (2.69 mmol) in methanol (100 mL) was added concentrated hydrochloric acid (200 µL) and the reaction was stirred for 30 minutes (tlc), quenched with triethylamine (2 mL) and the solvent removed by distillation under vacuum. The residue was dissolved in dichloromethane (20 mL), washed with water (10 mL), dried over magnesium sulphate, concentrated under vacuum and co-distilled with toluene (20 mL). The crude product was dissolved in dry dichloromethane (4 mL) and added to a stirred solution of Collin's reagent [chromium trioxide (1.01 g), pyridine (1.65 mL) in dry dichloromethane (30 mL)]. The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil; (503 mg, 48%); $^1$H NMR (300 MHz, CDCl$_3$) δ 10.25 (s, 1H, CHO), 7.79 (d, 1H, J=8.45 Hz), 6.98 (d, 1H, J=8.46 Hz), 4.65 (m, 1H), 3.89 (s, 3H, OMe), 1.35 (d, 6H, J=6.17 Hz), 0.97 (s, 9H), 0.45 (s, 6H).

(iii) 2-t-Butyldimethylsilanyl-3(3,4,5-trimethoxybenzoyl)-6-methoxy-7-isopropoxy-benzofuran To a stirred solution of 3,4,5-trimethoxy-iodobenzene (377 mg, 1.27 mmol) in dry tetrahydrofuran (1 mL) at −78° C. under nitrogen was added n-butyllithium (795 µL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxy-benzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulphate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (tlc) and then loaded onto silica (10 g) and purified by flash chromatography (silica gel, eluent=hexane/diethyl ether/triethylamine, 90:9:1) to afford the title compound as a light yellow oil; (498 mg, 69%); $^1$H NMR (300 MHz, CDCl$_3$) δ 7.14 (s, 2H, benzoyl Hs), 6.81 (d, 1H, J=8.64 Hz), 6.77 (d, 1H, J=8.64 Hz) 4.74 (m, 1H), 3.93 (s, 3H, OMe), 3.86 (s, 3H, OMe), 3.78 (s, 6H, 2×OMe), 1.39 (d, 6H, J=6.14 Hz), 1.01 (s, 9H), 0.26 (s, 6H).

(iv) 3-(3,4,5-trimethoxybenzoyl)-6-methoxy-7-isopropoxy-benzofuran

To a stirred solution of 2-t-butyldimethylsilyl-3-(3,4,5-trimethoxy-benzoyl)-6-methoxy-7-isopropoxy-benzofuran (0.066 mmol) in tetrahydrofuran (1 mL) was added tetrabutylammoniumfluoride (76.5 µL, 0.076 mmol, 1M solution in tetrahydrofuran). The reaction mixture was stirred at room temperature for 20 minutes (tlc), diluted with ethyl acetate (10 mL) and washed with 1M hydrochloric acid (5 mL). The organic layer was dried over magnesium sulphate and the solvent was removed under vacuum. The crude product was purified by flash chromatography (silica gel, eluent=hexane/diethyl ether; 7:3) to afford the title compound as a light yellow paste (23 mg) that was used directly in the next step. $^1$H NMR (300 MHz, CDCl$_3$) δ 8.00 (s, 1H, C$_2$H), 7.78 (d, 1H, J=8.60 Hz), 7.15 (s, 2H, benzoyl Hs), 7.04 (d, 1H, J=8.61 Hz), 4.73 (m, 1H), 3.93 (s, 3H, OMe), 3.92 (s, 3H, OMe), 3.90 (s, 6H, 2×OMe), 1.37 (d, 6H, J=6.14 Hz).

(v) 3-(3,4,5-Trimethoxybenzoyl)-6-methoxy-7-hydroxy-benzofuran

A solution of 3-(3,4,5-trimethoxybenzoyl)-6-methoxy-7-isopropoxy-benzofuran (23 mg, 0.058 mmol, co-distilled with toluene before use) in dry dichloromethane (1 mL) was treated with solid aluminium chloride (16 mg, 0.116 mmol). The reaction mixture was stirred for 20 minutes at room temperature (tlc) then quenched with saturated ammonium chloride solution and extracted with ethyl acetate (10 mL). The organic layer was washed with water (5 mL), dried over magnesium sulphate and concentrated under vacuum. The crude product was purified by flash chromatography (silica gel, eluent=hexane/diethyl ether/ethyl acetate; 80:19:1) to afford the title compound as a creamy white crystalline solid; (18 mg, 86%); $^1$H NMR (300 MHz, CDCl$_3$) δ 8.04 (s, 1H, C$_2$H), 7.63 (d, 1H, J=8.53 Hz), 7.14 (s, 2H, benzoyl Hs), 7.02 (d, 1H, J=8.38 Hz), 3.97 (s, 3H, OMe), 3.93 (s, 3H, OMe), 3.89 (s, 6H, 2×OMe); $^{13}$C NMR (75 MHz, CDCl$_3$) δ 188.73 (CO), 152.82, 151.24, 144.54, 143.30, 141.76, 133.97, 130.87, 120.92, 120.62, 112.43, 109.16, 106.06, 60.62, 56.85, 55.97.

(vi) 2-(t-butyldimethylsilanyloxy)-7-acetoxy-3-(3,4,5-trimethoxybenzoyl)-6-methoxy-benzofuran To a stirred solution of 2-(t-butyldimethylsilyloxy)-7-isopropoxy-3-(3,4,5-trimethoxybenzoyl)-6-methoxy-benzofuran (160 mg, 0.31 mmol) in dry DCM (2 mL) at room temperature under nitrogen was added solid aluminium trichloride (83 mg, 0.62 mmol) and the reaction mixture was stirred for 15 minutes (tlc). The reaction was quenched with a saturated solution of ammonium chloride, extracted with dichloromethane and dried over magnesium sulphate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20); (134 mg, 84%); $^1$H NMR (300 MHz, CDCl$_3$) δ 7.14 (s, 2H, benzoyl Hs), 6.98 (d, 1H, J=8.72 Hz), 6.85 (d, 1H, J=8.72 Hz), 3.93 (s, 3H, OMe), 3.86 (s, 3H, OMe), 3.80 (s, 6H, 2×OMe), 2.41 (s, 3H), 0.99 (s, 9H), 0.25 (s, 6H).

(vii) 2-Bromo-7-acetoxy-3-(3,4,5-trimethoxybenzoyl)-6-methoxy-benzofuran

To a stirred solution of 2-t-butyldimethylsilanyl-7-acetoxy-3-(3,4,5-trimethoxybenzoyl)-6-methoxy-benzofuran (120 mg, 0.44 mmol) in 1,2-dichloroethane (1 mL) at room temperature under nitrogen was added bromine (12 μl, 0.44 mmol) dropwise and the reaction mixture was stirred at this temperature for 10 minutes. After this time the reaction was quenched with saturated sodium thiosulphate solution, extracted with ethyl acetate (20 mL), dried over magnesium sulphate and the solvent removed by distillation under vacuum. The crude product was purified by silica gel column chromatography (eluent=Hexane:diethyl ether; 8:2-7:3) to afford the title compound as a colourless crystalline solid; (91 mg, 81%); $^1$H NMR (300 MHz, CDCl$_3$) δ 7.40 (d, 1H, J=8.70 Hz), 7.14 (s, 2H, benzoyl-Hs), 6.98 (d, 1H, J=8.75 Hz), 3.94 (s, 3H, OMe), 3.89 (s, 3H, OMe), 3.86 (s, 6H, 2×OMe), 2.43 (s, 3H); $^{13}$C NMR (75 MHz, CDCl$_3$) δ 187.95 (CO), 167.71, 152.75, 149.54, 147.49, 142.59, 131.92, 131.80, 123.91, 121.84, 119.89, 117.72, 109.89, 106.92, 60.69, 56.61, 56.00, 20.09.

General Procedure for Preparation of 2-heteroaryl substituted benzofurans from 2-bromo-3-(3,4,5-trimethoxybenzoyl)-6-methoxy-benzofuran by Suzuki coupling To a stirred solution of 2-bromo-3-(3,4,5-trimethoxybenzoyl)-6-methoxy-benzofuran (28 mg, 0.066 mmol) and a boronic acid of the heteroaryl (0.20 mmol), in 1,4-dioxane (2 mL) at 90° C. was added tetrakis-triphenylphosphine palladium (10 mg, 0.01 mmol) followed by the addition of a solution of sodium bicarbonate (28 mg, 0.33 mmol) in distilled water (1 mL). The reaction mixture turned red after 5 minutes. After 25 minutes (tlc) the reaction mixture was brought to room temperature and diluted with ethyl acetate (10 mL). The organic layer was washed with water, dried over magnesium sulphate and the solvent was removed by distillation under vacuum. The residue was purified by PTLC (eluent=hexane/ethyl acetate, 4:6).

c) Preparation of 2-(6-Methoxy-pyridin-3-yl)-3-(3,4,5-trimethoxybenzoyl)-6-methoxy-benzofuran (entry 11, Table 1)

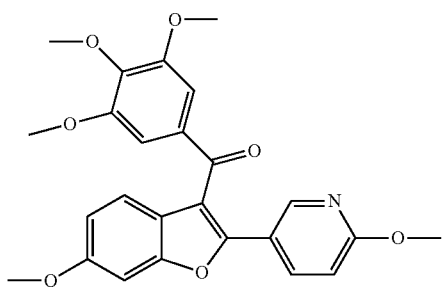

Application of the general procedure for Suzuki couplings (above) with 2-methoxy-5-pyridine boronic acid (31 mg, 0.20 mmol) gave the title compound as a yellow-green solid; (17 mg, 57%); $^1$H NMR (300 MHz, CDCl$_3$) δ 8.47 (d, 1H, J=2.36 Hz), 7.80 (dd, 1H, J=8.71, 2.42 Hz), 7.45 (d, 1H, J=8.70 Hz), 7.11 (s, 2H, benzoyl Hs), 7.07 (d, 1H, J=2.14 Hz), 6.89 (dd, 1H, J=8.71, 2.14 Hz), 6.66 (d, 1H, J=8.74 Hz) 3.89 (s, 3H, OMe), 3.87 (s, 6H, 2×OMe), 3.71 (s, 6H, 2×OMe); $^{13}$C NMR (75 MHz, CDCl$_3$) δ 190.10 (CO), 164.01, 158.40, 154.53, 154.24, 152.63, 146.54, 142.41, 137.52, 132.16, 121.48, 121.17, 119.34, 115.50, 112.59, 110.27, 107.09, 95.29, 60.60, 55.82, 55.43, 55.39 d) Preparation of 6-Methoxy-2-(1-methyl-1H-pyrazol-4-yl)-3-(3,4,5-trimethoxybenzoyl)benzo[b]furan (entry 12, Table 1)

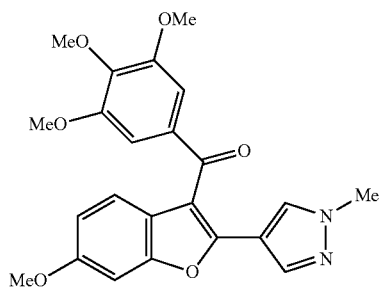 [SMILES: COc1ccc2c(C(=O)c3cc(OC)c(OC)c(OC)c3)c(-c3cnn(C)c3)oc2c1]

Application of the general procedure to 1-methyl-4-(4,4,5,5-tetramethyl-[1,3,2]dioxaborolan-2-yl)-1H-pyrazole afforded the title compound as a yellow crystalline solid; (13 mg, 65%); $^1$H NMR (300 MHz, CDCl$_3$) δ 8.16 (s, 1H), 8.00 (s, 1H), 7.13 (s, 2H, benzoyl Hs), 7.09 (d, 1H, J=8.63 Hz), 7.04 (d, 1H, J=2.12 Hz), 6.78 (dd, 1H, J=8.6, 2.12 Hz), 3.93 (s, 3H), 3.92 (s, 3H), 3.86 (s, 3H), 3.77 (s, 6H).

e) Preparation of 2-(3-Thiophenyl)-3-(3,4,5-trimethoxybenzoyl)-6-methoxy-benzo[b]furan (entry 18, Table 1)

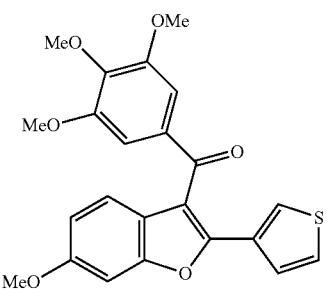

Application of the general procedure to thiophene-3-boronic acid afforded the title compound as a yellow paste; (9 mg, 60%); $^1$H NMR (300 MHz, CDCl$_3$) δ 7.84 (dd, 1H, J=2.99, 1.27 Hz), 7.35 (d, 1H, J=8.72 Hz)), 7.33 (dd, 1H, J=5.15, 1.26 Hz), 7.25 (dd, 1H, J=5.10, 2.99 Hz), 7.15 (s, 2H, benzoyl Hs), 7.06 (d, 1H, J=2.15 Hz), 6.87 (dd, 1H, J=8.70, 2.26 Hz), 3.90 (s, 3H, OMe), 3.87 (s, 3H, OMe), 3.73 (s, 6H, 2×OMe); $^{13}$C NMR (75 MHz, CDCl$_3$) δ 190.11 (CO), 158.30, 154.04, 152.93, 152.63, 142.32, 132.56, 130.55, f) Preparation of 2-(3,5-dimethylisoxazol-4-yl)-7-hydroxy-3-(3,4,5-trimethoxy-benzoyl)-6-methoxy-benzo[b]furan (entry 25, Table 1)

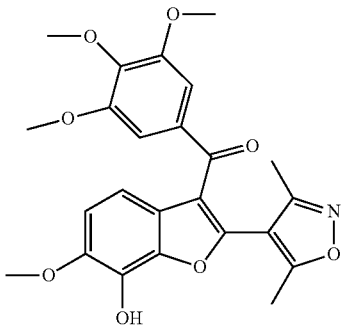 [SMILES: COc1cc(C(=O)c2c(-c3c(C)noc3C)oc3c(O)c(OC)ccc23)cc(OC)c1OC]

Application of the general procedure to 3,5-dimethylisoxazole-4-boronic acid afforded the title compound as a yellow paste; (4 mg, 9%); $^1$H NMR (300 MHz, CDCl$_3$) δ 7.10 (d, 1H, J=8.55 Hz), 7.09 (s, 2H, benzoyl Hs), 6.94 (d, 1H, J=8.64 Hz), 5.74 (bs, 1H, OH), 3.96 (s, 3H, OMe), 3.90 (s, 3H, OMe), 3.77 (s, 6H, 2×OMe), 2.32 (s, 3H), 2.28 (s, 3H).

g) Preparation of 2-(4-N-isobutyl-pyrazolyl)-7-hydroxy-3-(3,4,5-trimethoxy-benzoyl)-6-methoxy-benzo[b]furan (entry 26, Table 1)

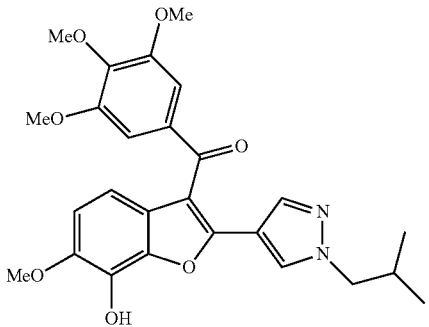 [SMILES: COc1cc(C(=O)c2c(-c3cnn(CC(C)C)c3)oc3c(O)c(OC)ccc23)cc(OC)c1OC]

To a stirred solution of 2-bromo-7-acetoxy-3-(3,4,5-trimethoxybenzoyl)-6-methoxy-benzo[b]furan (40 mg, 0.084 mmol) and 1-isobutyl-4 (4,4,5,5,tetramethyl-1,2,3-dioxaborolon-2-yl)1H-pyrazole (42 mg, 0.016 mmol), in 1,4-dioxane (3 mL) at 90° C. was added tetrakis-triphenylphosphine palladium (8 mg, 0.008 mmol) followed by the addition of a solution of sodium bicarbonate (40 mg, 0.48 mmol) in distilled water (1 mL). The reaction mixture turned brown after 5 minutes. After 25 minutes (tlc) the reaction mixture was brought to room temperature and diluted with ethyl acetate (10 mL). The organic layer was washed with water, the solvent was removed by distillation under vacuum and crude residue was treated with potassium carbonate (100 mg, excess) in methanol (10 mL). The residue was purified by PTLC (eluent=hexane/ethyl acetate, 4:6) to give the title compound as a crystalline yellow solid; (26 mg, 65%); $^1$H NMR (300 MHz, CDCl$_3$) δ 8.07 (s, 1H), 8.02 (s, 1H), 7.14 (s, 2H, benzoyl Hs), 6.81 (d, 1H, J=8.67 Hz), 6.74 (d, 1H, J=8.55 Hz), 3.92 (s, 6H, 2×OMe), 3.91 (d, 2H, J=10.49 Hz), 3.79 (s, 6H, 2×OMe), 2.25-2.16 (m, 1H), 0.89 (d, 6H, J=6.68 Hz).

h) Preparation of 7-Hydroxy-2-(2-thiophenyl)-3-(3,4,5-trimethoxybenzoyl)-6-methoxy-benzo[b]furan (entry 28, Table 1)

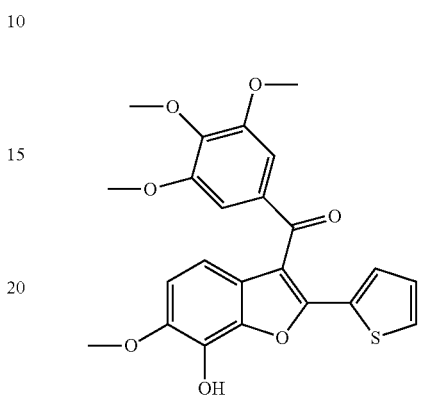

Prepared by application of the general procedure for Suzuki couplings (above) thiophene-2-boronic and 2-bromo-7-acetoxy-3-(3,4,5-trimethoxybenzoyl)-6-methoxy-benzo[b]furan; (24 mg, 65%); $^1$H NMR (300 MHz, CDCl$_3$) δ 7.58 (d, 1H, J=2.81 Hz), 7.39 (d, 1H, J=4.27 Hz), 7.16 (s, 2H, benzoyl Hs), 7.01 (t, 1H, J=3.87 Hz), 6.90 (d, 1H, J=8.60 Hz), 6.85 (d, 1H, J=8.60 Hz), 5.71 (bs, 1H, OH), 3.95 (s, 3H, OMe), 3.90 (s, 3H, OMe), 3.75 (s, 6H, 2×OMe).

i) Preparation of 2-(2-thiophene-5-carbaldehyde)-7-hydroxy-3-(3,4,5-trimethoxybenzoyl)-6-methoxy-benzo[b]furan (entry 37, Table 1)

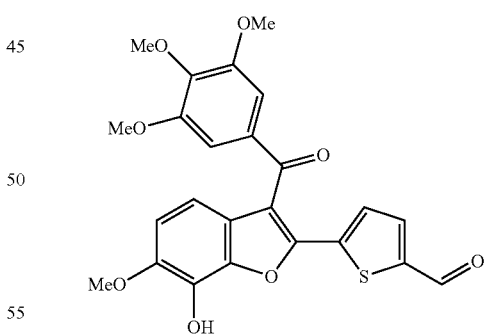

Prepared by application of the general procedure for Suzuki couplings (above) to 5-formyl-thiophene-2-boronic and 2-bromo-7-acetoxy-3-(3,4,5-trimethoxybenzoyl)-6-methoxy-benzo[b]furan. $^1$H NMR (300 MHz, CDCl$_3$) δ 9.89 (s, 1H, CHO), 7.68 (d, 1H, J=4.16 Hz), 7.65 (d, 1H, J=4.11 Hz), 7.18 (s, 2H, benzoyl Hs), 6.88 (d, 1H, J=8.66 Hz), 6.83 (d, 1H, J=8.67 Hz), 5.78 (bs, 1H, OH), 3.96 (s, 3H, OMe), 3.92 (s, 3H, OMe), 3.77 (s, 6H, 2×OMe).

j) Preparation of 2-(2-furanyl)-7-hydroxy-6-methoxy-3-(3,4,5-trimethoxybenzoyl)benzo[b]furan (entry 36, Table 1)

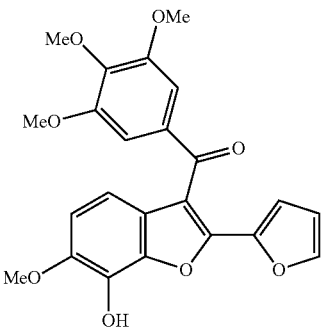

Prepared by application of the general procedure for Suzuki couplings (above) to 5-furanyl-2-boronic and 2-bromo-7-acetoxy-3-(3,4,5-trimethoxybenzoyl)-6-methoxybenzo[b]furan. $^1$H NMR (300 MHz, CDCl$_3$) δ 7.37 (bs, 1H), 7.15 (s, 2H, benzoyl Hs), 6.99 (d, 1H, J=8.66 Hz), 6.99 (bs, 1H), 6.88 (d, 1H, J=8.61 Hz), 6.44 (distorted triplet, 1H, J=2.56 Hz), 5.77 (bs, 1H, OH), 3.94 (s, 3H, OMe), 3.90 (s, 3H, OMe), 3.75 (s, 6H, 2×OMe).

Example 9

Preparation of 7-Hydroxy-2-(2-thiazolyl)-3-(3,4,5-trimethoxybenzoyl)-6-methoxy-benzo[b]furan (entry 44, Table 1)

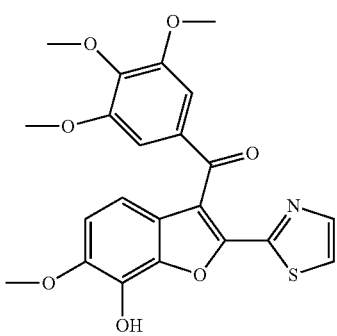 [SMILES: COc1cc(C(=O)c2c(-c3nccs3)oc3c(O)c(OC)ccc23)cc(OC)c1OC]

A dry flask (10 mL) under nitrogen was charged with 2-bromo-7-acetoxy-3-(3,4,5-trimethoxybenzoyl)-6-methoxy-benzo[b]furan (29 mg, 0.06 mmol) and a solution of thiazole zinc bromide (500 μL, 0.5 mmol, 0.5M solution in THF) was added followed by the addition of dichloro-bis-triphenylphosphine palladium catalyst (11 mg, 0.016 mmol) and the reaction mixture was stirred for 5 hours at 60° C. After this time a catalytic amount of copper (I) iodide and lithium chloride was added to the reaction and the amount of solvent was evaporated to approximately half to the original volume and stirring was continued at room temperature for 18 hours. The reaction was quenched with saturated ammonium chloride solution, extracted with dichloromethane (10 mL), dried over magnesium sulphate and the solvent distilled under vacuum. The product was purified by PTLC (eluent=hexane/ethyl acetate; 1:1) to give the title compound as a yellow paste which crystallised by triturating with 2 drops of methanol; (13 mg, 49%); $^1$H NMR (300 MHz, CDCl$_3$) δ 7.85 (d, 1H, J=3.10 Hz), 7.40 (d, 1H, J=3.11 Hz), 7.19 (s, 2H, benzoyl Hs), 6.96 (d, 1H, J=8.60 Hz), 6.91 (d, 1H, J=8.62 Hz), 3.96 (s, 3H, OMe), 3.90 (s, 3H, OMe), 3.74 (s, 6H, 2×OMe).

Example 10

A series of compounds of the invention were prepared by introduction of heteroaryl or heterocyclyl units by nucleophilic substitution of the C-2 bromo group in 2-bromo-7-acetoxy-3-(3,4,5-trimethoxybenzoyl)-6-methoxy-benzo[b]furan (see example 8). These groups are linked to the benzo[b]furan core by a nitrogen in the heteroaryl ring.

a) Preparation of 2-(N-imidazolyl)-7-hydroxy-3-(3,4,5-trimethoxybenzoyl)-6-methoxy-benzo[b]furan (entry 27, Table 1)

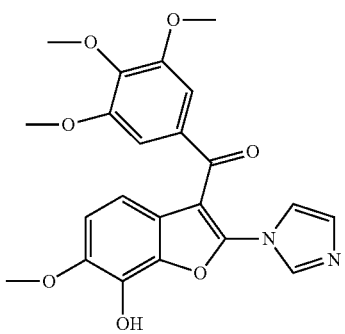 [SMILES: COc1cc(C(=O)c2c(-n3ccnc3)oc3c(O)c(OC)ccc23)cc(OC)c1OC]

A mixture of 2-bromo-7-acetoxy-3-(3,4,5-trimethoxybenzoyl)-6-methoxy-benzo[b]furan (30 mg, 0.063 mmol) and imidazole (60 mg, 0.88 mmol) in a mixture of toluene:triethylamine (3 mL: 2 drops) was refluxed for 4 hours (tlc). Solvent was distilled under vacuum and the crude residue was purified by PTLC (eluent=ethyl-acetate: 1% triethylamine) to give the title compound as a yellow solid; (8 mg, 30%); $^1$H NMR (300 MHz, CDCl$_3$) δ 8.24 (bs, 1H), 7.52 (b, 1H), 7.19 (b, 1H), 7.06 (s, 2H, benzoyl Hs), 6.99 (d, 1H, J=8.60 Hz), 6.93 (d, 1H, J=8.66 Hz), 3.96 (s, 3H, OMe), 3.91 (s, 3H, OMe), 3.76 (s, 6H, 2×OMe).

b) Preparation of 2-(1N-1,2,3-triazolyl)-7-hydroxy-3-(3,4,5-trimethoxybenzoyl)-6-methoxy-benzo[b]furan (entry 35, Table 1)

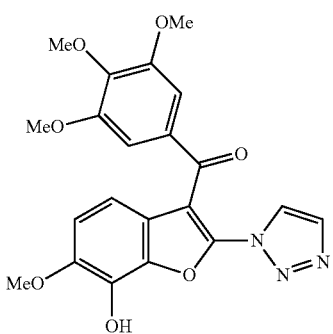 [SMILES: COc1cc(C(=O)c2c(-n3ccnn3)oc3c(O)c(OC)ccc23)cc(OC)c1OC]

This material was prepared according to the procedure outlined above for 2-(N-imidazolyl)-7-hydroxy-3-(3,4,5-trimethoxybenzoyl)-6-methoxy-benzo[b]furan (entry 27, Table 1), above, except the 1,2,3-triazole was used as the nucleophile in place of imidazole. ¹H NMR (300 MHz, CDCl₃) δ 8.47 (d, 1H, J=1.21 Hz), 7.75 (d, 1H, J=1.20 Hz), 7.27 (d, 1H, J=8.60 Hz), 7.18 (d, 1H, J=8.66 Hz), 7.05 (s, 2H, benzoyl Hs), 3.94 (s, 3H, OMe), 3.74 (s, 6H, 2×OMe), 3.73 (s, 3H, OMe).

c) Preparation of 2-(N-pyrazolyl)-7-hydroxy-3-(3,4,5-trimethoxybenzoyl)-6-methoxy-benzo[b]furan (entry 34, Table 1)

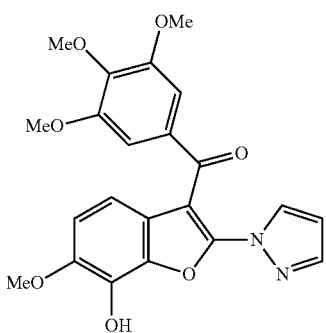

This material was prepared according to the procedure outlined above for 2-(N-imidazolyl)-7-hydroxy-3-(3,4,5-trimethoxybenzoyl)-6-methoxy-benzo[b]furan (entry 27, Table 1), above, except pyridine was used as the solvent in place of toluene, THF and triethylamine and pyrazole was used as the nucleophile in place of imidazole. ¹H NMR (300 MHz, CDCl₃) δ 7.82 (d, 1H, J=2.55 Hz), 7.65 (d, 1H, J=1.51 Hz), 7.18 (d, 1H, J=8.57 Hz), 7.01 (s, 2H, benzoyl Hs), 6.96 (d, 1H, J=8.61 Hz), 6.30 (t, 1H, J=1.88 Hz), 3.96 (s, 3H, OMe), 3.86 (s, 3H, OMe), 3.75 (s, 6H, 2×OMe).

d) Preparation of 2-(1,2,4-triazol-1-yl)-7-hydroxy-3-(3,4,5-trimethoxybenzoyl)-6-methoxy-benzo[b]furan (entry 43, Table 1)

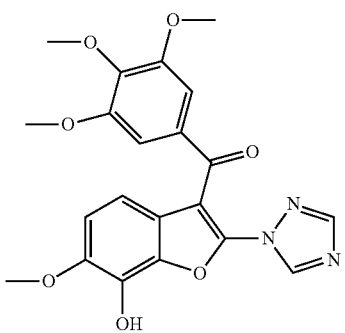 [SMILES: COc1cc(C(=O)c2c(-n3cncn3)oc3c(O)c(OC)ccc23)cc(OC)c1OC]

To a solution of 1,2,4-triazole (22 mg, 0.32 mmol) in dry tetrahydrofuran (2 mL) was added sodium hydride (60%, 24 mg, 0.60 mmol) and resulting suspension was treated with a solution of 2-bromo-7-acetoxy-3-(3,4,5-trimethoxybenzoyl)-6-methoxy-benzo[b]furan (50 mg, 0.10 mmol) in dry toluene (2 mL). The mixture was stirred at reflux for 6 hours (tlc), quenched with saturated ammonium chloride solution, extracted with dichloromethane (10 mL), dried over magnesium sulphate and the solvent distilled under vacuum. The crude residue was purified by PTLC (eluent=ethyl acetate: 1% triethylamine) to give the title compound as a yellow solid; (22 mg, 50%); ¹H NMR (300 MHz, CDCl₃) δ 8.64 (bs, 1H), 8.06 (bs, 1H), 7.10 (d, 1H, J=8.60 Hz), 7.05 (s, 2H, benzoyl Hs), 6.98 (d, 1H, J=8.65 Hz), 3.98 (s, 3H, OMe), 3.89 (s, 3H, OMe), 3.77 (s, 6H, 2×OMe).

e) Preparation of 2-(1-pyrolyl)-7-hydroxy-3-(3,4,5-trimethoxybenzoyl)-6-methoxy-benzo[b]furan (entry 38, Table 1)

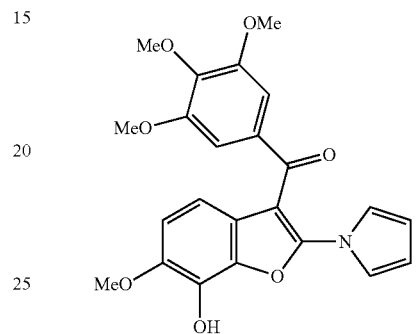

This material was prepared in a similar manner as 2-(1,2,4-triazol-1-yl)-7-hydroxy-3-(3,4,5-trimethoxybenzoyl)-6-methoxy-benzo[b]furan (entry 43, Table 1), above, using pyrrole in place of 1,2,4-triazole as the nucleophile. ¹H NMR (300 MHz, CDCl₃) δ 8.47 (d, 1H, J=1.21 Hz), 7.75 (d, 1H, J=1.20 Hz), 7.27 (d, 1H, J=8.60 Hz), 7.18 (d, 1H, J=8.66 Hz), 7.05 (s, 2H, benzoyl Hs), 3.94 (s, 3H, OMe), 3.74 (s, 6H, 2×OMe), 3.73 (s, 3H, OMe).

f) 2-(4-N-Methylpiperazino)-3-(3,4,5-trimethoxybenzoyl)-6-methoxy-benzo[b]furan (entry 46, Table 1)

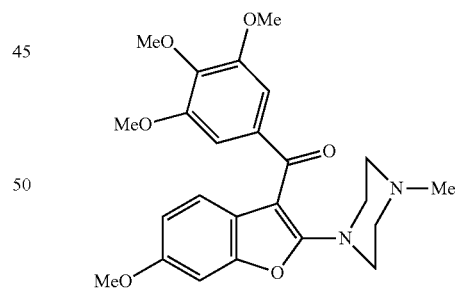

To a stirred solution of 2-bromo-3-(3,4,5-trimethoxybenzoyl)-6-methoxy-benzo[b]furan (20 mg, 0.047 mmol) in a mixture of acetonitrile/dichloromethane; 1:1 (2 mL) was added N-methylpiperazine (50 μL, excess) and the reaction mixture was stirred at room temperature for 1 hour. After this time the solvent was removed by distillation under vacuum and the product was purified by PTLC (eluent=hexane/ethyl acetate; 4:6+1% triethylamine) to give the title compound as a green yellow paste which was crystallized by freeze drying in t-butanol to give a yellow solid; (8 mg, 43%); ¹H NMR (300 MHz, CDCl₃) δ 7.07 (s, 2H, benzoyl Hs), 6.93 (d, 1H, J=8.60 Hz), 6.84 (d, 1H, J=2.25 Hz), 6.65 (dd, 1H, J=8.64, 2.30 Hz), 3.92 (s, 3H, OMe), 3.83 (s, 6H, 2×OMe), 3.78 (s, 3H, OMe), 3.66-3.64 (bm, 4H), 2.65-2.63 (bm, 4H), 2.40 (s, 3H, N-Me); $^{13}$C NMR (75 MHz, CDCl$_3$) δ 188.76 (CO), 162.24, 155.88, 152.72, 149.06, 141.09, 135.36, 121.68, 119.64, 110.42, 106.11, 155.88, 95.63, 60.64, 55.88, 55.44, 53.88, 47.06, 45.29.

Example 11

Compounds of the invention can be prepared by a Larock type coupling involving the palladium mediated cycloaddition of an ortho-iodophenol to a 1,3-diarylpropynone.

a) Preparation of 2-(2-Furyl)-6-methoxy-3-(3,4,5-trimethoxybenzoyl)benzo[b]furan (entry 52, Table 1)

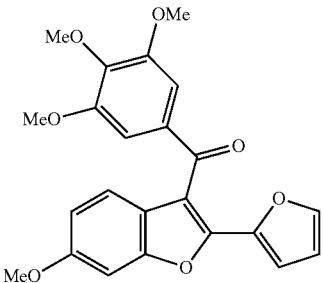 [SMILES: COc1ccc2c(C(=O)c3cc(OC)c(OC)c(OC)c3)c(-c3ccco3)oc2c1]

(i) 3-(2-Furyl)-1-(3,4,5-trimethoxyphenyl)prop-2-yn-1-one

2-Ethynylfuran (200 mg, 2.17 mmol) was dissolved in dry THF (10 ml) and cooled to −78° C. under N$_2$ atmosphere. BuLi (1.2 ml, 2.4 mmol) was added slowly and stirred at −78° C. for 10 min and then 3,4,5-trimethoxybenzaldehyde (500 mg, 2.6 mmol) was added and reaction mixture was stirred for 1 h at −78° C. and then reaction temp raised to room temp. The reaction was quenched by addition of aqueous NH$_4$Cl solution and extracted with EtOAc. The colorless oil was dissolved in dichloromethane and excess of MnO$_2$ was added to it and stirred overnight at room temp. The reaction mixture was filtered through celite plug and evaporated to dryness. 3-(2-furyl)-1-(3,4,5-trimethoxyphenyl)prop-2-yn-1-one was precipitated from ether by slow addition of hexane as off-white powder (65%). $^1$H NMR (300 MHz, CDCl$_3$) δ 3.93 (s, 9H), 6.50-6.52 (m, 1H), 7.01 (d, J=3.6 Hz, 1H), 7.45 (s, 2H), 7.24 (s, 1H), 7.55 (d, J=1.5 Hz).

(ii) 2-(2-Furyl)-6-methoxy-3-(3,4,5-trimethoxybenzoyl)benzo[b]furan

5-Iodo-5-methoxyphenol (125 mg, 0.5 mmol), 3-(2-furyl)-1-(3,4,5-trimethoxyphenyl)-prop-2-yn-1-one (172 mg, 0.6 mmol), LiCl (21.2 mg, 0.5 mmol) and Na$_2$CO$_3$ (265 mg, 2.5 mmol) were added to anhydrous DMF (3 ml) and flushed with N$_2$ three times. Pd(OAc)$_2$ was added to the reaction mixture and again flushed with N$_2$. The reaction mixture was heated to 100-105° C. for 6 h and then reaction was cooled to room temp. Quenched by addition of aqueous NH$_4$Cl solution and extracted with EtOAc. 2-(2-Furyl)-6-methoxy-3-(3,4,5-trimethoxybenzoyl)benzo[b]furan was isolated in 12% yield by silica gel column chromatography using 20 to 40% EtOAc in hexane. $^1$H NMR (300 MHz, CDCl$_3$) δ: 3.75 (s, 6H, OMe), 3.86 (s, 3H, OMe), 3.90 (s, 3H, OMe), 6.44-6.46 (m, 1H), 6.87 (dd, J=2.1, 8.7, 1H), 6.97 (d, J=3.6, 1H), 7.07 (d, J=2.1, 1H), 7.15 (s, 2H), 7.36 (d, J=8.7, 1H), 7.41 (d, J=1.2, 1H). MS (ES) m/z: 408.9 (M+H)$^+$.

Example 12

A series of compounds of the invention were prepared by cycloaddition to an existing C-2 substituent.

a) Preparation of 7-Hydroxy-6-methoxy-2-(2H-tetrazol-5-yl)-3-(3,4,5-trimethoxybenzoyl)-benzo[b]furan (entry 57, Table 1)

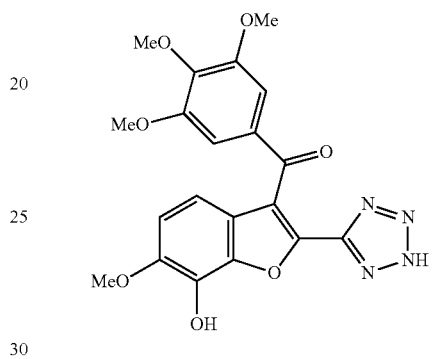

(i) 2-Cyano-7-acetoxy-6-methoxy-3-(3,4,5-trimethoxybenzoyl)-benzo[b]furan

A mixture of 2-bromo-7-acetoxy-3-(3,4,5-trimethoxybenzoyl)-6-methoxybenzo[b]furan (25 mg, 0.05 mmol) and sodium cyanide (15 mg, 0.38 mmol) in dry DMSO (1 mL) under nitrogen at room temperature was stirred for 3.5 hours (tlc), quenched with saturated ammonium chloride solution and diluted with ethyl acetate (20 mL). The organic layer was separated, dried over magnesium sulfate and solvent was distilled to afford the crude material which was purified over silica gel column (eluent—Hexane: diethyl-ether 1:1 to 0:100) to afford 2-cyano-7-hydroxy-3-(3,4,5-trimethoxybenzoyl)-6-methoxybenzo[b]furan as pale cream solid; (13 mg, 65%); $^1$H NMR (300 MHz, CDCl$_3$) δ: 7.29 (d, 1H, J=8.71 Hz), 7.19 (s, 2H, benzoyl Hs), 6.06 (d, 1H, J=8.77 Hz), 5.82 (b, 1H, OH), 3.99 (s, 3H, OMe), 3.96 (s, 3H, OMe), 3.88 (s, 6H, 2×OMe).

(ii) 7-Hydroxy-6-methoxy-2-(2H-tetrazol-5-yl)-3-(3,4,5-trimethoxybenzoyl)-benzo[b]furan Mixture of 2-cyano-7-acetoxy-6-methoxy-3-(3,4,5-trimethoxybenzoyl)-benzo[b]furan (15 mg, 0.04 mmol) ammonium chloride (11 mg, 0.2 mmol) and sodium azide (13 mg, 0.2 mmol) in dry DMF (400 µL) was stirred at 110° C. for 4 hours. More sodium azide (15 mg, 0.23 mmol) was added and stirring was continued for 1 hour (tlc), quenched with saturated ammonium chloride solution and extracted with ethyl-acetate (10 mL×2). The organic layer was dried over magnesium sulfate and solvent was distilled and the crude was purified by silica gel plate to afford the title compound as creamy solid; (3.5 mg, 21%; 1H NMR (300 MHz, CDCl$_3$) δ: 7.85 (1H, NH), 7.26 (d, J=8.54 Hz, 1H), 7.02 (s, 2H, benzoyl Hs), 6.95 (d, J=8.54 Hz, 1H), 5.74 (b, 1H, OH), 3.97 (s, 3H, OMe), 3.88 (s, 3H, OMe), 3.82 (s, 6H, 2×OMe).

b) Preparation of [7-Hydroxy-6-methoxy-2-(2H-[1,2,3]triazol-4-yl)-3-(3,4,5-trimethoxybenzoyl)benzo[b]furan (entry 58, Table 1)

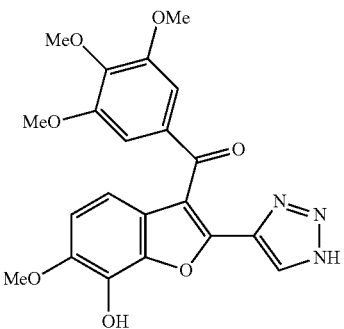 [SMILES: COc1cc(C(=O)c2c(-c3c[nH]nn3)oc3c(O)c(OC)ccc23)cc(OC)c1OC]

(i) 7-Acetoxy-6-methoxy-2-trimethylsilylethynyl-3-(3,4,5-trimethoxybenzoyl)-benzo[b]furan To a stirred solution of the 2-bromo-benzo[b]furan (50 mg, 0.10 mmol) in dichloromethane (1 ml) and triethylamine (0.5 ml) was added Pd(Ph$_3$P)$_2$Cl$_2$ (3.5 mg, 5 mol %) and the reaction vessel was evacuated and backfilled with nitrogen three times. Trimethylsilylacetylene (30 mg, 0.30 mmol) and copper (I) iodide (3 mg, 15 mol %) were added sequentially and the resulting dark mixture was stirred for two hours at room temperature. After this time the reaction was concentrated onto silica and chromatographed giving 7-acetoxy-6-methoxy-2-trimethylsilylethynyl-3-(3,4,5-trimethoxybenzoyl)benzo[b]furan as a resinous solid. $^1$H NMR (300 MHz, CDCl$_3$)-δ: 7.71 (d, 1H, J=8.72 Hz), 7.18 (s, 2H, benzoyl Hs), 7.06 (d, J=8.81 Hz, 1H), 3.93 (s, 3H, OMe), 3.91 (s, 3H, OMe), 3.89 (s, 6H, 2×OMe), 2.42 (s, 3H, acyl-Hs), 0.061 (s, 9H).

(ii) [7-Hydroxy-6-methoxy-2-(2H-1,2,3]triazol-4-yl)-3-(3,4,5-trimethoxybenzoyl)benzo[b]furan Mixture of (7-O-Acyl-6-methoxy-2-trimethylsilylethynyl-3-(3,4,5-trimethoxybenzoyl)-benzo[b]furan (22 mg, 0.044 mmol) ammonium chloride (11 mg, 0.2 mmol) and sodium azide (21 mg, 0.32 mmol) in dry DMF (300 µL) was stirred at 110° C. for 4 hours. Reaction was quenched with saturated ammonium chloride solution and extracted with ethyl-acetate (10 mL×2). The organic layer was dried over magnesium sulphate, solvent was distilled and the crude material was re-dissolved in THF (1 mL) and TBAF (1M solution in THF, 100 µL, 0.1 mmol) was added to it and reaction mixture was stirred for 30 minutes. Solvent was distilled under vacuum and crude product was purified over silica gel plate to afford the title compound as creamy solid; (8 mg, 39%); $^1$H NMR (300 MHz, CDCl$_3$) δ: 8.51 (s, 1H, CH-tetrazole), 7.24 (s, 2H, benzoyl Hs), 6.91 (d, J=8.71 Hz, 1H), 6.78 (d, J=8.61 Hz, 1H), 3.97 (s, 3H, OMe), 3.96 (s, 3H, OMe), 3.81 (s, 6H, 2×OMe).

Example 13

Derivatization of the C-3 carbonyl moiety.

a) Preparation of (E/Z)-6-methoxy-2-(1-methyl-1H-pyrazol-4-yl)-3-(3,4,5-trimethoxybenzoyl)benzo[b]furan oxime (entry 55, Table 1)

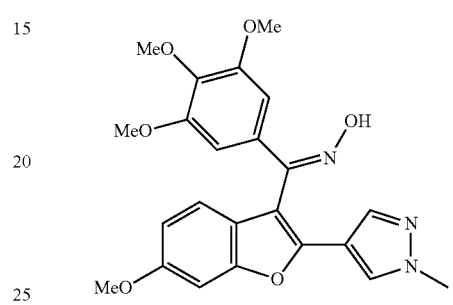

A mixture of 6-methoxy-2-(1-methyl-1H-pyrazol-4-yl)-3-(3,4,5-trimethoxybenzoyl)benzo[b]furan (entry 12, Table 1, above) (0.0189 g, 0.045 mmol), HCl salt of H$_2$NOH (0.01 g, 0.149 mmol) and sodium acetate (0.012 g, 0.149 mmol) in isopropanol (3 ml) was refluxed for three days under N$_2$, than evaporated to dryness under reduced pressure. The residue was suspended in 10 ml of and filtered off. The filtrate was evaporated to dryness and the residue was purified by flash column chromatography (silica-gel, CH$_2$Cl$_2$/ethyl acetate 8:2) giving the title compound as a colorless solid (0.0094 g, 48%). $^1$H NMR (300 MHz, CDCl$_3$) 8.3 (broad s, 1H), 7.71 (s, 1H), 7.55 (s, 1H), 7.04 (s, 2H), 6.7-6.9 (m, 4H), 3.85 (m, 9H), 3.7 (s, 6H). MS (70 eV) 438.2 (M+1), 439.2 (M+2).

b) Preparation of (E/Z)-6-Methoxy-2-(1-methyl-1H-pyrazol-4-yl)-3-(3,4,5-trimethoxybenzoyl)benzo[b]furan 2,4-dinitrophenylhydrazone (entry 56, Table 1)

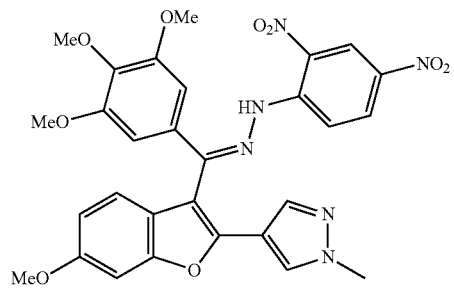 [SMILES: COc1ccc2c(/C(=N/Nc3ccc([N+](=O)[O-])cc3[N+](=O)[O-])c3cc(OC)c(OC)c(OC)c3)c(-c3cnn(C)c3)oc2c1]

A procedure of Morgan et al (J. Med. Chem., 2003, 46, 4552-4563) was used. To a suspension of 2,4-dinitrophenylhydrazine (0.016 g, 0.08 mmol) in anhydrous methanol (2 ml) three drops of concentrated H$_2$SO$_4$ was added at room temperature. After the mixture become homogenous 6-methoxy-2-(1-methyl-1H-pyrazol-4-yl)-3-(3,4,5-trimethoxybenzoyl)benzo[b]furan (entry 12, Table 1, above) (0.0169 g, 0.04 mmol) was added to it and the resulting mixture was stirred overnight at 50° C. under N$_2$. After cooling to room temperature the precipitate was filtered off, washed with fresh methanol (3×0.5 ml) and dried, giving pure title compound (0.02 g, 86.9%) as a deep red crystals. $^1$H NMR (300 MHz, CDCl$_3$) 11.32 (s, 1H), 9.0 (s, 1H), 8.35 (d, J=9.5 Hz, 1H), 8.15 (d, J=9.5 Hz, 1H), 7.63 (s, 1H), 7.55 (s, 1H), 6.8-7.13 (m, 5H), 3.87 (m, 15H).

Biological Methods

In Vivo Animal Model Studies:

The effect of 35 mg/kg/d CA4-P, compound entry 8, compound entry 9, compound entry 10 and compound entry 23 (administered at 35 mg/kg/d for 3 days then 17.5 mg/kg/d for 3 days then none) on MDA-MB-231 tumour growth is summarised in FIG. 1. At the administered doses, CA4-P and compound entry 23 effectively inhibited MDA-MB-231 tumour growth.

The effect of CA4-P and test compounds and saline on MDA-MB-231 tumour growth. Each group consisted of 5 mice. The data represent the mean tumour volume; bars SEM.

Figure 2:
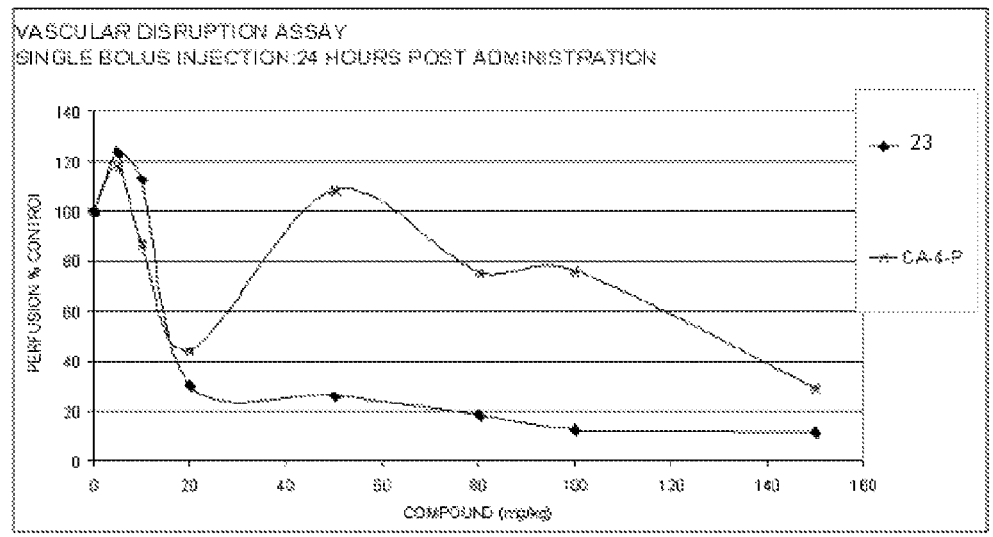
FIG. 2 depicts a graph of comparative perfusion % control against compound (mg/kg) for CA4-P and compound entry 23.

The effect CA4-P and compound of entry 23 in Table 1 on tumour perfusion in MDA-MB-231 tumours at various doses (from 1 mg/kg to 150 mg/kg) is summarised in FIG. 2.

Proliferation Assay—Activated Endothelium:

Human umbilical vein endothelial cells (CC-2519, Clonetics) were plated at 2500 cells/well in EGM2 (CC-3162, Clonetics) in a 96 well plate in triplicate. Cells were cultured overnight at 37° C. 5% CO$_2$. Medium was subsequently replaced with fresh medium including the compound or negative control. Cells were cultured for a period of 48 hrs. An MTT assay was performed to measure changes in cell numbers. Briefly, 20 µl of MTT reagent was added to cells containing 100 µl of EGM2 and incubated at 37° C. for 2 hours. Absorbance was measured at 492 nm.

Vascular Disruption Assay:

Female athymic BALB/c-nu/nu mice (nude mice) were used for this study. Mice were between 6-8 weeks old and were purchased from the Animal Resource Centre, Perth, Western Australia and allowed to acclimatize for a couple of days. All the animals were housed under pathogen-free conditions and cared for in accordance with Flinders University of South Australia and NH&MRC guidelines and the Australian Code of Practice for the care and use of animals for scientific purposes. The human breast cancer MDA MB 231 was grown as orthotopic xenografts in the mammary fat pad of nude mice. Each mouse was injected with 2×10$^6$ cells in 50 µl Dulbecco's PBS subcutaneously just above the mammary fat pad, below the right forward limb. Tumors were selected for treatment when they reached a diameter of 100-150 mm$^3$ (3 weeks after implantation). The test compound was dissolved in saline solution and injected intravenously at concentrations ranging from 150 mg/kg-1 mg/kg in a total volume of 400 ul. Tumor bearing animals were injected intravenously with 10 mg/kg Hoechst 33342 24 hours after the injection of the test compound. Animals were euthanised 1 minute after the Hoechst 33342 injection. Tumors were recovered for histochemical analysis. Tumor perfusion analysis was performed by assessing the amount of Hoechst 33342 staining across an entire tumor cross-section. 10 micron sections of frozen tumor biopsies were viewed under an ultraviolet light filter. Using a 4× objective lens, 8-bit monochromatic images were captured in succession, representing the total area of the tumor section. Composite images of the total tumor section were generated by overlaying common areas of the monochromatic images. Hematoxylin and Eosin-Y staining of the same tumor section was performed to identify non-tumor regions. Non-tumor regions were mapped on Hoechst 33342 composite images and excluded from the quantitation analysis. Quantitation was performed by measuring the pixel area of Hoechst 33342 staining and the total pixel area of the tumor region. Perfusion was expressed as a percentage of Hoechst 33342 stained area to total tumor area.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form or suggestion that that prior art forms part of the common general knowledge in Australia.

The invention claimed is:

1. A method for treating a disease state by inhibiting tubulin polymerization including the step of administering to a patient in need thereof a compound of formula (Ia), or a salt thereof;

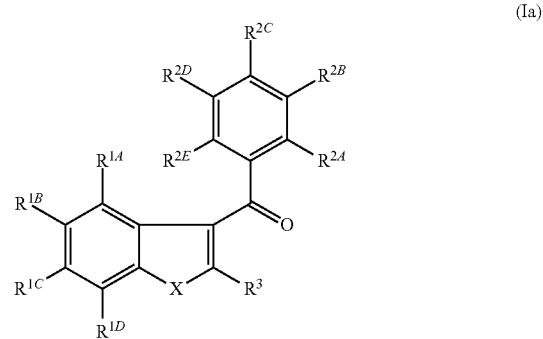

wherein;
X represents O or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$, $R^{1B}$ and $R^{1D}$ each independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy;

$R^{1C}$ represents hydroxy, optionally substituted alkenyloxy, optionally substituted alkoxy, optionally substituted alkynyloxy, optionally substituted arylalkoxy, optionally substituted aryloxy, optionally substituted alkylthio or optionally substituted amino;

$R^{2A}$, $R^{2C}$ and $R^{2E}$ independently represents H, carboxyl, cyano, dihalomethoxy, halogen, hydroxy, nitro, pentahaloethyl, phosphono, phosphorylamino, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy;

$R^{2D}$ and $R^{2B}$ independently represent hydroxy, optionally substituted arylalkoxy, optionally substituted alkenyloxy, optionally substituted alkoxy, optionally substituted alkynyloxy, or optionally substituted aryloxy;

$R^3$ represents an optionally substituted heteroaryl group or an optionally substituted heterocyclyl group.

2. A method according to claim 1, wherein $R^{1C}$ represents hydroxy, alkoxy, alkylthio, or mono or di-alkylamino.

3. A method according to claim 1, wherein $R^{2D}$ and $R^{2B}$ independently represent hydroxy or alkoxy.

4. A method according to claim 1, wherein $R^{1A}$, $R^{1B}$, $R^{2A}$ and $R^{2E}$ represent H, and $R^{1C}$ represents $C_{1-3}$alkoxy, $C_{1-3}$alkylthio, $C_{1-3}$alkylamino or $C_{1-3}$dialkylamino.

5. A method according to claim 4, wherein $R^{2C}$ represents H, halogen, or an alkoxy group, $R^{1D}$ represents halogen, hydroxy, optionally substituted amino or an optionally substituted alkoxy group, and $R^{2D}$ and $R^{2B}$ independently represent an alkoxy group.

6. A method according to claim 1 wherein the compound of formula (Ia) is represented by a compound of formula (Ib), or a pharmaceutically acceptable salt thereof;

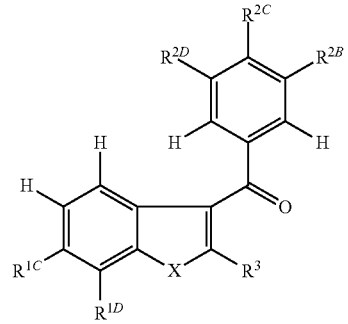

wherein;
X represents O or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$alkoxy, $C_{1-3}$alkylthio, $C_{1-3}$alkylamino, or $C_{1-3}$dialkylamino;

$R^{1D}$ represents H, hydroxy, halogen, optionally substituted alkoxy, or optionally substituted amino;

$R^{2D}$ and $R^{2B}$ independently represent alkoxy;

$R^{2C}$ represents H, halogen, or alkoxy; and $R^3$ represents an optionally substituted heteroaryl group or an optionally substituted heterocyclyl group.

7. A method according to claim 6, wherein $R^{1D}$ is hydroxy or amino and $R^{2C}$ represents H, F or an alkoxy group.

8. A method according to claim 7, wherein $R^{2D}$ and $R^{2B}$ both represent a methoxy group.

9. A method according to claim 6, wherein $R^{1D}$ is hydroxy or amino, and $R^{2B}$, $R^{2C}$, and $R^{2D}$ are methoxy.

10. A method according to claim 1, wherein X is O.

11. A method according to claim 1, wherein $R^3$ represents an optionally substituted heteroaryl group.

12. A method according to claim 11, wherein the optionally substituted heteroaryl group is a 5 or 6 membered optionally substituted heteroaryl group.

13. A method according to claim 12, wherein the optionally substituted heteroaryl group has from 1 to 4 heteroatoms selected from O, S, Se or N and mixtures thereof.

14. A method according to claim 11, wherein the optionally substituted heteroaryl group is selected from optionally substituted imidazolyl, optionally substituted triazolyl, optionally substituted pyrrolyl, optionally substituted pyrazolyl, optionally substituted thiazolyl, optionally substituted thiophenyl, optionally substituted furanyl, optionally substituted selenophenyl, optionally substituted oxazolyl, optionally substituted isoazolyl, optionally substituted isothiazolyl, optionally substituted oxadiazolyl, optionally substituted thiadiazolyl, optionally substituted tetrazolyl, optionally substituted oxatriazolyl, optionally substituted thiatriazolyl, optionally substituted indolyl, optionally substituted benzo[b]furanyl and optionally substituted benzothiophenyl, optionally substituted pyridinyl, optionally substituted pyrimidinyl, optionally substituted pyronyl, optionally substituted coumarinyl, optionally substituted chromonyl, optionally substituted pyridonyl, optionally substituted purinyl (adeninyl and guaninyl), optionally substituted uracilyl, optionally substituted thymidinyl, optionally substituted cytosinyl, optionally substituted quinolinyl and optionally substituted isoquinolinyl.

15. A method according to claim 1 wherein the compound is:

6-Methoxy-2-(1H-pyrazol-4-yl)-3-(3,4,5-trimethoxybenzoyl)benzo[b]furan;
[2-(1-Benzyl-1H-pyrazol-4-yl)-6-methoxy-benzo[b]furan-3-yl]-(3,4,5-trimethoxyphenyl)-methanone;
[7-Hydroxy-6-methoxy-2-(1H-pyrazol-4-yl)-benzo[b]furan-3-yl]-(3,4,5-trimethoxyphenyl)-methanone;
[2-(1H-Imidazol-4-yl)-6-methoxy-benzo[b]furan-3-yl]-(3,4,5-trimethoxyphenyl)-methanone;
2-(4-N-Methylpyrazolyl)-3-(3,4,5-trimethoxybenzoyl)-6-methoxy-7-hydroxy-benzo[b]furan;
2-(4-N-Methylpyrazolyl)-3-(3,5-dimethoxybenzoyl)-6-methoxy-7-hydroxy-benzo[b]furan;
2-(4-N-Methylpyrazolyl)-3-(3,5-dimethoxybenzoyl)-6-methoxy-7-isopropoxy-benzo[b]furan;
2-(N-Methyl-pyrazole)-6,7-oxazol-7-yl]-(3,4,5-trimethoxy-phenyl)-benzo[b]furan;
{4-[6-Methoxy-3-(3,4,5-trimethoxy-benzoyl)-benzo[b]furan-2-yl]-pyrazol-1-yl}-acetic acid ethyl ester;
{4-[6-Methoxy-3-(3,4,5-trimethoxy-benzoyl)-benzo[b]furan-2-yl]-pyrazol-1-yl}-acetic acid;
2-{4-[6-Methoxy-3-(3,4,5-trimethoxy-benzoyl)-benzo[b]furan-2-yl]-pyrazol-1-yl}-acetamide;
{6-Methoxy-2-[1-(4-methoxy-phenyl]-1H-pyrazol-4-yl]-benzo[b]furan-3-yl}-(3,4,5-trimethoxyphenyl)-methanone;
{2-[1-(2-Dimethylamino-ethyl)-1H-pyrazol-4-yl]-6-methoxy-benzo[b]furan-3-yl}-(3,4,5-trimethoxyphenyl)-methanone;
2-{4-[7-Hydroxy-6-methoxy-3-(3,4,5-trimethoxybenzoyl)-benzofuran-2-yl]-pyrazol-1-yl}-acetamide;
[2-(1-Methyl-1H-Imidazol-4-yl)-6-methoxy-benzo[b]furan-3-yl]-(3,4,5-trimethoxyphenyl)-methanone;
2-(4-N-Methylpyrazolyl)-3-(3,4,5-trimethoxybenzoyl)-6-methoxy-7-O-disodiumphosphate-benzo[b]furan;
2-(2-Thiazolyl)-7-O-disodiumphosphate-6-methoxy-3-(3,4,5-trimethoxybenzoyl)-benzo[b]furan;
7-(O-disodiumphosphate)-2-(2-furyl)-6-methoxy-3-(3,4,5-trimethoxybenzoyl)benzo-[b]furan;
7-(O-Disodiumphosphate)-2-(2-thiophenyl)-6-methoxy-3-(3,4,5-trimethoxybenzoyl)benzo-[b]furan;
2-Imidazol-1-yl-7-O-bis-(triethylammonium)phosphate-6-methoxy-3-(3,4,5-trimethoxybenzoyl)-benzo[b]furan;
2S-2-Amino-3-hydroxy-N-(6-methoxy-2-(1-methyl-1H-pyrazol-4-yl)-3-(3,4,5-trimethoxybenzoyl)benzofuran-7-yl)propanamide;
2-(Furan-2-yl)-6-methoxy-3-(3,4,5-trimethoxybenzoyl)benzofuran-7-yl ester of N$^\gamma$-nitro-L-arginine;
[6-Methoxy-2-(1-methyl-1-pyrazol-4-yl)-1H-indol-3-yl]-(3,4,5-trimethoxyphenyl)-methanone;
[7-Amino-6-methoxy-2-(1-methyl-1-pyrazol-4-yl)-benzofuran-3-yl]-(3,4,5-trimethoxyphenyl)-methanone;
[6-Methoxy-7-nitro-2-(1-methyl-1-pyrazol-4-yl)-benzo[b]furan-3-yl]-(3,4,5-trimethoxyphenyl)-methanone;
7-Amino-6-methoxy-2-(1-methyl-1H-pyrazol-4-yl)-3-(3,4,5-trimethoxyphenylthio)benzo[b]furan;
7-Fluoro-6-methoxy-2-(1-methyl-1H-pyrazol-4-yl)-benzo[b]furan-3-yl]-(3,4,5-trimethoxyphenyl)-methanone;
2-{4-[7-Fluoro-6-methoxy-3-(3,4,5-trimethoxybenzoyl)benzofuran-2-yl]-1H-pyrazol-1-yl}acetamide;
7-Hydroxy-6-methoxy-2-(3-methyl-3H-imidazol-4-yl)-3-(3,4,5-trimethoxybenzoyl)-benzo[b]furan;
2-(6-Methoxy-pyridin-3-yl)-3-(3,4,5-trimethoxybenzoyl)-6-methoxy-benzo[b]furan;
2-(4-N-Methyl-4-pyrazole)-3-(3,4,5-trimethoxybenzoyl)-6-methoxy-benzo[b]furan;
2-(3-Thiophenyl)-3-(3,4,5-trimethoxybenzoyl)-6-methoxy-benzo[b]furan;
2-(4-3,5-dimethyl-isoxazolyl)-7-hydroxy-3-(3,4,5-trimethoxy-benzoyl)-6-methoxy-benzo[b]furan;
2-(4-N-isobutyl-pyrazolyl)-7-hydroxy-3-(3,4,5-trimethoxy-benzoyl)-6-methoxy-benzo[b]furan;
2-(2-thiophene)-7-hydroxy-3-(3,4,5-trimethoxybenzoyl)-6-methoxy-benzo[b]furan;
2-(2-thiophene-5-carbaldehyde)-7-hydroxy-3-(3,4,5-trimethoxybenzoyl)-6-methoxy-benzo[b]furan;
2-(2-furanyl)-7-hydroxy-3-(3,4,5-trimethoxybenzoyl)-6-methoxy-benzo[b]furan;
2-(2-thiazole)-7-hydroxy-3-(3,4,5-trimethoxybenzoyl)-6-methoxy-benzo[b]furan;
2-(N-imidazolyl)-7-hydroxy-3-(3,4,5-trimethoxybenzoyl)-6-methoxy-benzo[b]furan;
2-(1N-1,2,3-triazolyl)-7-hydroxy-3-(3,4,5-trimethoxybenzoyl)-6-methoxy-benzo[b]furan;
2-(N-pyrazolyl)-7-hydroxy-3-(3,4,5-trimethoxybenzoyl)-6-methoxy-benzo[b]furan;
2-(1,2,4-triazol-1-yl)-7-hydroxy-3-(3,4,5-trimethoxybenzoyl)-6-methoxy-benzo[b]furan;
2-(1-pyrolyl)-7-hydroxy-3-(3,4,5-trimethoxybenzoyl)-6-methoxy-benzo[b]furan;
2-(4-N-Methylpiperazino)-3-(3,4,5-trimethoxybenzoyl)-6-methoxy-benzo[b]furan;
2-(2-Furyl)-6-methoxy-3-(3,4,5-trimethoxybenzoyl)benzo[b]furan;
7-Hydroxy-6-methoxy-2-(2H-tetrazol-5-yl)-3-(3,4,5-trimethoxybenzoyl)-benzo[b]furan;
[7-Hydroxy-6-methoxy-2-(2H-[1,2,3]triazol-4-yl)-3-(3,4,5-trimethoxybenzoyl)benzo[b]furan;
(E/Z)-6-methoxy-2-(1-methyl-1H-pyrazol-4-yl)-3-(3,4,5-trimethoxybenzoyl)benzo[b]furan oxime;
(E/Z)-6-Methoxy-2-(1-methyl-1H-pyrazol-4-yl)-3-(3,4,5-trimethoxybenzoyl)benzo[b]furan 2,4-dinitrophenylhydrazone;

or a pharmaceutically acceptable salt thereof.

16. A method according to claim 1 wherein the compound is 2-(4-N-Methylpyrazolyl)-3-(3,4,5-trimethoxybenzoyl)-6-methoxy-7-hydroxy-benzo[b]furan, or a pharmaceutically acceptable salt thereof.

17. A method according to claim 1 wherein the disease state to be treated is a tumour.

18. A method according to claim 17 wherein the tumour is selected from leukemia; melanoma; colon, lung, ovarian, skin, breast, prostate, CNS, or renal cancer.

19. A method according to claim 1 wherein the disease state is inflammation associated with rheumatoid arthritis, inflammatory bowel disease, Crohn's disease, or psoriasis.

* * * * *